US010098567B2

(12) United States Patent
Nelson et al.

(10) Patent No.: US 10,098,567 B2
(45) Date of Patent: Oct. 16, 2018

(54) MEDICAL DEVICE POSITION LOCATION SYSTEMS, DEVICES AND METHODS

(71) Applicant: Teleflex Medical Devices S.à r.l, Luxembourg (LU)

(72) Inventors: Peter E. Nelson, Longmont, CO (US); Robert D. Zellers, Lafayette, CO (US); Charles W. Henry, Denver, CO (US)

(73) Assignee: TELEFLEX MEDICAL DEVICES S.À R.L, Luxembourg (LU)

(*) Notice: Subject to any disclaimer, the term of this patent is extended or adjusted under 35 U.S.C. 154(b) by 0 days.

(21) Appl. No.: 15/141,843

(22) Filed: Apr. 29, 2016

(65) Prior Publication Data
US 2016/0320210 A1 Nov. 3, 2016

Related U.S. Application Data

(60) Provisional application No. 62/154,687, filed on Apr. 29, 2015.

(51) Int. Cl.
*G01N 27/02* (2006.01)
*A61B 5/06* (2006.01)
*A61B 5/0408* (2006.01)

(52) U.S. Cl.
CPC ............ *A61B 5/062* (2013.01); *A61B 5/0408* (2013.01)

(58) Field of Classification Search
CPC ... A61B 2034/2051; A61B 5/06; A61B 34/20; A61B 5/062; G01R 33/0206
See application file for complete search history.

(56) References Cited

U.S. PATENT DOCUMENTS

| | | | |
|---|---|---|---|
| 3,775,765 A | 11/1973 | Di Piazza et al. | |
| 4,173,228 A | 11/1979 | Van Steenwyk | |
| 4,959,613 A * | 9/1990 | Yamamoto ........... | G01R 33/385 324/318 |

(Continued)

FOREIGN PATENT DOCUMENTS

WO 2012068365 A2 5/2012

OTHER PUBLICATIONS

Search Report and Written Opinion of the International Search Authority for related International Patent Application No. PCT/US16/29987, dated Aug. 4, 2016.

*Primary Examiner* — Dixomara Vargas
*Assistant Examiner* — Adam Clarke
(74) *Attorney, Agent, or Firm* — Baker Hostetler LLP

(57) ABSTRACT

Methods, devices and systems for location of the disposition of a medical probe in a subject are disclosed. An array of electromagnetic drive coil sets, each set having two or three dimensionally oriented drive coils, a sensor coil being electromagnetically communicative with the array of electromagnetic drive coil sets, a discrete core wire providing response to electrical stimuli of the subject, and a system controller communicative with and adapted to energize one or more of the electromagnetic coils in the array of electromagnetic drive coil sets are disclosed. The energizing of the one or more of the electromagnetic coils including one or more of energizing the coils singly, or in pairs of x-y and y-z or x-z coils while measuring the response of the sensor coil, whereby the system uses the measurements of the responses of the sensor coil to calculate the location of the sensor coil relative to said drive coil sets.

24 Claims, 46 Drawing Sheets

(56) References Cited

U.S. PATENT DOCUMENTS

| | | | |
|---|---|---|---|
| 5,425,367 A | 6/1995 | Shapiro et al. | |
| 5,769,843 A | 6/1998 | Abela et al. | |
| 5,913,820 A * | 6/1999 | Bladen | A61B 5/06 |
| | | | 128/899 |
| 5,997,473 A | 12/1999 | Taniguchi et al. | |
| 6,534,982 B1 | 3/2003 | Jakab | |
| 6,615,155 B2 | 9/2003 | Gilboa | |
| 6,677,755 B2 * | 1/2004 | Belt | G01R 33/3415 |
| | | | 324/318 |
| 2007/0167722 A1 | 7/2007 | Bladen et al. | |
| 2010/0317962 A1 * | 12/2010 | Jenkins | A61B 5/055 |
| | | | 600/411 |
| 2012/0126808 A1 * | 5/2012 | Knopp | A61B 5/0515 |
| | | | 324/301 |
| 2012/0130228 A1 * | 5/2012 | Zellers | A61B 5/062 |
| | | | 600/424 |
| 2012/0130229 A1 | 5/2012 | Zellers | |
| 2013/0303945 A1 | 11/2013 | Blumenkranz | |
| 2014/0051983 A1 | 2/2014 | Schroeder et al. | |
| 2014/0139223 A1 | 5/2014 | Olsson | |
| 2014/0306698 A1 * | 10/2014 | Bontus | A61B 5/0515 |
| | | | 324/234 |

\* cited by examiner

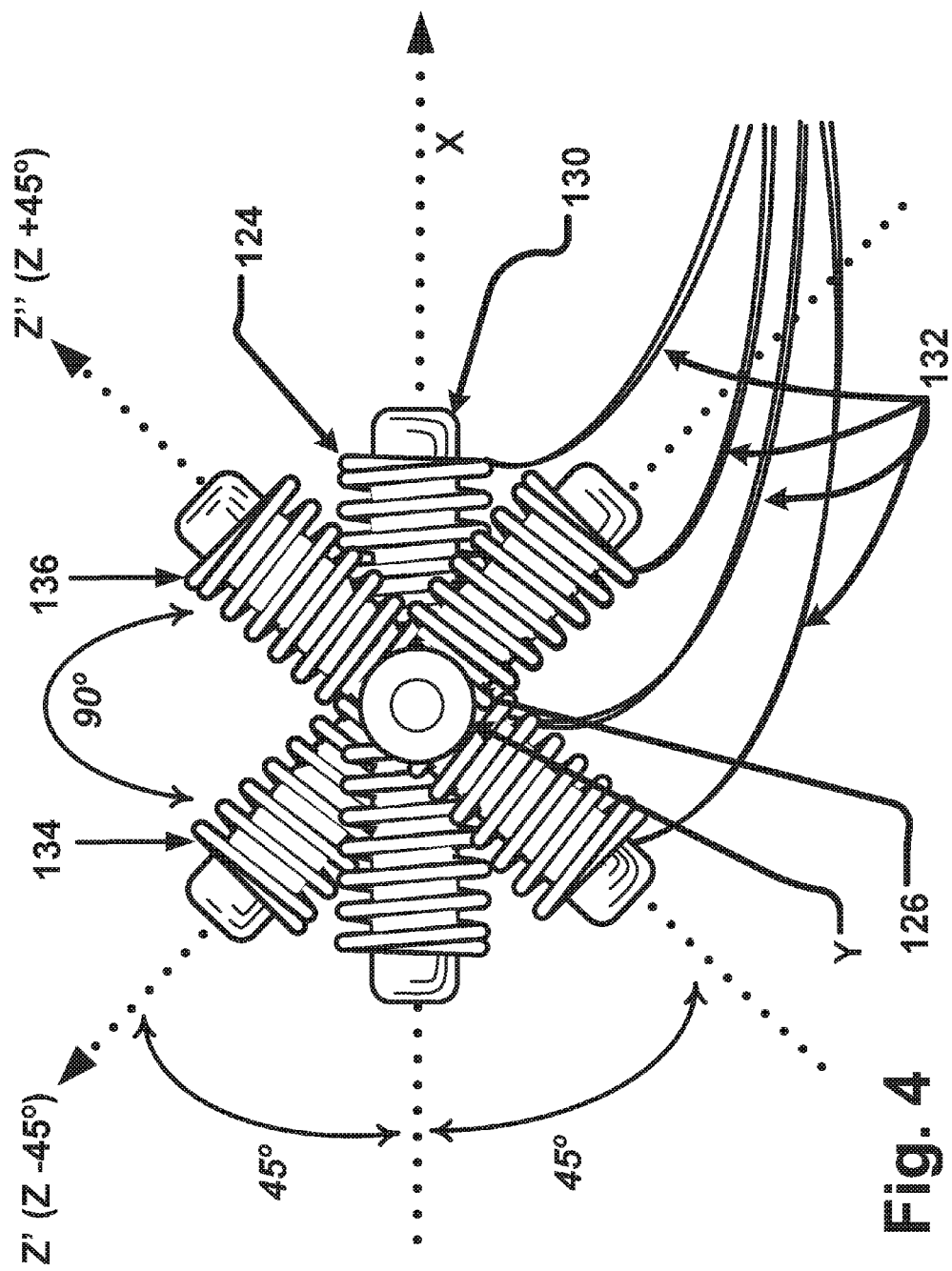

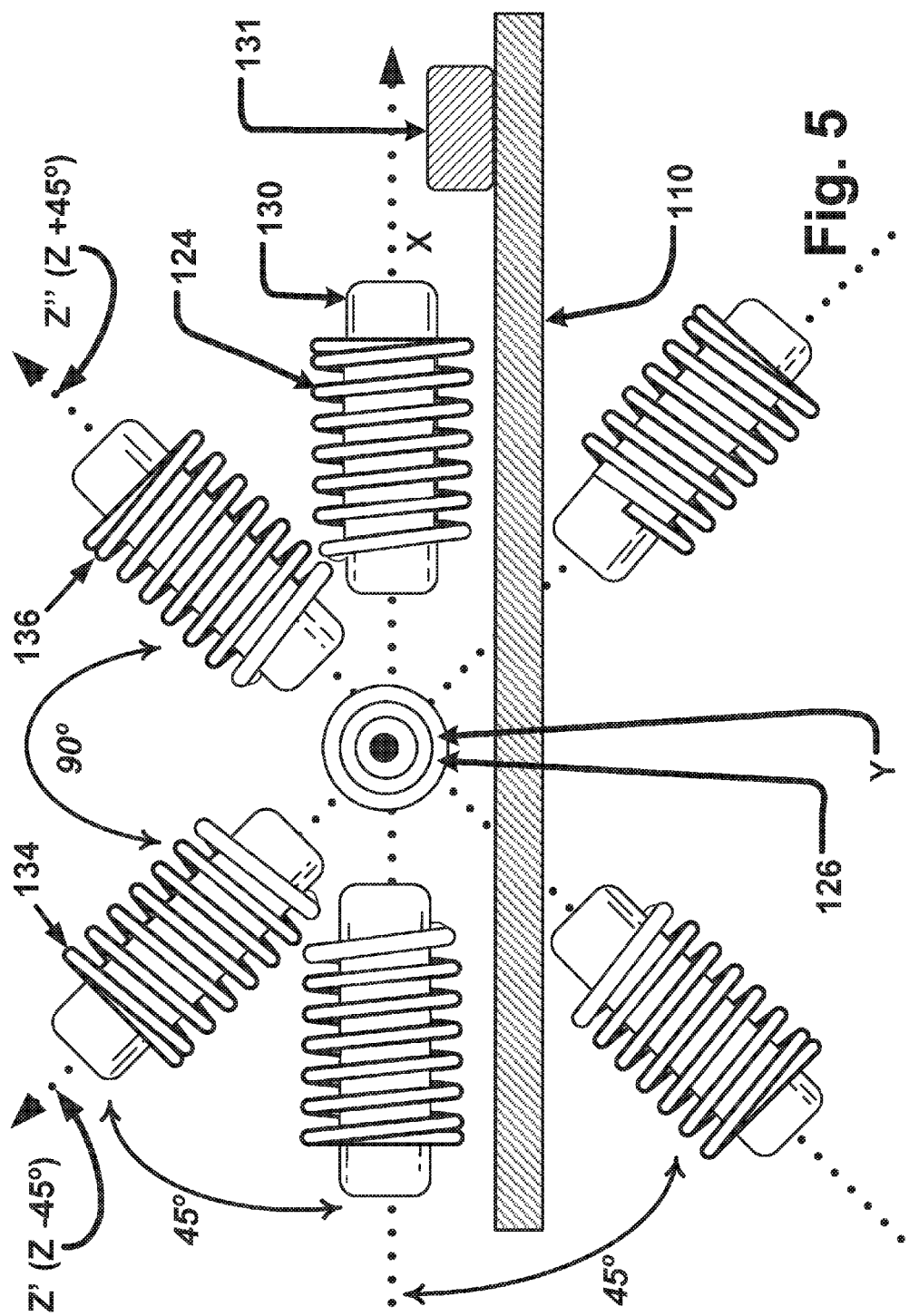

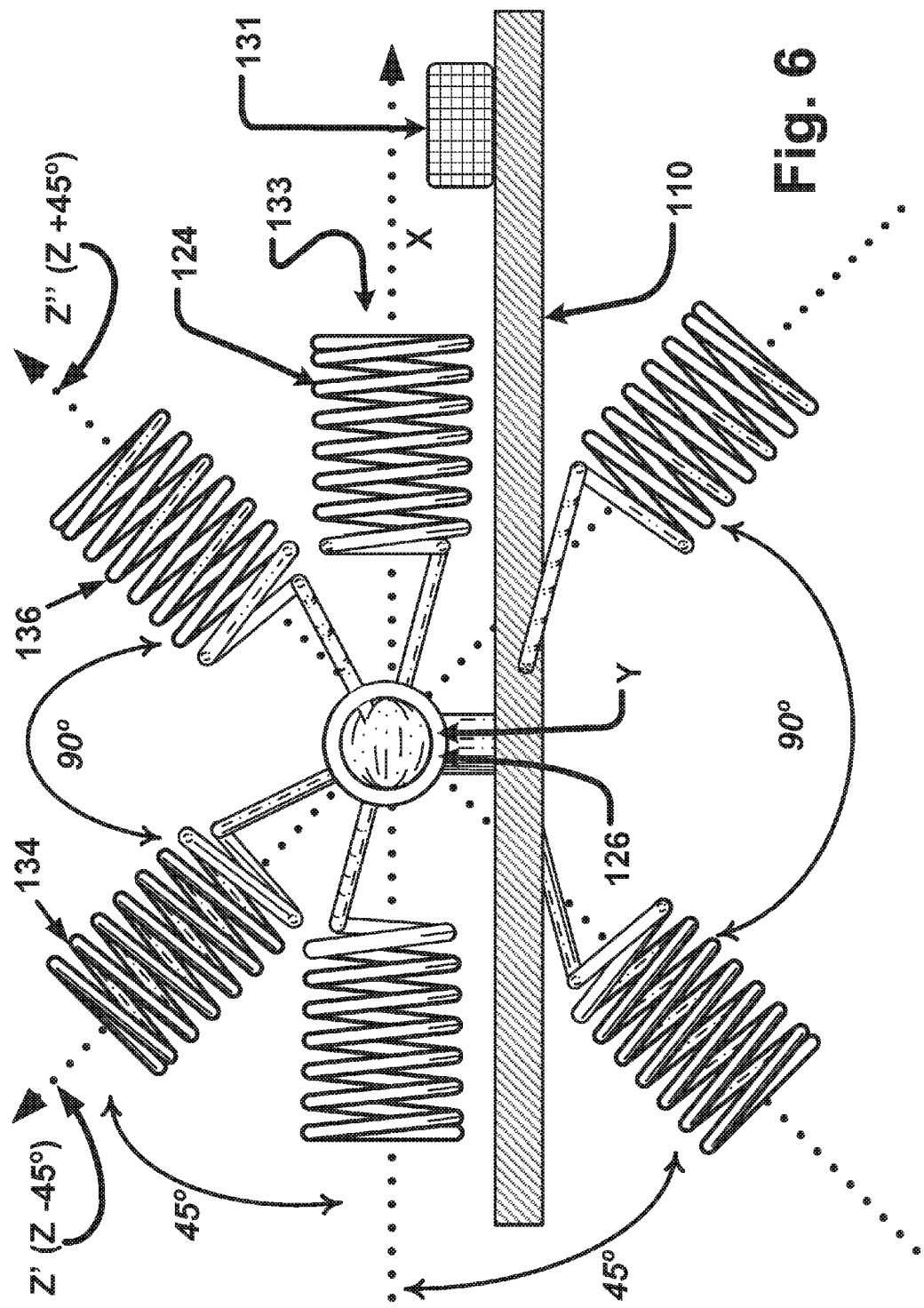

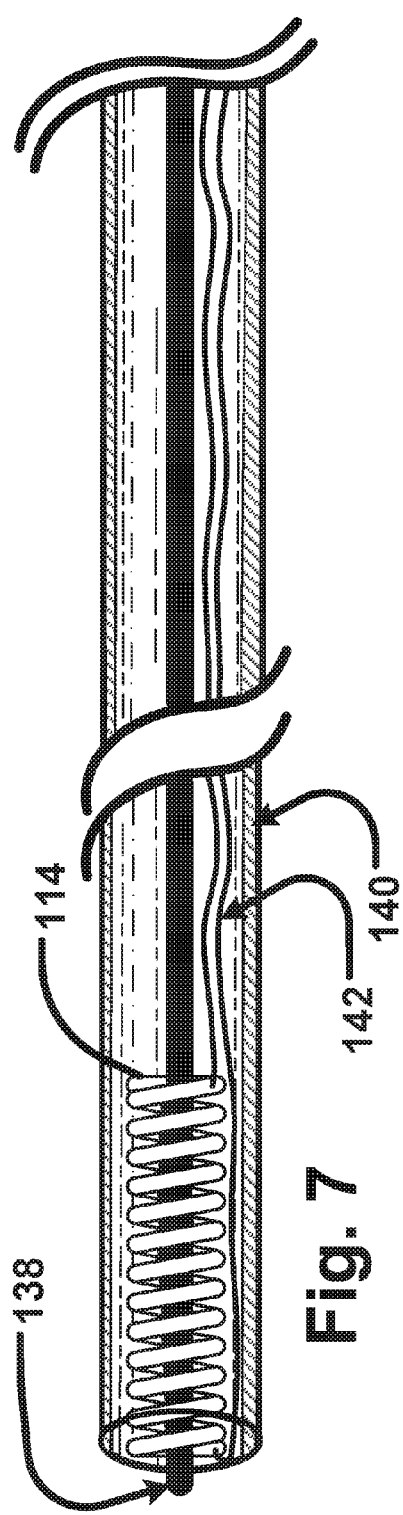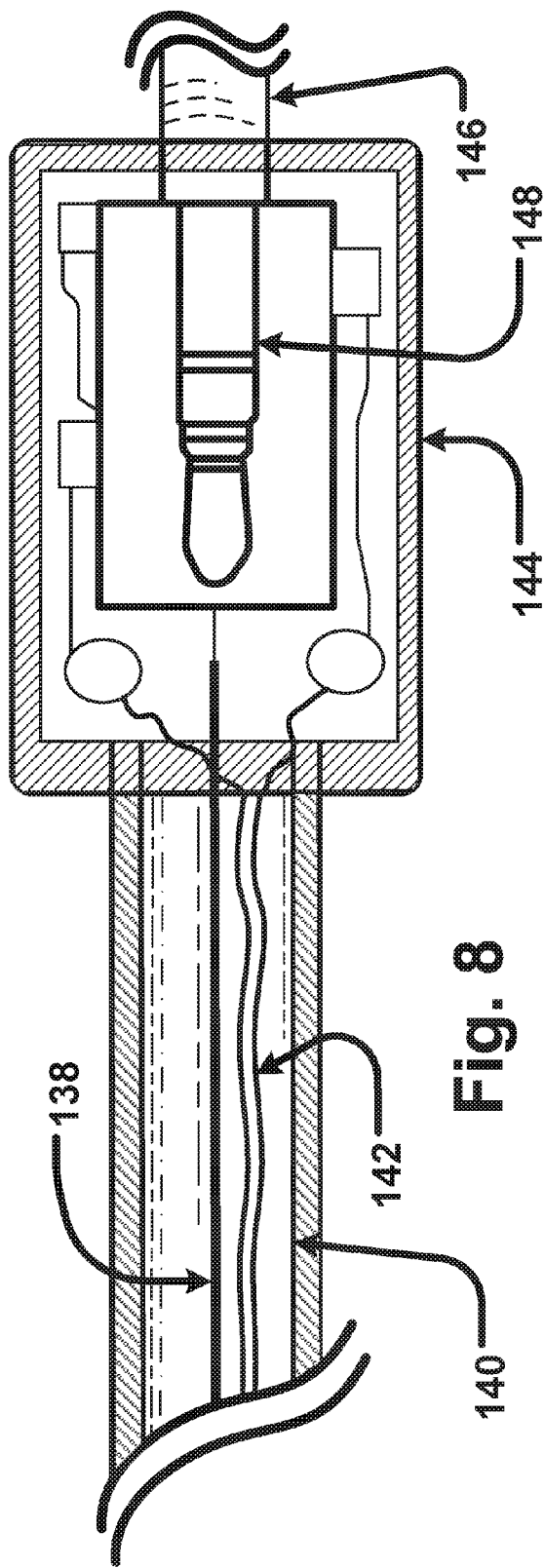

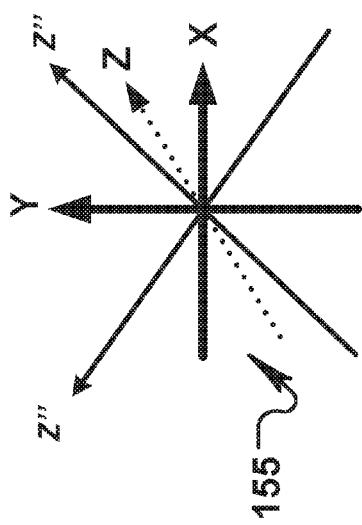
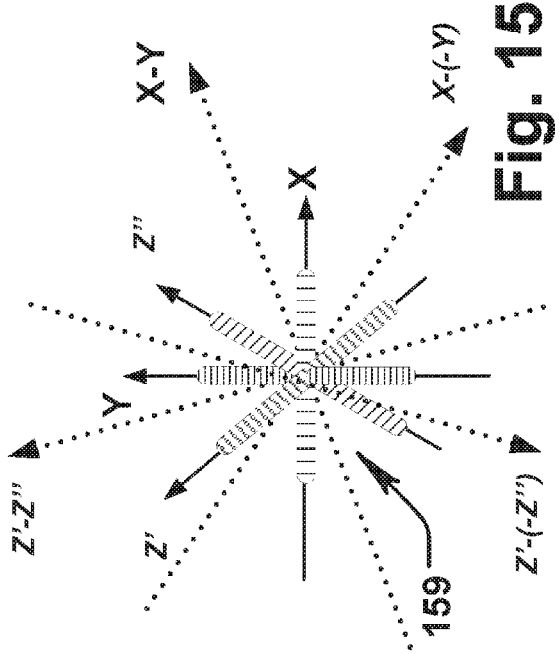
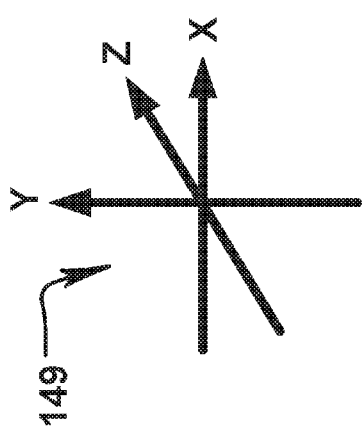
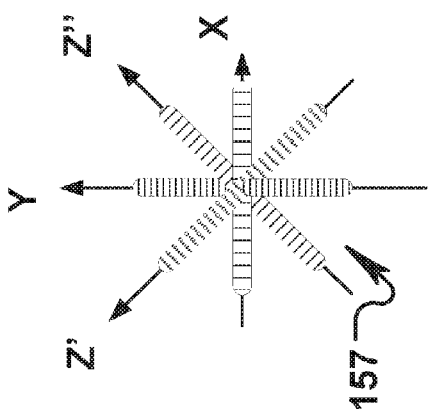

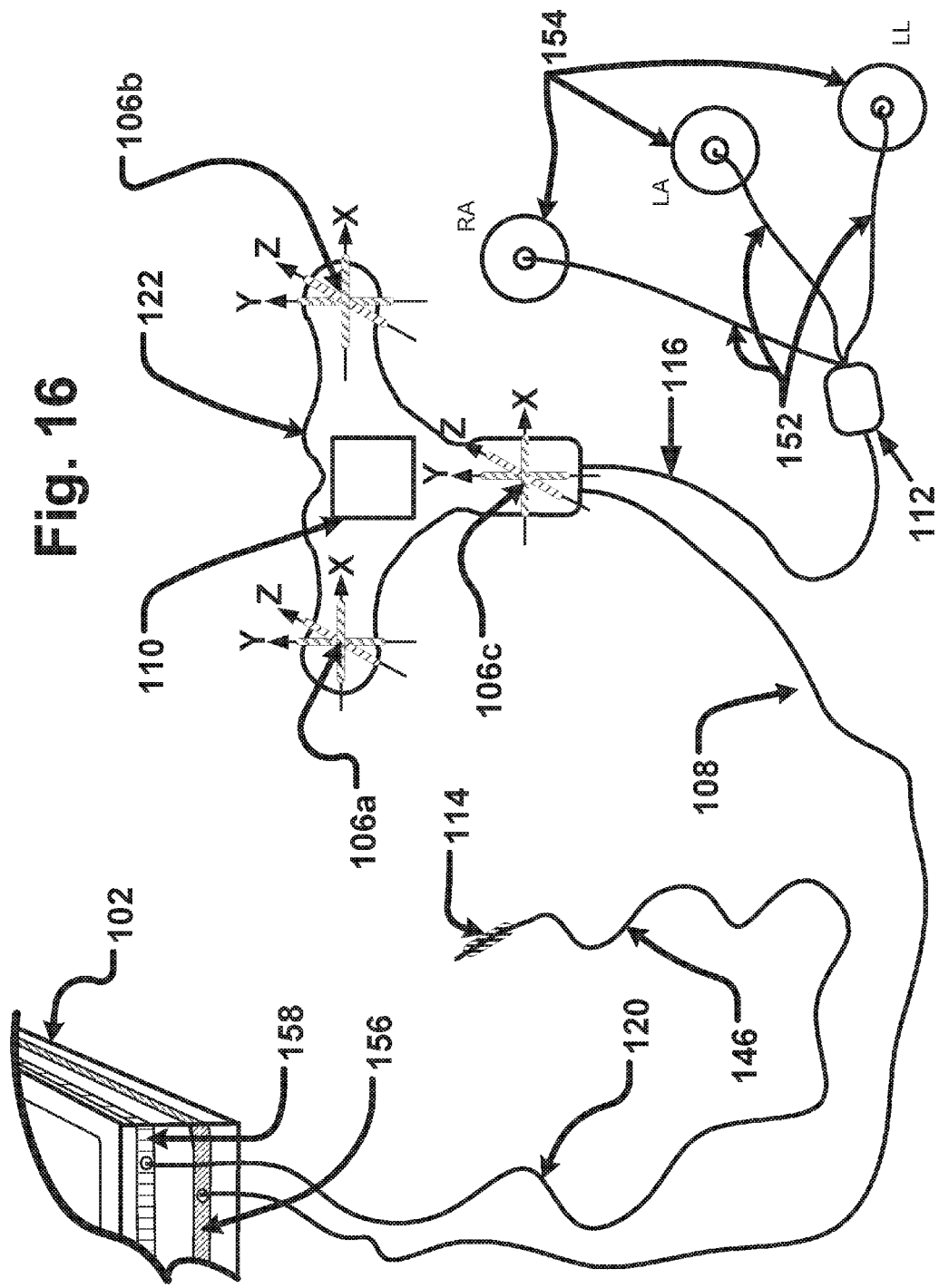

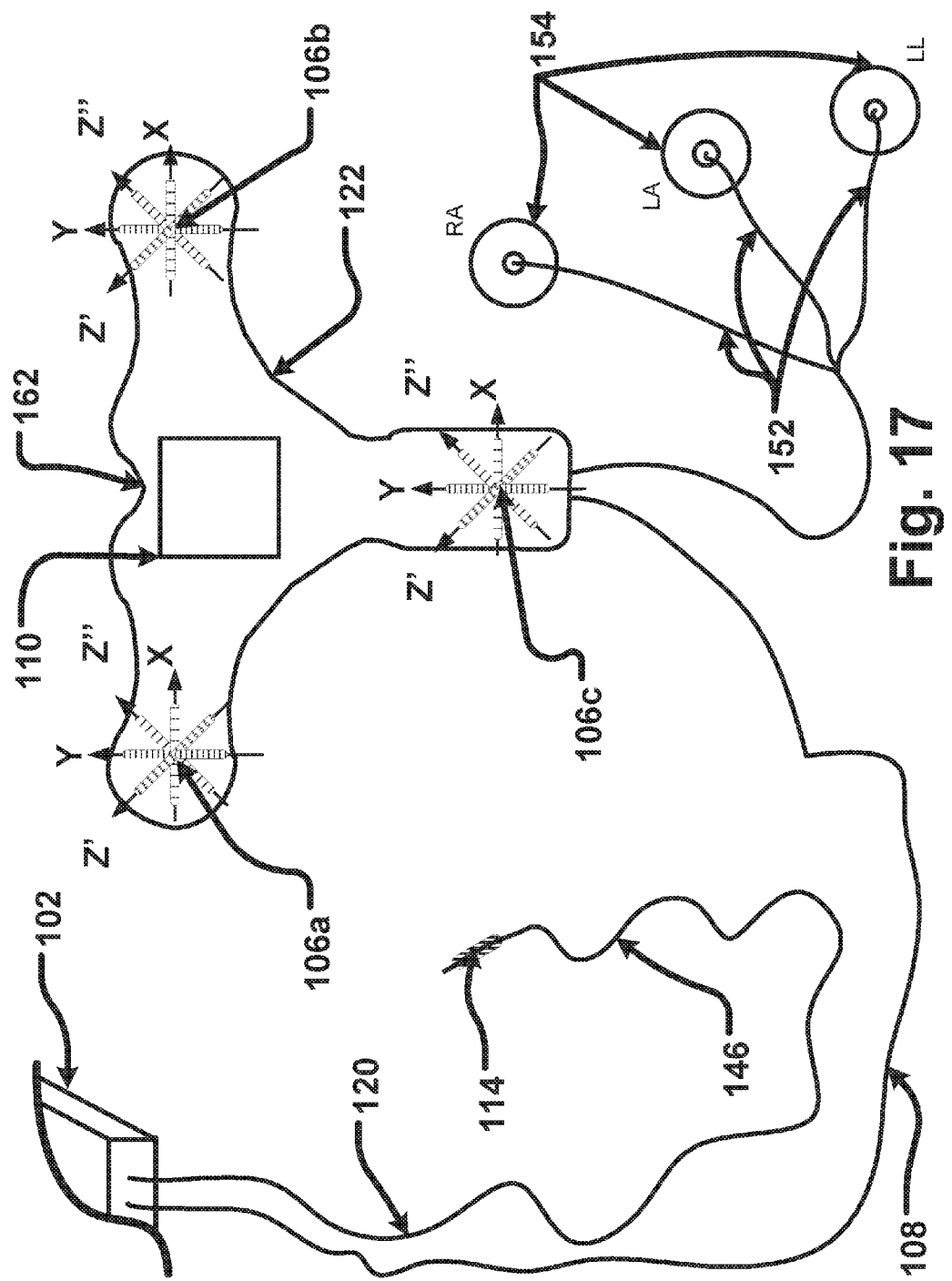

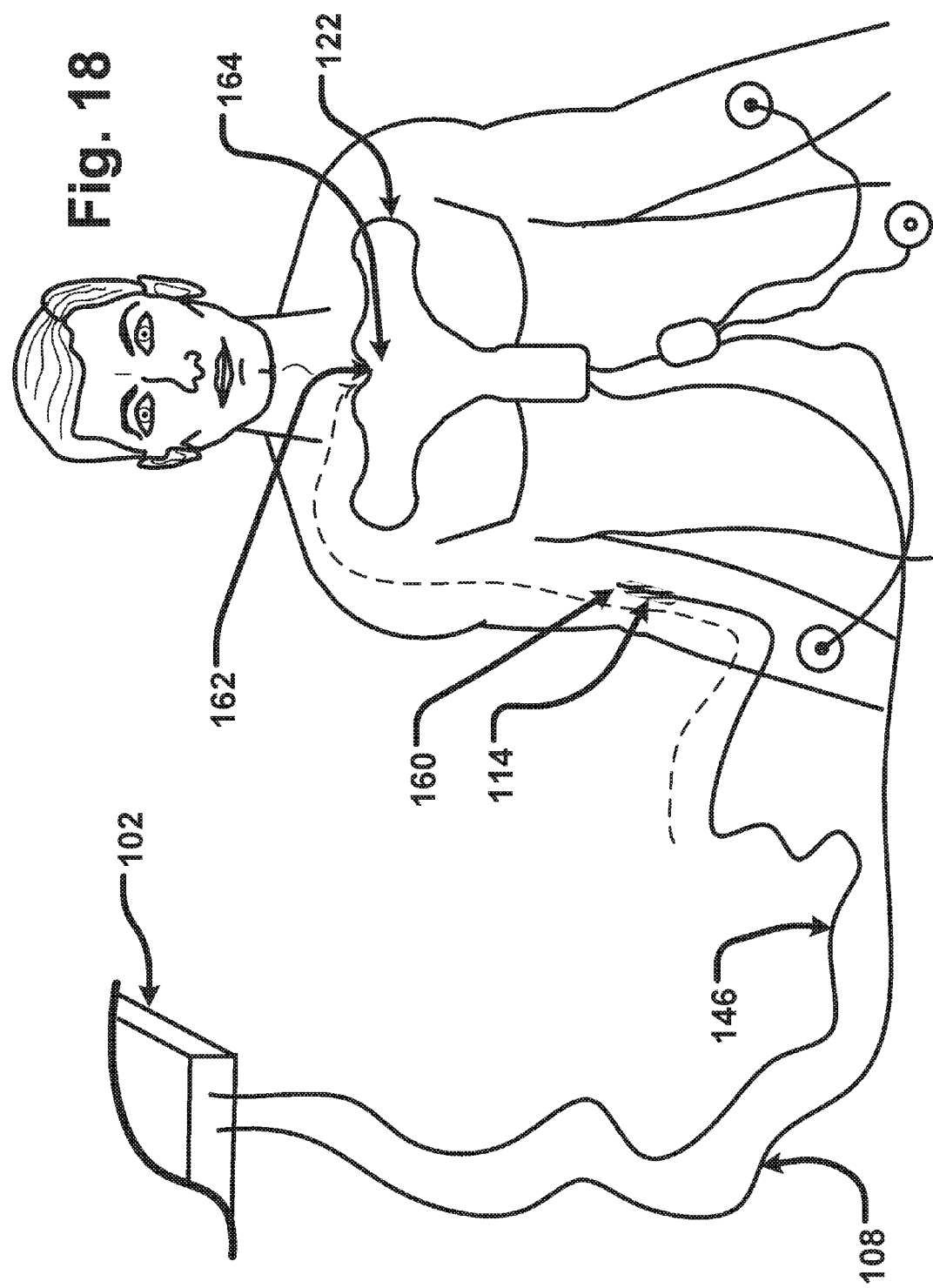

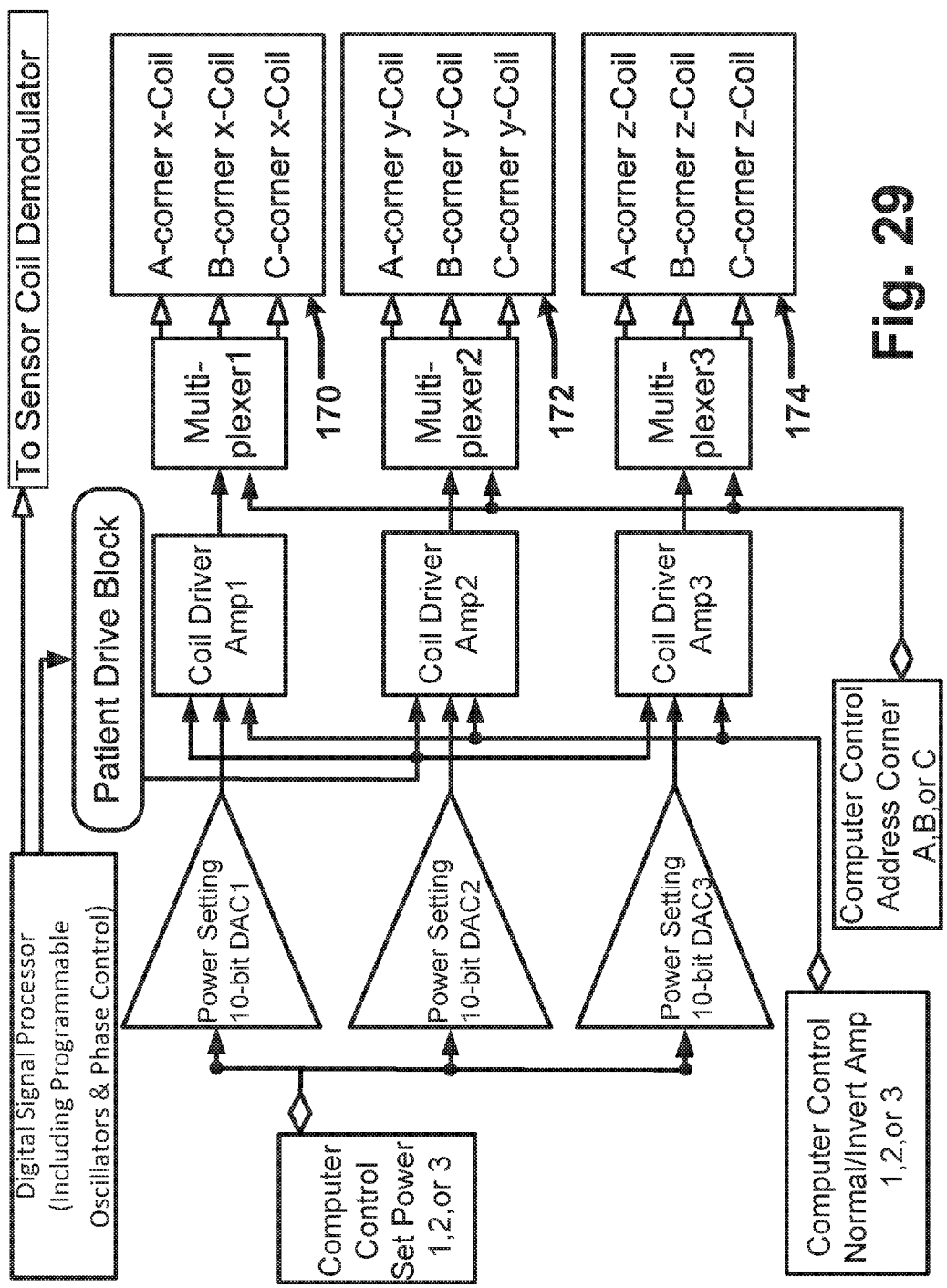

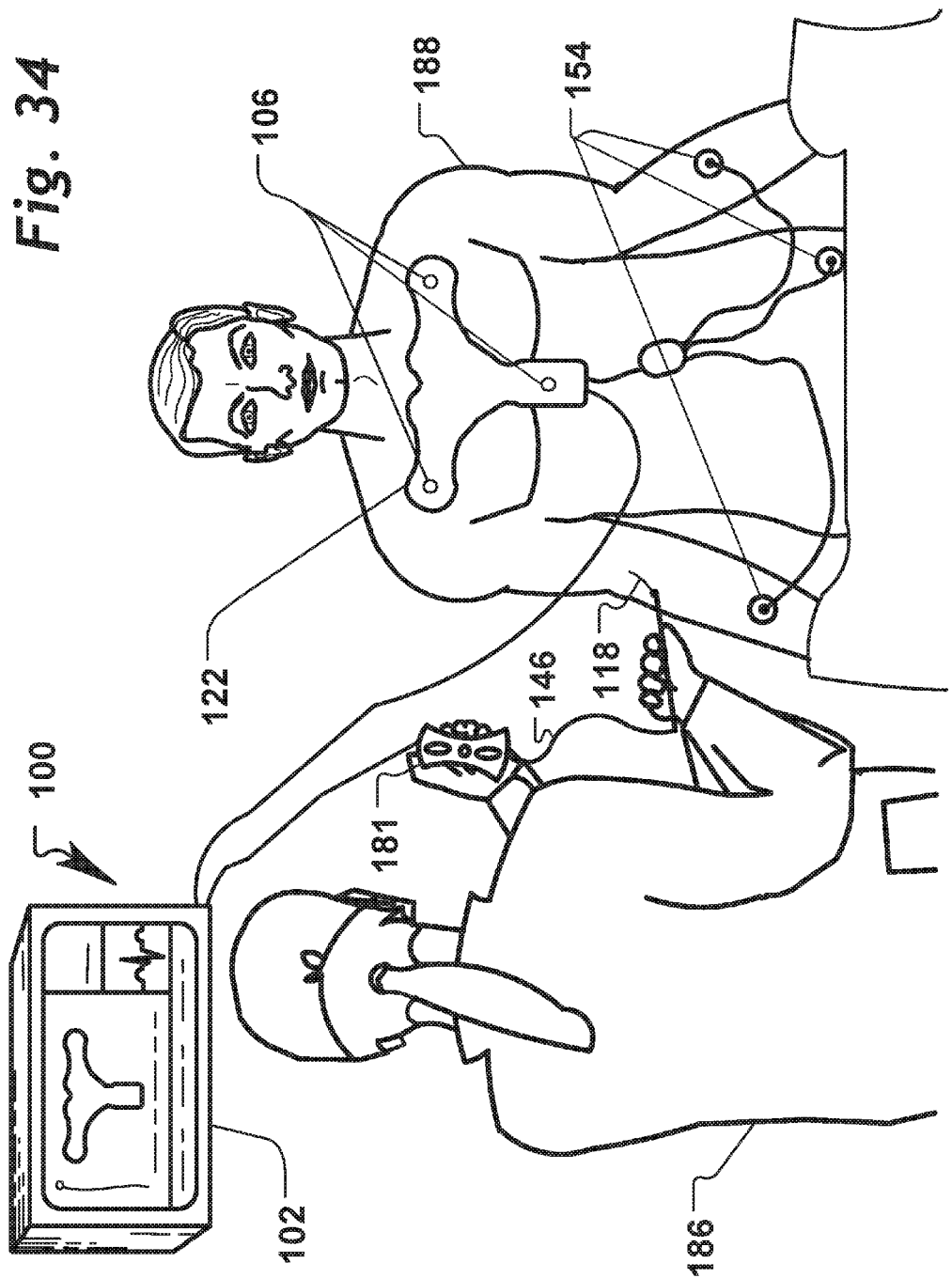

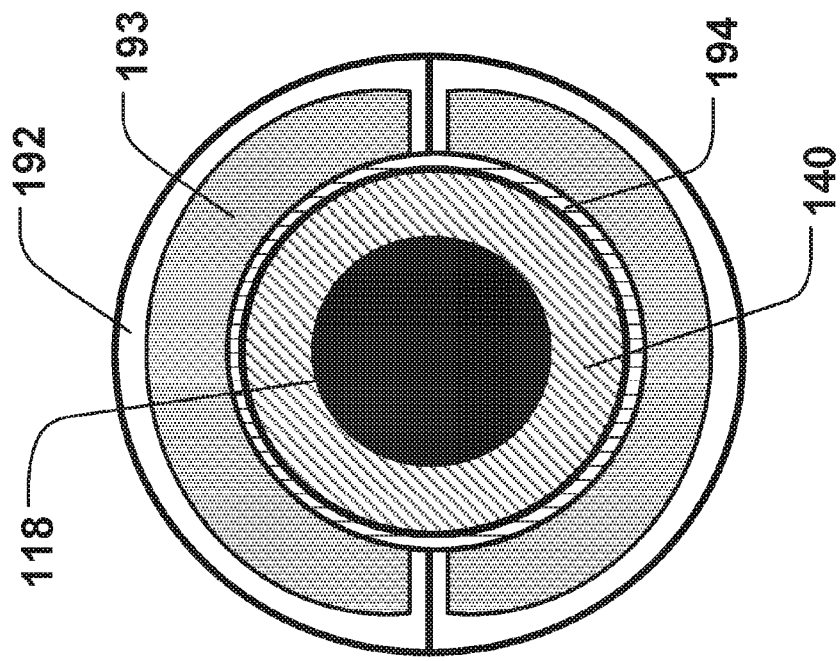
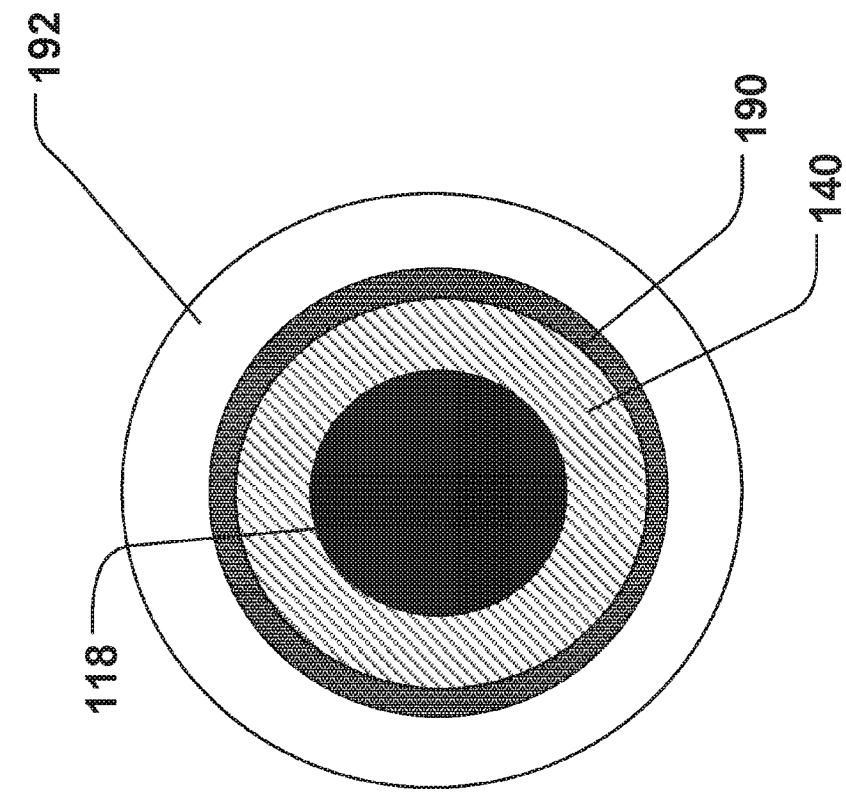
Fig. 35b
Fig. 35a

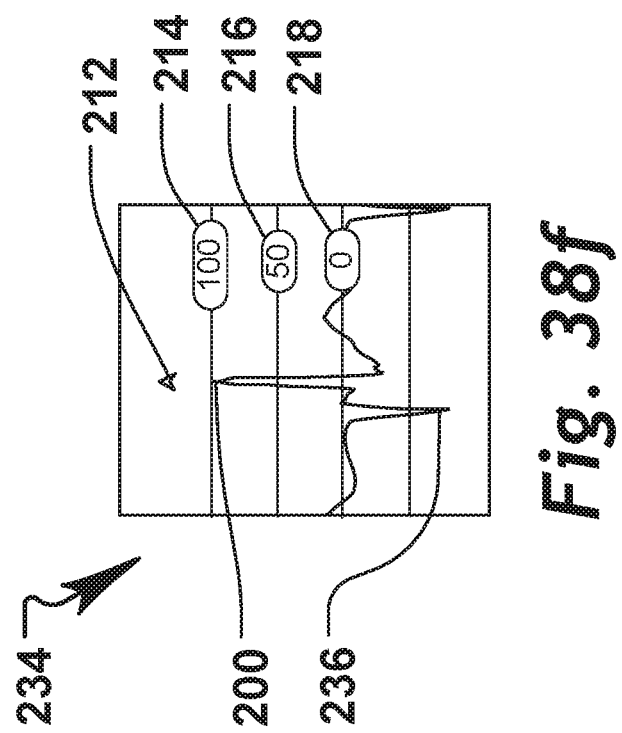
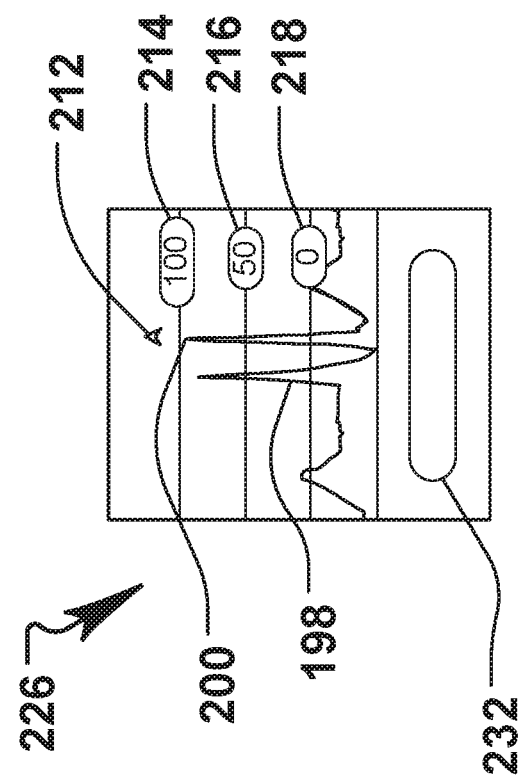
Fig. 38f
Fig. 38e

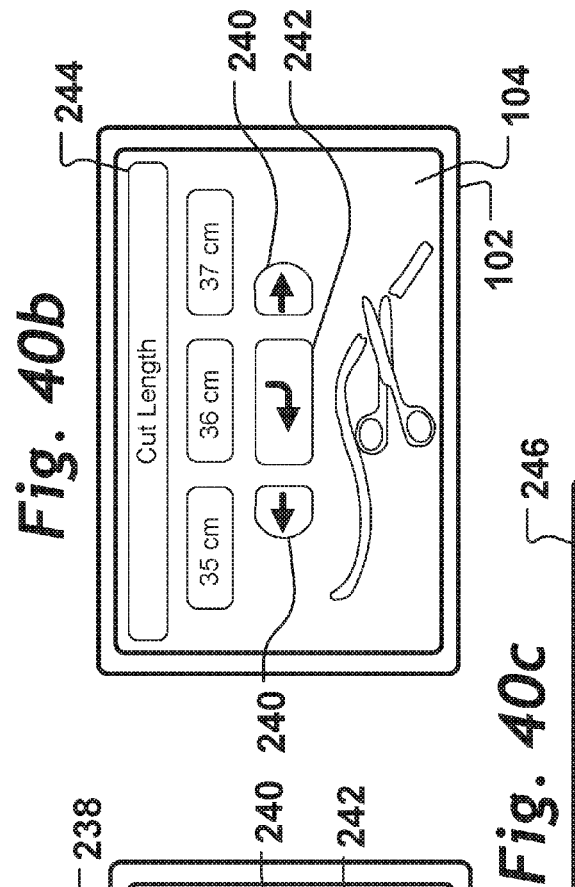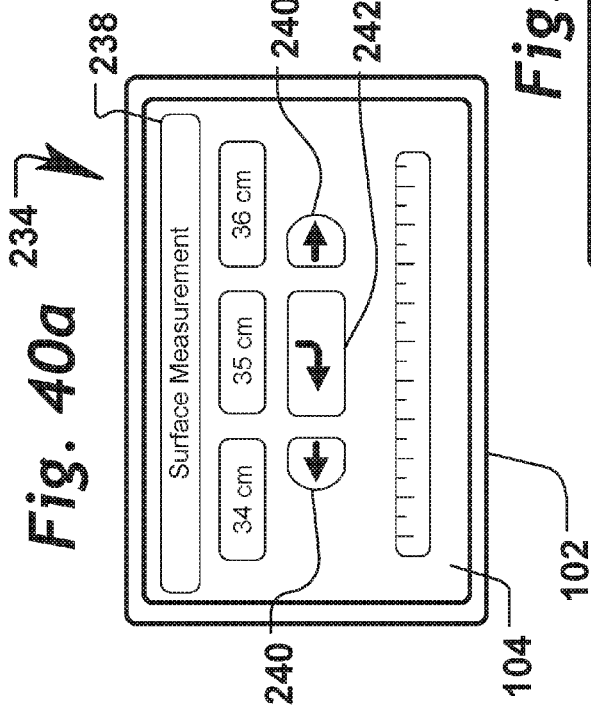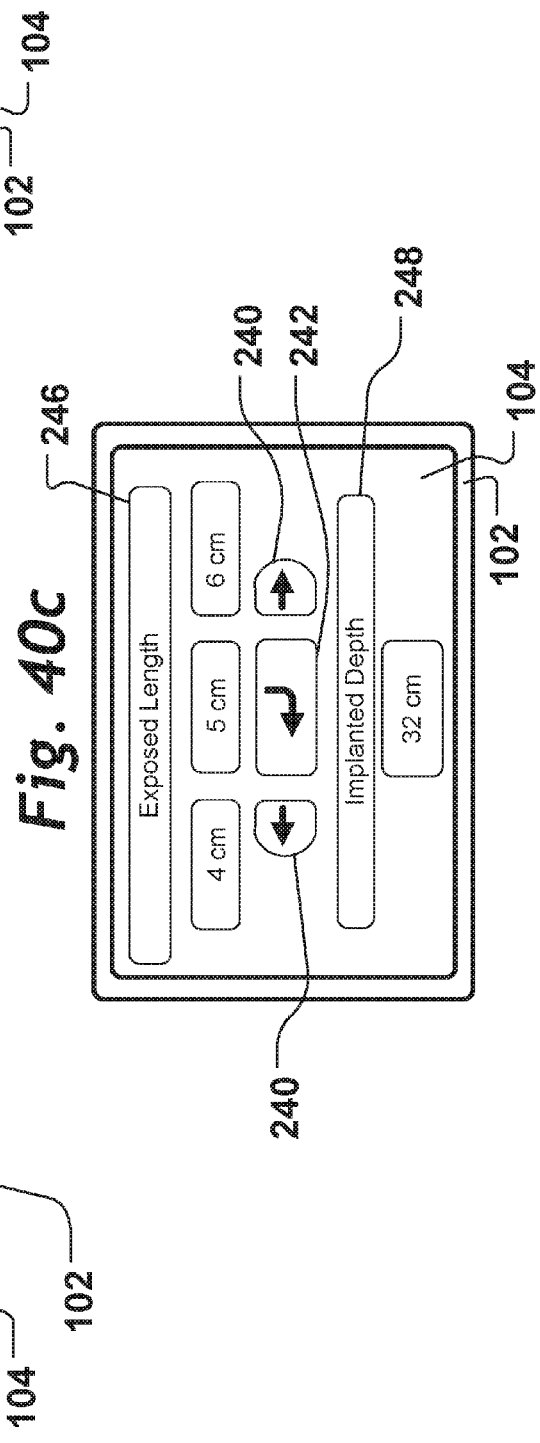

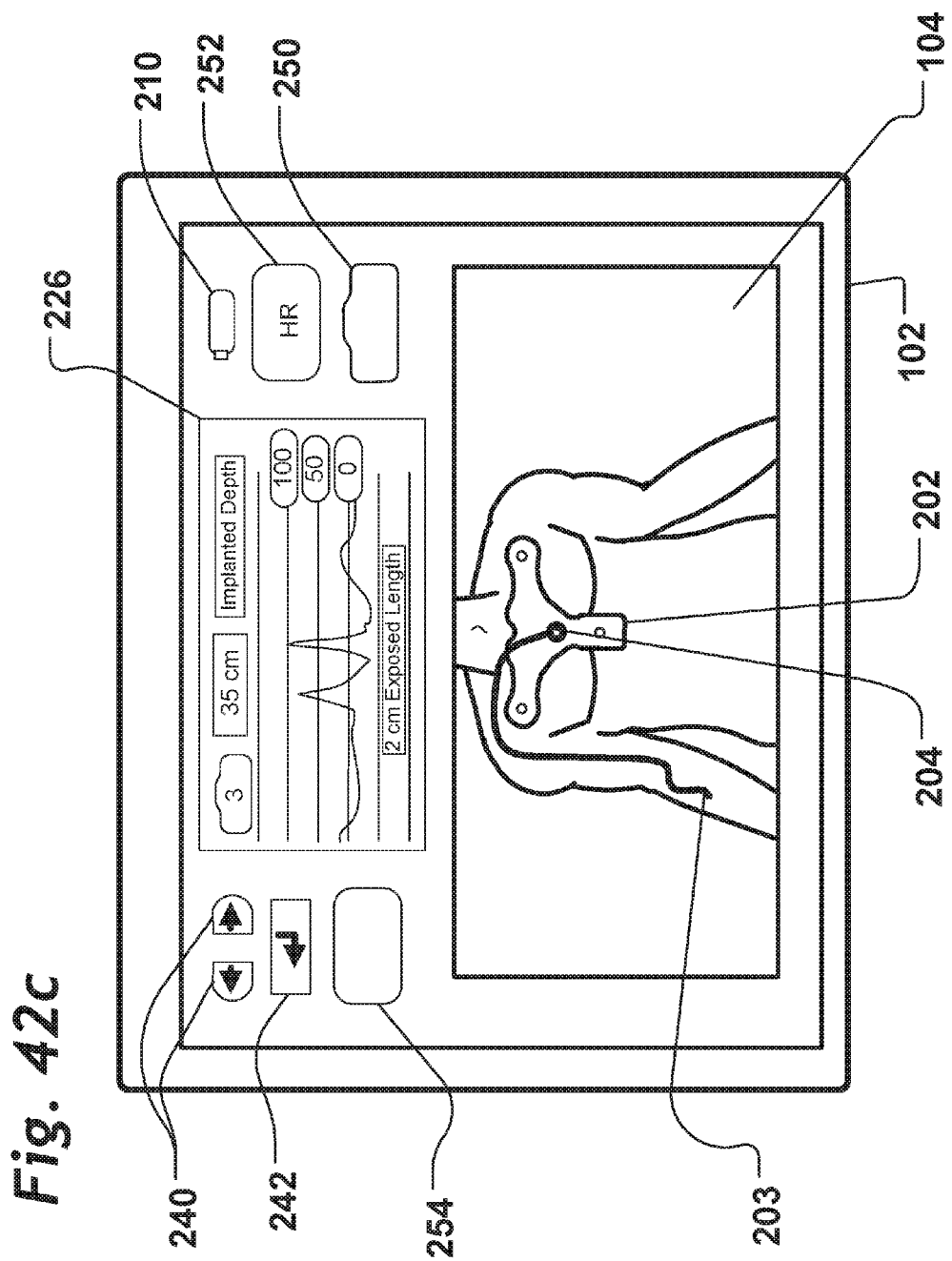

MEDICAL DEVICE POSITION LOCATION SYSTEMS, DEVICES AND METHODS

CROSS-REFERENCE TO RELATED APPLICATIONS

This application claims the benefit of U.S. Provisional Patent App. No. 62/154,687, filed Apr. 29, 2015, the disclosure of which is incorporated by reference in its entirety.

BACKGROUND

In medical care, the correct placement of a medical device such as a catheter or a guide wire in a patient has become increasingly important for a number of reasons. In the case of an infusion catheter, for one example, medications may need to be targeted to or for specific organs or areas of the body. In some instances, it may be important to place a catheter sufficiently near the heart where a particular blood flow rate ensures adequate dilution and mixing of infused fluids. Alternatively, a catheter or other internally-positioned medical device may simply need to be disposed in the right place to function, such as for example, an enteral feeding tube within the stomach. Use of a medical device position location and/or guidance system may thus provide for skilled and less skilled practitioners to more simply and/or accurately and reliably position a medical device such as a catheter without the use of an x-ray or additional ancillary procedures to confirm the location of the catheter or device. Additionally, the use of a medical device position location system additionally may provide for maintenance of the sterile field, a critical aspect in placing catheters or other internally positioned medical devices.

Accordingly, a variety of systems have been developed to attempt to indicate location or position of catheters or other medical devices disposed within the body of a patient. Relatively reliable location devices have made use of x-ray or fluoroscopy; however, these devices may expose the patient and/or caregiver to undesirable amounts of radiation. As a consequence, a variety of different systems have been attempted to more continuously and accurately indicate location of a catheter or other medical device with a goal of reducing and/or replacing the use of x-rays and as an alternative to fluoroscopy. However, such systems thus far developed still suffer from various drawbacks.

Electromagnetic catheter position location devices have been the subject of research and development. Some such locating systems have used an AC driven coil in the catheter tip with external sensor coils. A disadvantage of such a conventional catheter tip driven system has been the need for heavy or thick wires running into the catheter to carry necessary drive current to generate a sufficient electromagnetic signal for external sensors. This has precluded the use of such a system with smaller diameter catheters or other such smaller medical devices. Other position location systems have used a fixed magnet (or DC) on a catheter tip with external sensor coils. A significant disadvantage to such a fixed magnet location system has been that the magnet would necessarily be very small, and as such would generate a very small signal from the tip of the catheter. Additionally, DC magnet systems put an additional charge into the patient and as a consequence, other magnetic fields in the vicinity may create significant interference problems for such a system. Furthermore, the field of such a magnet drops off extremely quickly over distance and thus cannot be sensed more than a few inches deep into the patient's tissue. This results in some concern about the depth of the placement in the subject.

Some locating systems have made use of AC driven external coils and a sensor coil in the catheter tip. One such AC drive system has been described including driving two coils simultaneously; however, those respective coils were specified as having been driven at two different frequencies so that the coil drives are not additive and the sensor demodulates the two different frequencies as two independent values. Yet another AC drive system has been described driving two coils simultaneously in quadrature which simulates a single spinning coil; however, this system may only indicate the orientation of the sensor in the x-y plane and its relative position in that plane.

SUMMARY

Devices and/or methods configured for accurately determining position and/or location of a sensor coil within a subject by using a moveable sensor coil are disclosed. This sensor coil communicatively operates with, or responds to an array of drive coil sets of drive coils placed relative to a subject's body to allow detection and/or determining of positioning of the medical device in the subject's body. Each of the drive coil sets and the sensor coil may also be communicatively connected to or cooperative with one or more components which may include an external control and/or display whether in one or more boxes, the one or more components providing for one or more of respective selective driving of the drive coils of the sets of drive coils and/or for receiving response signals from the sensor coil. A determining component may also or alternatively also be included to determine medical device position using the response signals.

Methods, devices and systems may be provided for one or both of two- or three-dimensional location of the disposition of a sensor coil in a subject including: an array of electromagnetic drive coil sets, each set having two or three dimensionally oriented drive coils; a sensor coil being electromagnetically communicative with the array of electromagnetic drive coil sets; and, typically, a system controller or one or more like components communicative with and adapted to energize one or more of the electromagnetic coils in the array of electromagnetic drive coil sets, the energizing of the one or more of the electromagnetic coils including one or more of energizing the coils singly, or in pairs of x-y, and y-z, or x-z coils while measuring the response of the sensor coil; whereby a system hereof may then use the measurements of the responses of the sensor coil to calculate one or both of the location and orientation of the sensor coil relative to said drive coil sets.

The improved methods and systems for electro-magnetic tip location of patient catheters or other internally disposed medical devices described herein may be particularly useful for determining a more accurate z-axis location. The determination of the z-axis location allows for one or both more accuracy and certainty regarding the final placement of the catheter or medical device. An alternative embodiment incorporating a digital signal processor and alternative methodology, in some instances implemented in software architecture, may be used to determine that a determined and specified axis signal is approaching a null measured value. The sensor coil provides this response to the determining component of the system. The signal may then be estimated using information from the measured axes. For example, if the z-axis is approaching a sensed null value, the methodology is configured to use x-axis signal (x vector sum) and the measured y-axis signal (y vector sum) to calculate and substitute a position vector for the z-axis signal. The methodology may be operable to make the calculation and substitution when the measured response from the z-axis falls below a selected threshold. In turn, this provides a novel approach to using a triplet and/or quadruplet structure to determine the position in three dimensions of the sensor coil.

In some instances, a sensor coil may be disposed in association with a core wire in a stylet, catheter, or guidewire. The material, composition, and/or structure of the core wire may have important properties and characteristics to the position location system, device, and/or method. Selection of materials for the core wire may have considered properties that may affect characteristics such as flexibility, rigidness, resiliency, and bio-compatibility. The core wire may be comprised of a material selected from a group having substantially permeable magnetic materials.

These and still further aspects and advantages of the present subject matter are illustrative of those which may be achieved by these developments and are not intended to be exhaustive or limiting of the possible advantages which may be realized. Thus, these and other aspects and advantages of these present developments will be apparent from the description herein or may be learned from practicing the disclosure hereof, both as embodied herein and/or as modified in view of any variations that may be apparent to those skilled in the art. Thus, in addition to the exemplary aspects and embodiments described herein, further aspects and embodiments will become apparent by reference to and by study of the following description, including as will be readily discerned from the following detailed description of exemplary implementations hereof especially when read in conjunction with the accompanying drawings in which like parts bear like numerals throughout the several views.

BRIEF DESCRIPTION OF THE DRAWINGS

FIG. 4 is a detailed view of one four-axis drive coil set.
FIG. 5 is an exploded view of one embodiment of a four-axis drive coil set, including the patient drive coil block.
FIG. 6 is a view of one embodiment of a four-axis drive coil set, including the patient drive coil block
FIG. 7 is a detailed view of a sensor coil.
FIG. 8 is a detailed view of one embodiment of connection for the sensor coil to the determining component.
FIG. 12 is an illustration of magnetic vectors generated by a normal triplet coil drive.
FIG. 13 is an illustration of magnetic vectors generated by a quadruplet drive coil.
FIG. 14 is an illustration of magnetic vectors generated by a quadruplet drive coil.
FIG. 15 is an illustration of orthogonal magnetic vectors generated by a quadruplet drive coil arrangement.
FIG. 16 is a schematic overview of a present development hereof.
FIG. 17 is a schematic overview of another present development hereof.
FIG. 18 is a schematic overview of yet another present development hereof in which the present development is placed on a subject.
FIG. 29 is a schematic block diagram of a coil drive with full virtual x-y-z capability.
FIG. 34 is a schematic illustration of a stylet, catheter, or guidewire based medical system, in accordance with an embodiment of the present developments.
FIGS. 35a-35b are cross-sectional views of a distal portion of the apparatus according to one embodiment.
FIGS. 38a-38f are various views of the display of an exemplar of some present developments hereof.
FIGS. 40a-40c are various views of the displays of an exemplar of some present developments hereof.
FIGS. 42a-42d are various views of a display of an exemplar of some present developments hereof.

DETAILED DESCRIPTION

Figure 1:
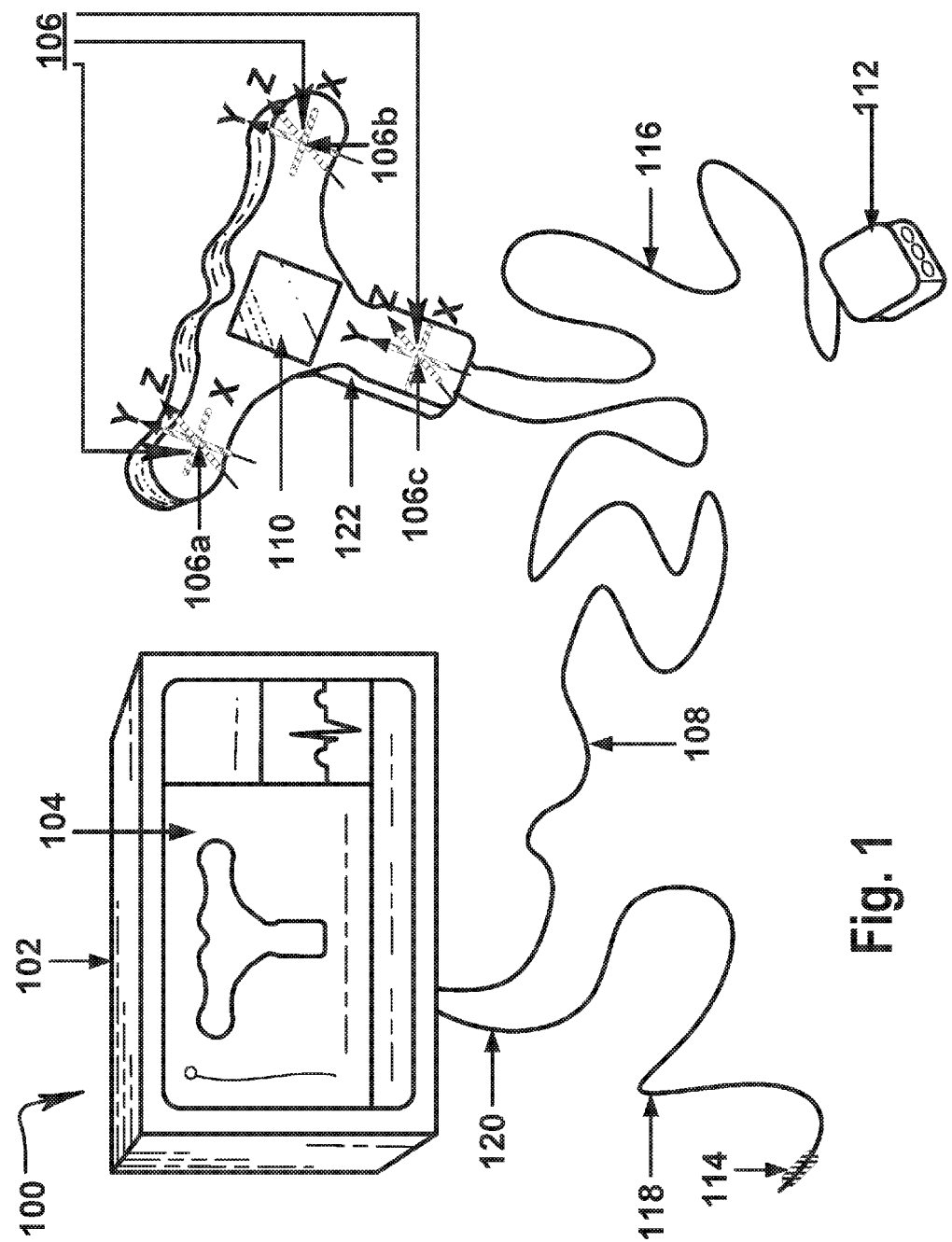
FIG. 1 is a schematic overview of an exemplar of some present developments hereof.

FIG. 1 provides an overview of an implementation of a medical device position location system 100 hereof. Shown in FIG. 1 are schematic representations of some alternative possible parts including a user control box 102 (which may be or include one or more components for operation of the other parts), and a patient drive coil block 122 with drive coil set 106, representative of any sets 106a, 106b, 106c, a guide wire or stylet with a sensor coil 114 and cable 118 (or other communication medium), and optional ECG connections 112, 116. A user control box 102 may be included though it might more appropriately be defined by the components thereof, a component for driving coils and a second component for receiving response signals, and/or optionally a determining component for determining position from the response signals. These components may be in or define an otherwise "black" box 102, or may otherwise be disparately disposed and merely operatively connected to each other by hard wires or wirelessly, or may alternatively be substantially physically indiscriminate one or more from each other though nevertheless operatively configured to achieve one or more of the driving, receiving and/or determining elements.

Schematically shown in FIG. 1, these components may be in and/or define the schematic box 102. Furthermore, a control box 102 whether of a black box nature or physically disposed may include other operative parts, and according to this implementation shown in FIG. 1, may contain a display such as a touch screen display 104, a single-board computer (SBC) (not separately shown in FIG. 1) for control and data processing, and/or a main interface board (also not separately shown in FIG. 1) which may connect to a drive block cable 108 and a medical device cable or member 118 (also sometimes referred to as a catheter, or guide wire or stylet cable 118). A patient drive coil block 122 may be connected via drive block cable 108 to the control box 102 (the drive coil block also sometimes being referred to as an emitter block, a patient block or merely a drive block). Coil drive electronics 110 and three drive coil sets 106a, 106b, 106c (also sometimes referred to as emitter coils, or x-y-z drive coils, or x-y-z', and z") are mounted in the drive block 122. The coil drive electronics 110 allow the SBC to selectively energize any drive coil axis 126, 128, 124 of a set 106 (see FIG. 2) or group of drive coil axes. A sensor coil 114 is, in this implementation, built on or within the tip of a medical device such as a small diameter biocompatible guide wire or stylet cable 118. The guide wire may then be placed in the patient and the catheter then threaded over this wire; or, alternatively, the stylet cable may then be inserted up to the distal end of a catheter before the catheter is placed in the patient. A two-conductor cable 120 may be used to connect the sensor coil of guide wire or stylet back to the user control box. In this embodiment, an ECG main cable 116 connects the ECG signal input receiver 112 to the circuitry associated with the drive block 122 or the coil drive electronics 110.

Figure 2:
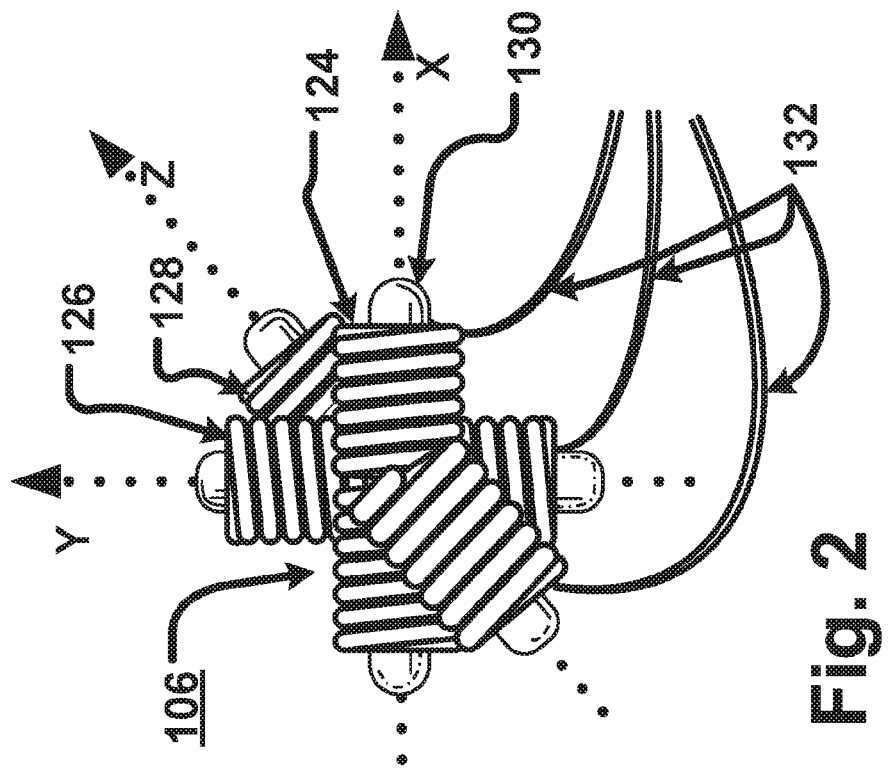
FIG. 2 is a detailed view of one three-axis drive coil set.

FIG. 2 shows a detailed drawing of a drive coil set 106 (representative of any of sets 106a, 106b, 106c). Here, the x-coil 124, the y-coil 126 and z-coil 128 each have a ferrite or ferrous core 130 to enhance the magnetic field generation. In an alternative embodiment, the coils, 124, 126, 128 each have an air core or no core material. This figure is only schematically representative of the construction of a drive coil; in actuality, each drive coil may have many windings (e.g. 100 turns) on the ferrite core and may be constructed as three (3) coil pairs to facilitate the intersection of the x, y, and z axes. Each coil here has a set of lead wires 132 to connect back to the multiplexers of the coil drive electronics 110.

Figure 3:
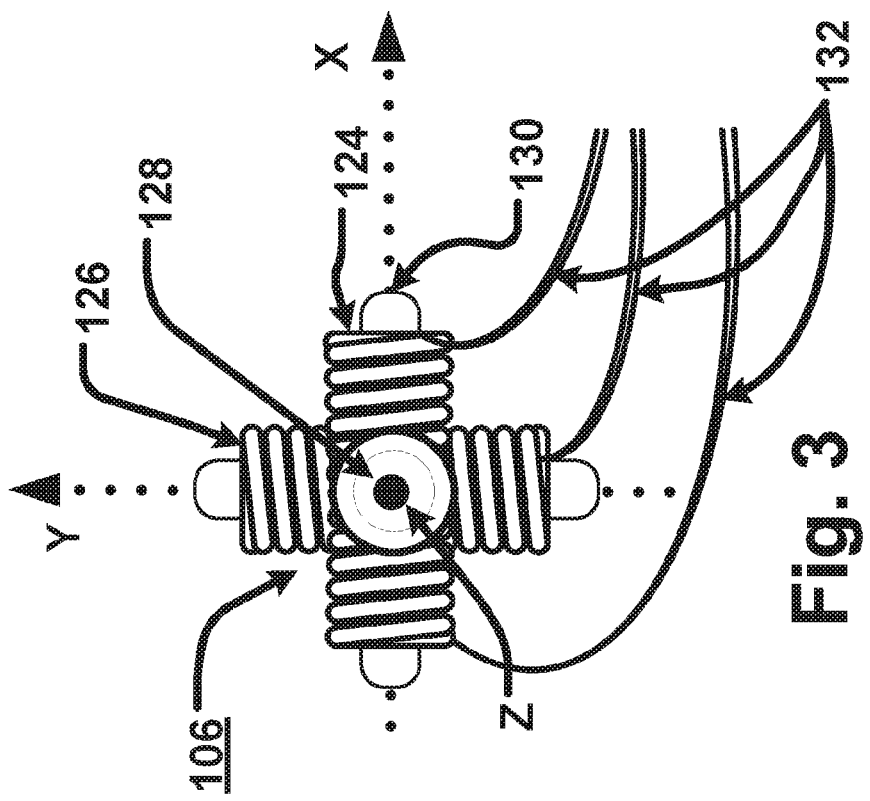
FIG. 3 is a plan view of one three-axis drive coil set.

FIG. 3 shows a plan view of a triplet drive coil set 106. In this representation the x-coil 124 and the y-coil 126 and the z-coil 128 are disposed relative to each other in an orthogonal arrangement. Each coil here has a set of lead wires 132 to connect back to the multiplexers of the coil drive electronics 110.

FIG. 4 shows a detailed drawing of an alternative quadruplet drive coil set 106 (representative of any sets 106a, 106b, 106c). Here, the x-coil 124, the y-coil 126, and the z'-coil 134, and z"-coil 136 (these latter two also referred to as the "z-coils") each have a ferrite or ferrous core 130 to enhance the magnetic field generation. Additionally, to further enhance the magnetic field generation z'-coil 134 and z"-coil 136 are arranged orthogonally in relation to each other, but non-orthogonally in relation to the x-coil 124 or y-coil 126. In this representation, the z'-coil 134 and the z"-coil 136 are oriented forty-five degrees off the standard arrangement of a z-axis, in a standard x-y-z coil array, also referred to as "off-axis". Alternatively described, the respective z-coils may be arranged in perpendicular to each other and geometrically oriented off axis at both a negative 45 degree angle and positive 45 degree angle away from the respective x, y axis. In such an arrangement, wherein the x-coil and y-coil are arranged orthogonally relative to each other and at least two other z-coils are arranged orthogonally relative to each other but the z-coils are "off-axis" or non-orthogonal relative to the x-coil and y-coil, the system is referenced as pseudo-orthogonal or in some instances as dually orthogonal. Where four drive coils are contained in one set the set is referred to as a quadruplet.

FIG. 5 shows an exploded two-dimensional schematic drawing of a quadruplet drive coil set. Here, the x-coil 124, the y-coil 126, and the z'-coil 134, and z"-coil 136 each may have a ferrite or ferrous core 130 to enhance the magnetic field generation. Additionally, to further enhance the magnetic field generation z'-coil 134 and z"-coil 136 are arranged orthogonally in relation to each other, but non-orthogonally in relation to the x-coil 124 or y-coil 126. In this representation, the z'-coil 134 and the z"-coil 136 are oriented forty-five degrees off the standard arrangement of a z-axis, in a standard x-y-z coil array. In some embodiments, the drive coil electronics 110 (circuit board) separates the z'-coil 134 and z"-coil 136 in to two distinct segments both above and below the imaginary plane created by the x-coil and y-coil arrangement. Optionally an additional aspect of this embodiment includes, at least one capacitor 131 operably associated with the drive coil to create an LC circuit.

FIG. 6 shows a three-dimensional schematic drawing of a quadruplet drive coil set. Here, the x-coil 124, the y-coil 126, and the z'-coil 134, and z"-coil 136 each may have an air core 133 to enhance the magnetic field generation. Additionally, to further enhance the magnetic field generation z'-coil 134 and z"-coil 136 are arranged orthogonally in relation to each other, but non-orthogonally in relation to the x-coil 124 or y-coil 126. In this representation, the z'-coil 134 and the z"-coil 136 are oriented forty-five degrees off the standard arrangement of a z-axis, in a standard x-y-z coil array. In some embodiments, the drive coil electronics 110 (circuit board) separates the z'-coil 134 and z"-coil 136 in to two distinct segments both above and below the imaginary plane created by the x-coil and y-coil arrangement. Optionally, at least one capacitor 131 is operably associated with the drive coil to create an LC circuit for the inductance, engergizing, or driving of the electromagnetic coils.

FIG. 7 shows a detailed view of an exemplar medical device; e.g., a guide wire or stylet sensor coil. The sensor coil 114 may be any suitable gauge (e.g., but not limited to, a very fine gauge (e.g. 0.001" diameter) wire wound around a ferrous core wire 138. In some instances, the sensor coil 114 and sensor coil lead wires may be insulated. In some embodiments the core wire 138 is composed of an alloy that affects a number of functional characteristics of the sensor coil (e.g. flexibility, semi-permeable magnetic properties, and conductivity). This figure is schematically illustrative only of the sensor coil; here, the sensor coil is approximately 400 turns in single layer, but may be any suitable turns per length, e.g., 50-1000, or any range or value therein, e.g., 100, 200, 300, 350, 400, 450, 500, 550, 600, 650, 700, and the like. The sensor coil lead wires 142 connect back through a cable to the patient isolated portion of the main interface board. An electrical insulator 140 may be used to provide a protective sleeve and/or coating for the assembly. An alternative construction may optionally include two or more sensor coils wrapped around the ferrous core wire 138. An additional sensor coil would likely need additional lead wires to connect back to the patient isolated portion of the main interface board. In an optional ECG version of a catheter location system, the tip of the ferrous, conductive core wire 138 may be polished smooth and may remain uncoated and/or unsheathed and may provide an electrical signal as an ECG lead from within the catheter.

In an alternative representation, the ECG version of the sensor coil location system (e.g., FIG. 8) the conductive core wire 138 is operably connected to an electrical connector or jack 144 (in this alternative embodiment the connection component may be a 3.5 mm female stereo plug 148, in one example) which may provide the output and signal to the patient isolated portion of the main interface board. In such a version, the guide wire or stylet sensor connection may be accomplished with three wires, two (2) for the coil sensor and one (1) for the ECG, through a cable 146 to the patient isolated portion of the main interface board in the user control box 102 (not separately shown in FIG. 8).

Figure 11:
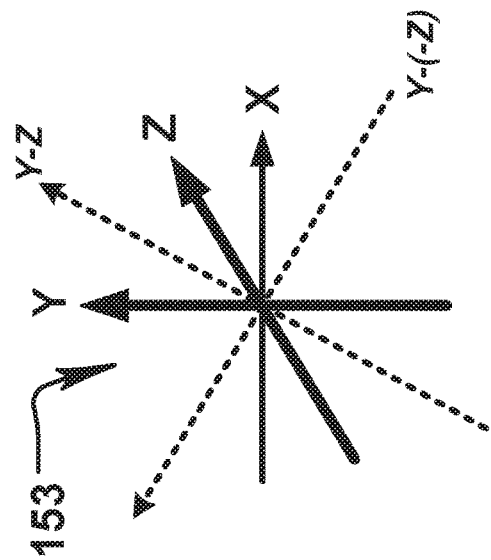
FIG. 11 is an illustration of orthogonal magnetic vectors generated by a y-z virtual drive.
Figure 10:
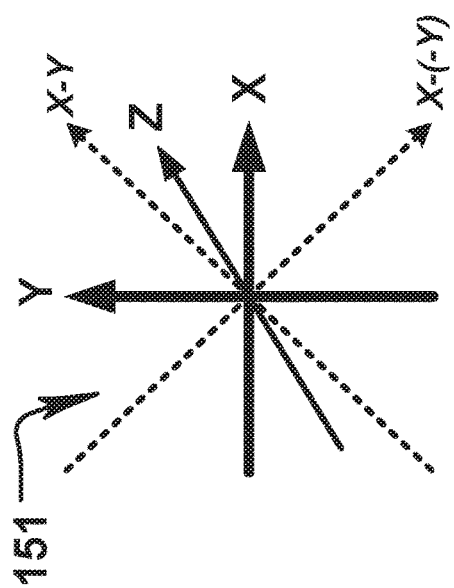
FIG. 10 is an illustration of orthogonal magnetic vectors generated by an x-y virtual drive.
Figure 9:
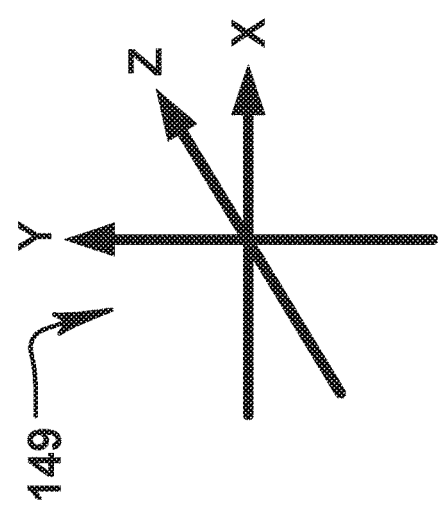
FIG. 9 is an illustration of magnetic vectors generated by a normal triplet coil drive.

FIGS. 9, 10 and 11 illustrate an optional version of the operation of a triplet normal-drive and virtual-drive drive coil set. FIG. 9 shows magnetic vectors x, y, and z generated by normal coil 149 driving of the x-axis coil 124, the y-axis coil 126 and z-axis coil 128 (as shown in FIG. 2). FIG. 10 shows the virtual magnetic vector x-y 151 generated by simultaneously driving the x-axis coil 124 and the y-axis coil 126 (as shown in FIG. 2) and when both are driven at the same power, the vector is forty-five degrees between the x and y axes. The virtual magnetic vector x-(−y) generated by simultaneously driving the x-axis coil 124 and the phase-inverted, y-axis coil 126 (as shown in FIG. 2) and when both are driven at the same power, the vector is minus forty-five degrees between the x and −y axes. If a digital to analog converter (DAC) is added to control power to the x-axis drive and another DAC added to control power of y-axis drive, then it is possible to point the virtual axis to any angle from 0 to 360 degrees between x and y. For example, if x-axis power DAC is maximum and y-axis power DAC is $\frac{1}{4}^{th}$ (one quarter) of maximum then the vector sum of x-y drive yields a virtual axis of approximately fourteen degrees between the x and y axes. FIG. 11 shows a virtual magnetic vector y-z 153 generated by simultaneously driving the z-axis coil 124 and the y-axis coil 126 (as shown in FIG. 2); and a virtual magnetic vector z-(−y) generated by simultaneously driving the z-axis coil 124 and a phase-inverted, y-axis coil 126 (as shown in FIG. 2). These figures illustrate one optional form of virtual drive (e.g., see FIG. 25), and it is possible to point a virtual magnet vector to any polar coordinate by simultaneously driving x, y, and z coils at independent power levels (e.g., see FIG. 29).

FIGS. 12, 13, 14, and 15 illustrate an optional version of the operation of a quadruplet normal-drive and virtual-drive drive coil set. FIG. 12 shows magnetic vectors x, y, and z generated by normal coil 149 driving of the x-axis coil 124, the y-axis coil 126 and z-axis coil 128 (as shown in FIG. 2; FIG. 12 provides a reference for the orientation of the pseudo-orthogonal orientation of z'-axis and z"-axis). FIG. 13 shows the x, y, z' and z" magnetic vectors 155 and shows what would be the virtual z vector formed from the z' and z" magnetic vectors. It is noted that relative powering of the z'-coil and z"-coil may be used to generate a virtual z vector as depicted in FIG. 13, but also other virtual magnetic vectors from the x, y, z', and z" normal-drive coils. FIG. 14 shows the discrete x, y, z' and z" magnetic vectors 157 super-imposed on the quadruplet coil set such as those shown in FIGS. 4, 5, and 6. FIG. 15 shows the four virtual magnetic vectors of x-y and z'-z" 159 generated by simultaneously driving the x-axis coil 124 and the y-axis coil 126 (as shown in FIG. 2) and by simultaneously driving the z' and z" axis coils. In this alternative and when both x-axis and y-axis are driven at the same power, the vector is forty-five degrees between the x and y axes. The virtual magnetic vector x-(−y) generated by simultaneously driving the x-axis coil 124 and the phase-inverted, y-axis coil 126 (as shown in FIG. 2) and when both are driven at the same power, the vector is minus forty-five degrees between the x and −y axes. If a digital to analog converter (DAC) is added to control power to the x-axis drive and another DAC added to control power of y-axis drive, then it is possible to point the virtual axis to any angle from 0 to 360 degrees between x and y. For example, if x-axis power DAC is maximum and y-axis power DAC is $\frac{1}{4}^{th}$ (one quarter) of maximum then the vector sum of x-y drive yields a virtual axis of approximately fourteen degrees between the x and y axes. FIG. 15 further shows a virtual magnetic vector z'-z" generated by simultaneously driving the z'-axis coil 134 and the z"-axis coil 136 (as shown in FIG. 4); and a virtual magnetic vector z'-(−z") generated by simultaneously driving the z'-axis coil 134 and a phase-inverted, z"-axis coil 136 (as shown in FIG. 2). These figures illustrate one optional form of virtual drive (e.g., see FIG. 26), and it is possible to point a virtual magnet vector to any polar coordinate by simultaneously driving x, y, and z coils or in some cases z'-coil and z"-coil at independent power levels (e.g., see FIG. 31).

Furthermore, FIG. 16 provides a schematic diagram of a medical device position location system with an electrocardiograph (ECG) measurement. This is similar to the FIG. 1 implementation with the addition of three ECG leads. The user control box 102 connects through a main interface board 158 to the drive block cable 108 and guide wire or stylet cable 146. The patient drive block 122 may be connected via drive block cable 108. Three isolated ECG leads 152 communicate signals to the control box 102. The coil drive electronics 110 and three x-y-z drive coil sets 106a, 106b, 106c may be mounted in the drive block 122. The coil drive electronics 110 allow the single board controller 166 (SBC) to selectively energize any drive coil axis 126, 128, 124 (FIG. 2) or group of drive coil axes. In this embodiment, three ECG pads 154 may be placed on the patient and connected by ECG lead wires 152 to an ECG signal input receiver 112 that connects an ECG main cable 116 to the drive block 122. These two, three, or more ECG inputs together with the one ECG from the catheter may provide at least a three-lead ECG measurement system (e.g., see FIGS. 23 and 24). The guide wire or stylet sensor 114 here is built onto a small diameter biocompatible conductive-tip guide wire or stylet cable 146 which is inserted into a catheter before (stylet) or after (guide wire) the catheter is placed in the patient. A drive block cable 108 connects the patient drive coil block 122 to the user control box 102. In alternative embodiments, the user control box houses the main interface board 158, the single board controller 166, and in some instances isolates the power supply connections. In some embodiments (not shown in the figures), the ECG signal input receiver 112 may be operably housed, contained, and/or connected to either the drive block 122 or the user control box 102. Moreover, in alternative embodiments, the ECG pads 154 may connect wirelessly to at least one or more selected from the group of: the ECG signal input receiver 112, the driver block 122, or the user control box 102. In these embodiments, the ECG measurement may be displayed on the user control box 102 and a touch screen 104 may be used in association with a graphical user interface adapted to display the location of the sensor coil 114 in relation to the patient drive block 122 over time. In some embodiments, the ECG measurement may be displayed solely on the touch screen display 104. In alternative non-limiting embodiments, the ECG measurement may be displayed simultaneously with the location of the sensor coil 114. In yet another non-limiting embodiment, the sensor coil location and orientation may be displayed on the display 104, without additional information related to the ECG measurement data.

FIG. 17 provides a schematic diagram of a medical device position location system with an optional electrocardiograph (ECG) measurement wherein the drive coil array contains 12 drive coils arranged and oriented as depicted in FIGS. 13, 14 and 15. The user control box 102 connects through a main interface board to the drive block cable 108 and guide wire or stylet cable 146. The patient drive block 122 may be connected via drive block cable 108. Three isolated ECG leads 152 communicate signals to the control box 102. The coil drive electronics 110 and three x-y-z drive coil sets 106*a*, 106*b*, 106*c* may be mounted in the drive block 122. The coil drive electronics 110 allow the single board controller (SBC) to selectively energize any drive coil axis 126, 124, 134, 136 (FIG. 4) or group of drive coil axes. Two, or three or more ECG pads 154 may be placed on the patient and connected by ECG lead wires 152 to the drive block 122. The guide wire or sensor coil 114 here is built onto a small diameter biocompatible conductive-tip guide wire or stylet cable 146 which is inserted into a catheter before (stylet) or after (guide wire) the catheter is placed in the patient. A drive block cable 108 connects the guide wire or stylet sensor coil and optionally one ECG lead back to the user control box 102. FIG. 17 shows the patient drive coil block 122 may have two or more ECG pads added which connect through a cable 152 to the patient isolated portion of the main interface board. These two, three, or more ECG inputs may together with the one ECG from the catheter provide at least a three-lead ECG measurement system.

FIG. 18 is an overall schematic diagram of a medical device position location system in use relative to a subject or patient. This figure illustrates connections between a user control box 102 and a sensing guide wire or stylet 114 and a patient drive block 122. The control box 102 may include an integrated, separated, or remote user display and/or interface. Each of these components may include cables or connectors or wireless communications for one or more of a coil interface, a power supply, a serial interface, a control interface, a status interface, an ECG interface or lead, an oscillator interface, a processor interface, a computer interface, a data interface, a network interface (cable or wireless), an internet interface, a video interface, a touch-screen interface, an SBC control or power interface, a board interface, a sensor interface, an isolator interface, and/or the like as described herein or as known in the art. One or more of these cables or connectors may attach to the patient drive block 122 or any component thereof. This figure further demonstrates one possible insertion point 160 into the subject. Optionally, in this instance the device may be inserted in a peripheral vasculature of the subject, specifically the right arm of the patient. Optionally, the system may be configured for use at other insertion sites on the patient's body as may be determined by either medical staff and/or the desired application and use of the system. Additionally, FIG. 18 shows placement of this embodiment of the patient drive block where the designated drive block notch 162 is aligned with or near the sternal notch of the subject 164. In alternative embodiments, the system could optionally be implemented for use among a number of different entry or insertion points (e.g. peripheral insertion (cephalic vein), midline insertion (basilic vein), central venous insertion (interjugular vein), chest insertion (subclavian vein or axillary vein) or groin (femoral vein)). Moreover, in yet another implementation, the system could be used for placement at insertion sites for nephrostomy or kidney dialysis. The patient drive block 122 may be adapted to different shapes, configurations, or arrangements that may align with anatomical features of the subject. In alternative non-limiting embodiments, the designated drive block notch may be adapted to be one or more of a notch, an extrusion, a marked portion, or an alignment hole. The patient drive block may be disposed or enclosed in a patient drive block housing made from a material suitable for clinical applications such as molded plastic or other materials known in the art. The housing may provide a protective shell, casing or housing for the electronics of the array of drive coils. These embodiments of different shaped shells, casings, or housings may assist in the medical personnel placing the patient drive block on the subject aligned with anatomical features of the subject.

Figure 19:
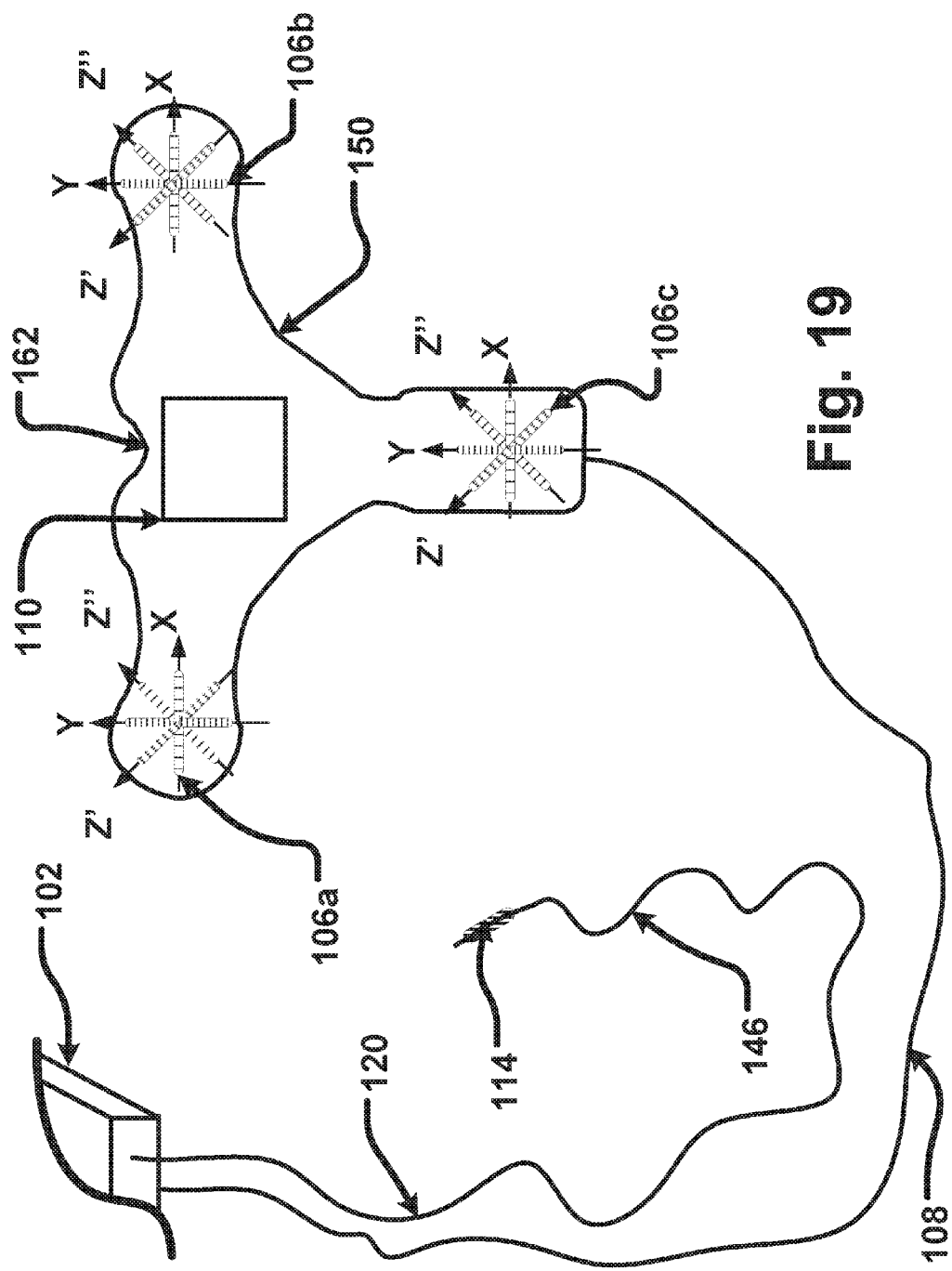
FIG. 19 is a schematic block diagram of a present development hereof.

FIG. 19 provides a schematic diagram of a medical device position location system wherein the drive coil array contains 12 drive coils. In this embodiment, optional ECG measurement components may be disconnected from the system entirely or not included in the patient drive block 150. In this non-limiting approach the coils are arranged and oriented as depicted in FIGS. 13, 14 and 15. The user control box 102 connects through a main interface board to the drive block cable 108 and guide wire or stylet cable 146. The patient drive block 150 may be connected via drive block cable 108. The coil drive electronics 110 and three x-y-z drive coil sets 106*a*, 106*b*, 106*c* may be mounted in the drive block 150. In this embodiment, the patient drive block 150 may not include two or more ECG leads with patient isolation. The coil drive electronics 110 allow the single board controller (SBC) to selectively energize any drive coil axis 126, 124, 134, 136 (FIG. 4) or group of drive coil axes. The guide wire or sensor coil 114 here is built onto a small diameter biocompatible conductive-tip guide wire or stylet cable 146 which is inserted into a catheter before (stylet) or after (guide wire) the catheter is placed in the patient. A drive block cable 108 connects the guide wire or stylet sensor coil to the user control box 102. It should be noted that, FIG. 16 shows an alternative embodiment wherein the patient drive coil block 122 may have two or more ECG pads added which connect through a cable 152 to the patient isolated portion of the main interface board. FIG. 19, is provided to show that the system 100 may be adapted to use a patient drive block 122 or a patient drive block 150, the patient drive block 150 being a non-limiting aspect not adapted to provide ECG measurements.

Figure 20:
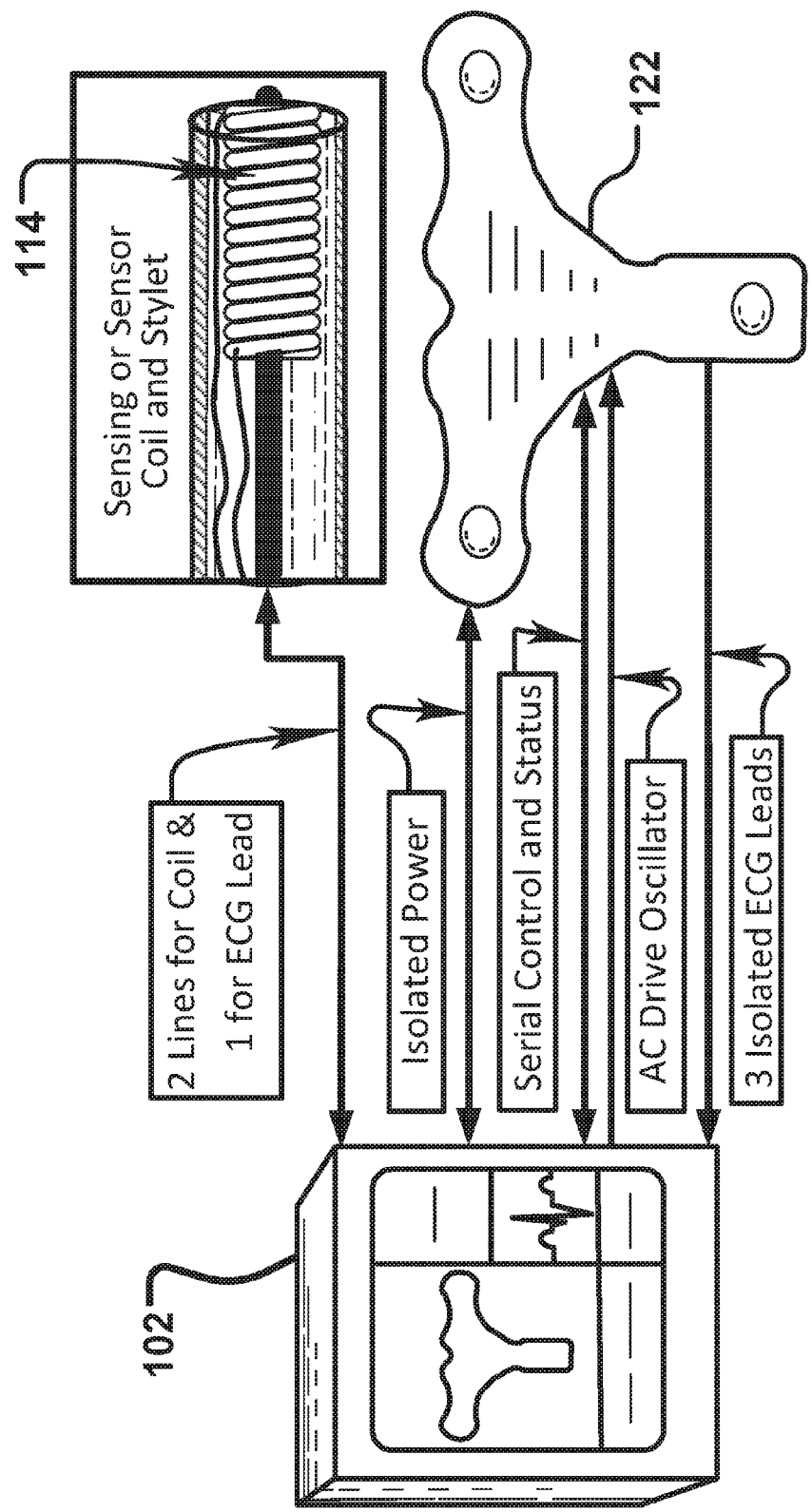
FIG. 20 is a schematic block diagram of a present development hereof.

FIG. 20 is another schematic diagram of a medical device position location system. This figure illustrates connections between a user control box 102 (again, box 102 may be merely a schematic "black" box or may be physically disposed, the one or more components thereof including one or more of a first component for driving the coils, a second component for receiving signals and a determining component for determining location; noting also that the one or more components may be physically disparate from each other and merely operatively connected, or may alternatively be substantially physically indiscriminate one or more from each other though nevertheless operatively configured to achieve one or more of the driving, receiving, measuring, and/or determining elements) and a sensing guide wire or stylet 114 and a patient drive block 122, 150. The control box 102 may include an integrated, separated, or remote user display and/or interface. Each of these components may include cables or connectors or wireless for one or more of a coil interface, a power supply, a serial interface, a control interface, a status interface, an optional ECG interface or lead, an oscillator interface, a processor interface, a computer interface, a data interface, a network interface (cable or wireless), an internet interface, a video interface, a touch-screen interface, an SBC control or power interface, a board interface, a sensor interface, an isolator interface, and/or the like as described herein or as known in the art. One or more of these cables or connectors or wireless may operatively attach to the patient drive block 122 or any component thereof. In this embodiment the power connection is isolated as further depicted in FIG. 22. Note, the power, serial control and status and ECG may be optional; i.e., these may be part hereof or discrete functionalities; whereas components, whether in or disparate from a box 102 (black box or otherwise) for driving coil operation, receiving sensor coil signals, and/or determining location would be preferred, though again, these may be together physically, perhaps indiscriminately, or may be disparate physically and merely operatively connected as needed or desired.

Figure 21:
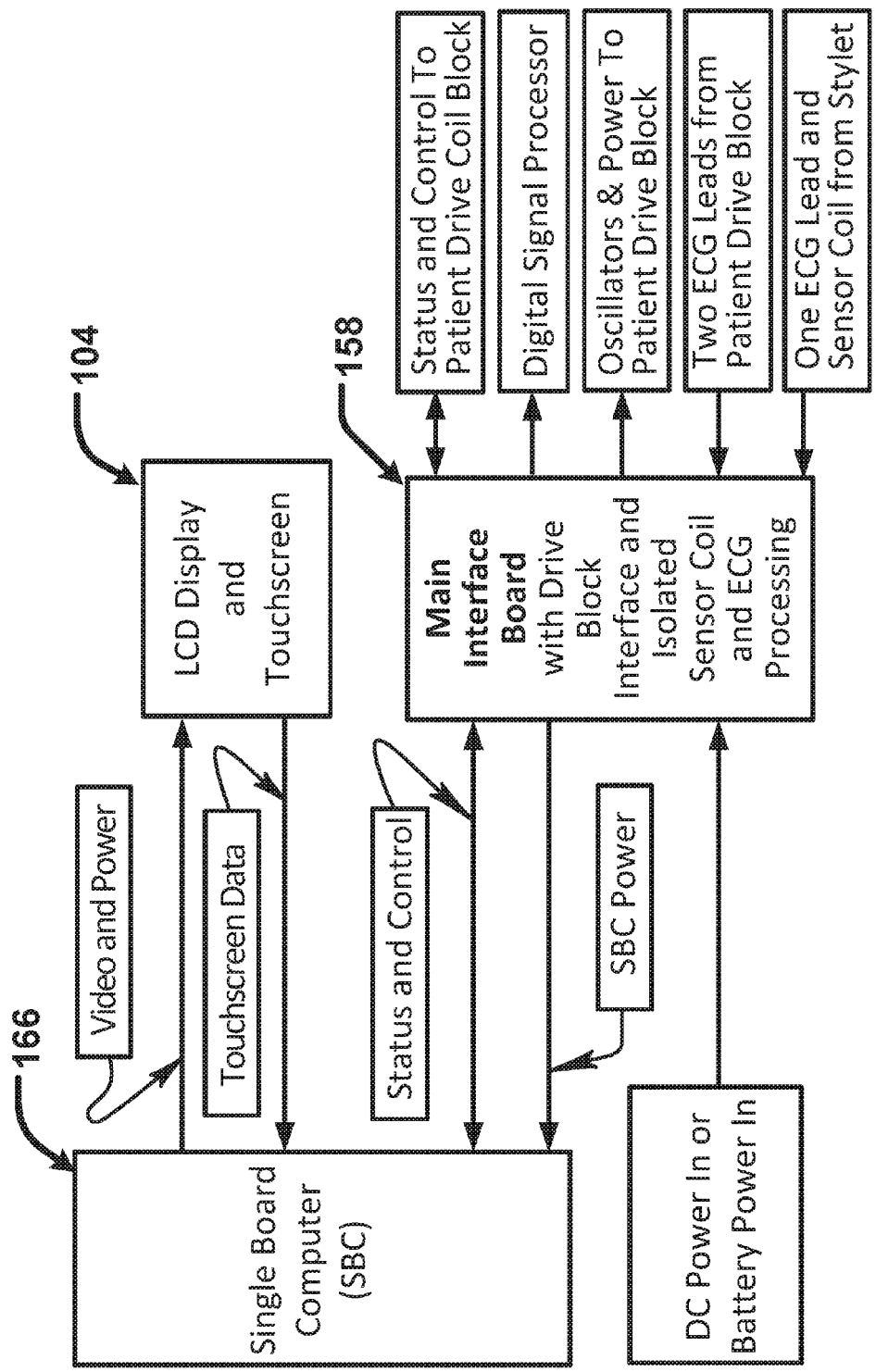
FIG. 21 is a further schematic block diagram of an exemplar display/interface and user control box as may be used herein.

FIG. 21 is a block diagram of an exemplar user control box 102 which in this implementation may include a computer 166, which in a number of examples may include a digital signal processor (aka DSP), a display 104, optionally either or both LCD with or without touch-screen capabilities, and a main interface board 158. Each of these components may include cables or connectors or wireless for one or more of a coil interface, a power supply, a serial interface, a control interface, a status interface, an optional ECG interface or lead, an oscillator interface, a processor interface, a computer interface, a data interface, a network interface (cable or wireless), an internet interface, a video interface, a touch-screen interface, a computer control or power interface, a board interface, a sensor interface, an isolator interface, a digital signal processor, a zero insertion force (ZIF) socket, and/or the like as described herein or as known in the art.

Figure 22:
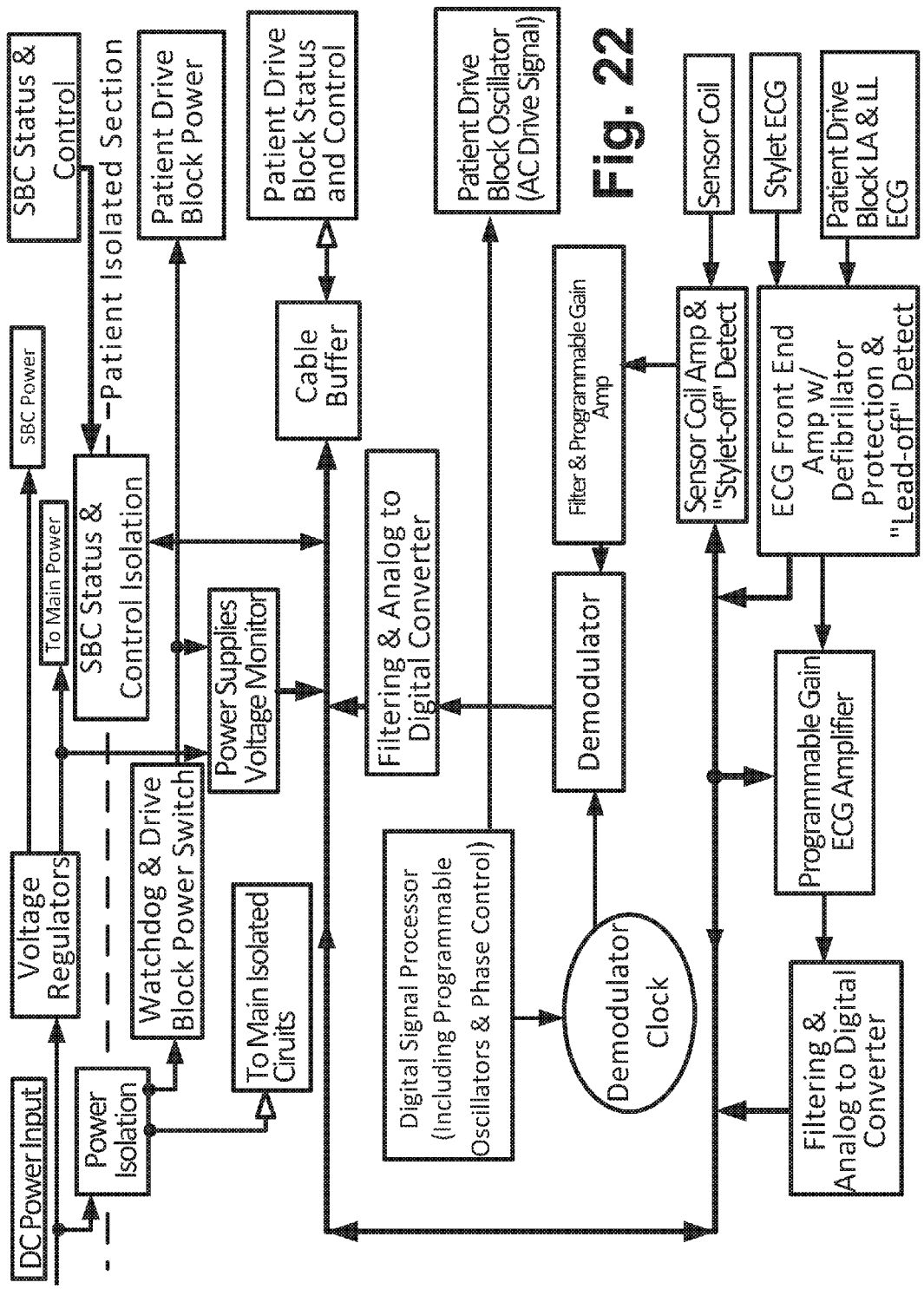
FIG. 22 is still a further schematic block diagram of a main interface board in a user control box as may be used herein.

FIG. 22 provides a block diagram of a main interface board 158 (FIG. 20), associated circuitry, and shows a patient isolated section which connects to a guide wire or stylet cable 120 and optional ECG leads from a patient drive block 122. The remainder of the circuitry controls power/interface to a patient drive block 122 and power to a single board computer 156, which may include one or more of a voltage regulator, a watchdog switch, a drive switch, a power isolator, a voltage monitor, a cable buffer, a filter, an analog to digital converter, a digital signal processor, a demodulator clock, a phase adjuster, a demodulator, a signal filter, a programmable gain amplifier, a coil isolator, a coil sensor coil amplifier, a detector, memory, flash memory, a multiplexor, a polarity inversion switch, and/or the like. Each of these components may include cables or connectors or wireless for one or more of a coil interface, a power supply, a serial interface, a control interface, a status interface, an optional ECG interface or lead, an oscillator interface, a processor interface, a computer interface, a data interface, a network interface (cable or wireless), an internet interface, a video interface, a touch-screen interface, an SBC control or power interface, a board interface, a sensor interface, and/or the like as described herein or as known in the art. One or more of these cables or connectors or wireless may attach to a patient drive block 122 or any component thereof. In this representation, the circuitry is operably configured to have a power isolation circuit and a single board computer status and control isolation circuit which span the patient isolation line. Additionally, this representation demonstrates the integration of a programmable digital signal processor, which among other functions, may be configured to furnish the appropriate AC drive signal to the patient drive block and control the phase of the signal provided to a demodulator clock.

Figure 23:
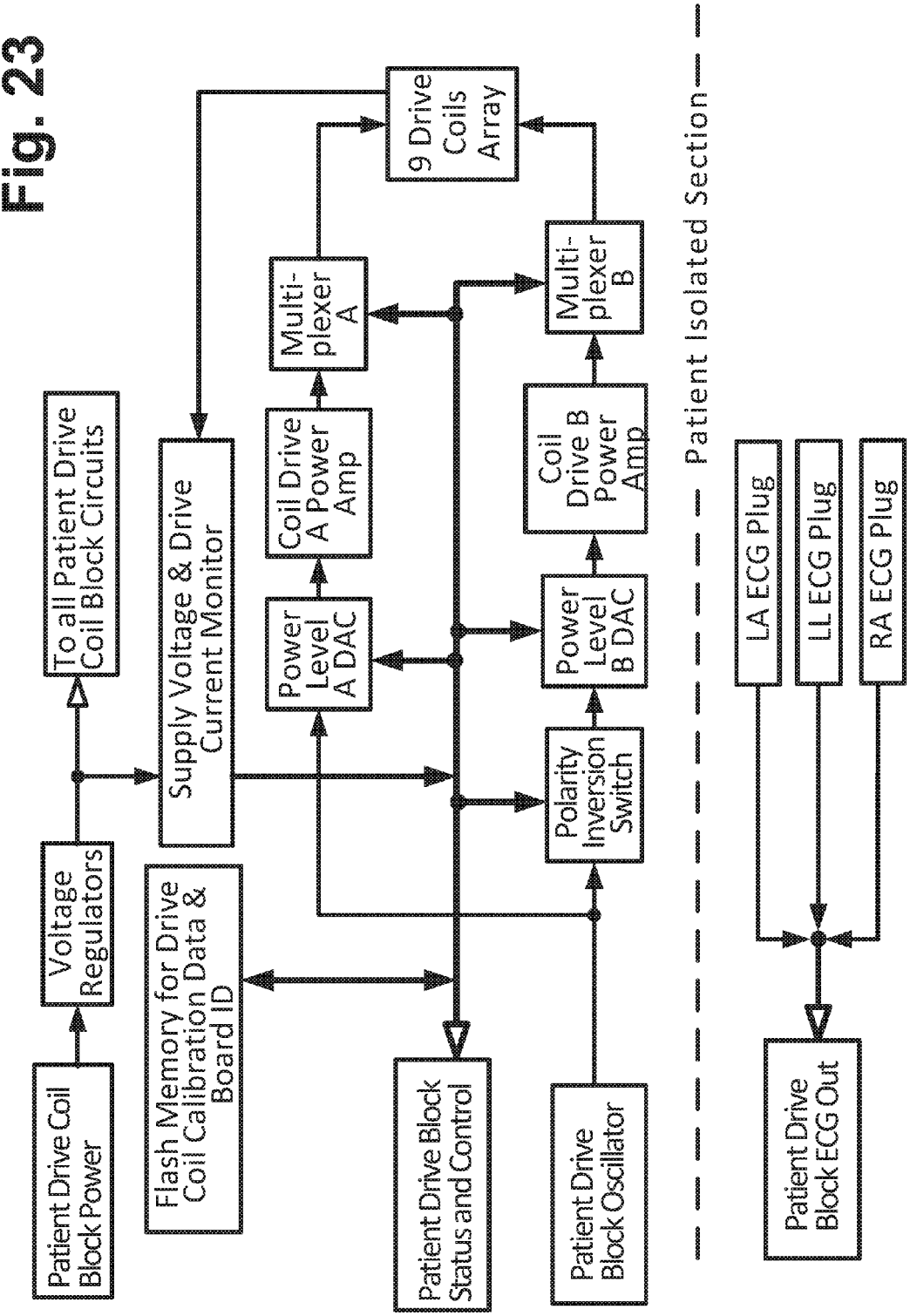
FIG. 23 is yet one further schematic block diagram of a patient drive coil block as may be used herein.

FIG. 23 is a block diagram of a patient drive block 122 (FIGS. 1, 16, 17, 18, 19, 20). An alternative version/option of a patient drive block 122 has two or more ECG leads connected. The drive coil drive system in this diagram illustrates a two-coil virtual drive capability allowing the first component for driving coil operation (which may include or be configured with methodologies whether in computer software or otherwise) to simultaneously drive two or more coils at select power levels. Such a system may include one or more of a voltage regulator, a watchdog switch, a drive switch, a power isolator, a voltage monitor, a cable buffer, a filter, an analog to digital converter, a phase adjuster, a demodulator, a signal filter, a programmable gain amplifier, a coil isolator, a coil sensor coil amplifier, a detector, memory, flash memory, a multiplexor, a polarity inversion switch, and/or the like. Each of these components may include cables or connectors or wireless for one or more of a coil interface, a power supply, a serial interface, a control interface, a status interface, an optional ECG interface or lead, an oscillator interface, a processor interface, a computer interface, a data interface, a network interface (cable or wireless), an internet interface, a video interface, a touchscreen interface, an SBC control or power interface, a board interface, a sensor interface, and/or the like as described herein or as known in the art.

Figure 24:
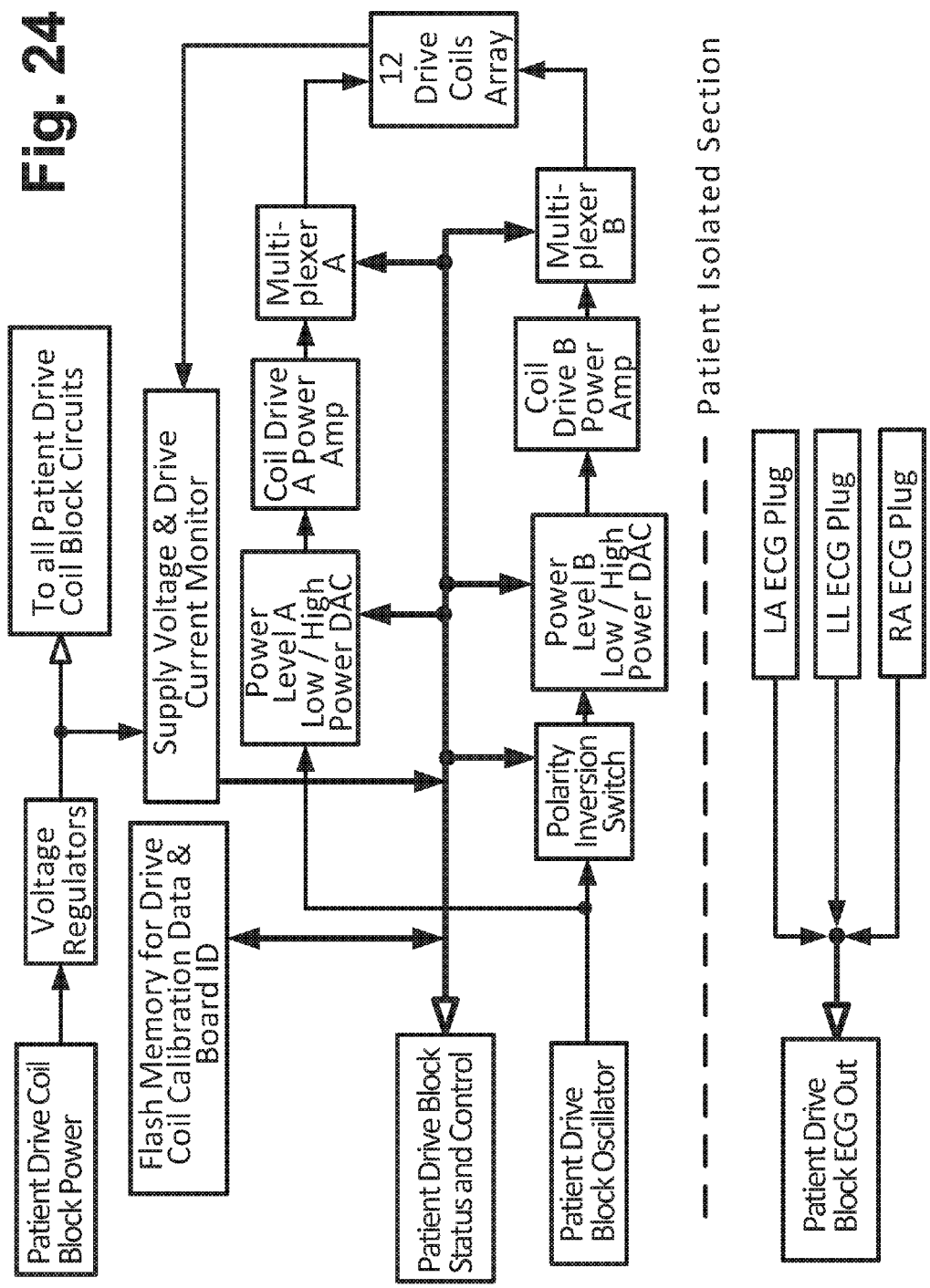
FIG. 24 is still yet one further schematic block diagram of a patient drive coil block connected to a 12 drive coil array as may be used herein.

FIG. 24 provides a block diagram of the patient drive block circuitry as in FIG. 21; however, showing the optional connection to a 12 drive coil array (FIG. 16, inter alia). In alternative embodiments, the drive coil array may have numerous drive coils capable of functioning for the intended purpose (e.g. some embodiments possess 15, 18, 21, 24 or more drive coil arrays). The drive coil arrays are disposed as optionally set out in FIGS. 13, 14, 15 and 17, inter alia, and additional arrangements and configurations are contemplated by the addition of additional drive coil arrays. In alternatives (not depicted in the Figures), the drive coil arrays may be arranged orthogonally or pseudo-orthogonally as described in FIGS. 13-15, but not limited to those implementations.

Figure 25A:
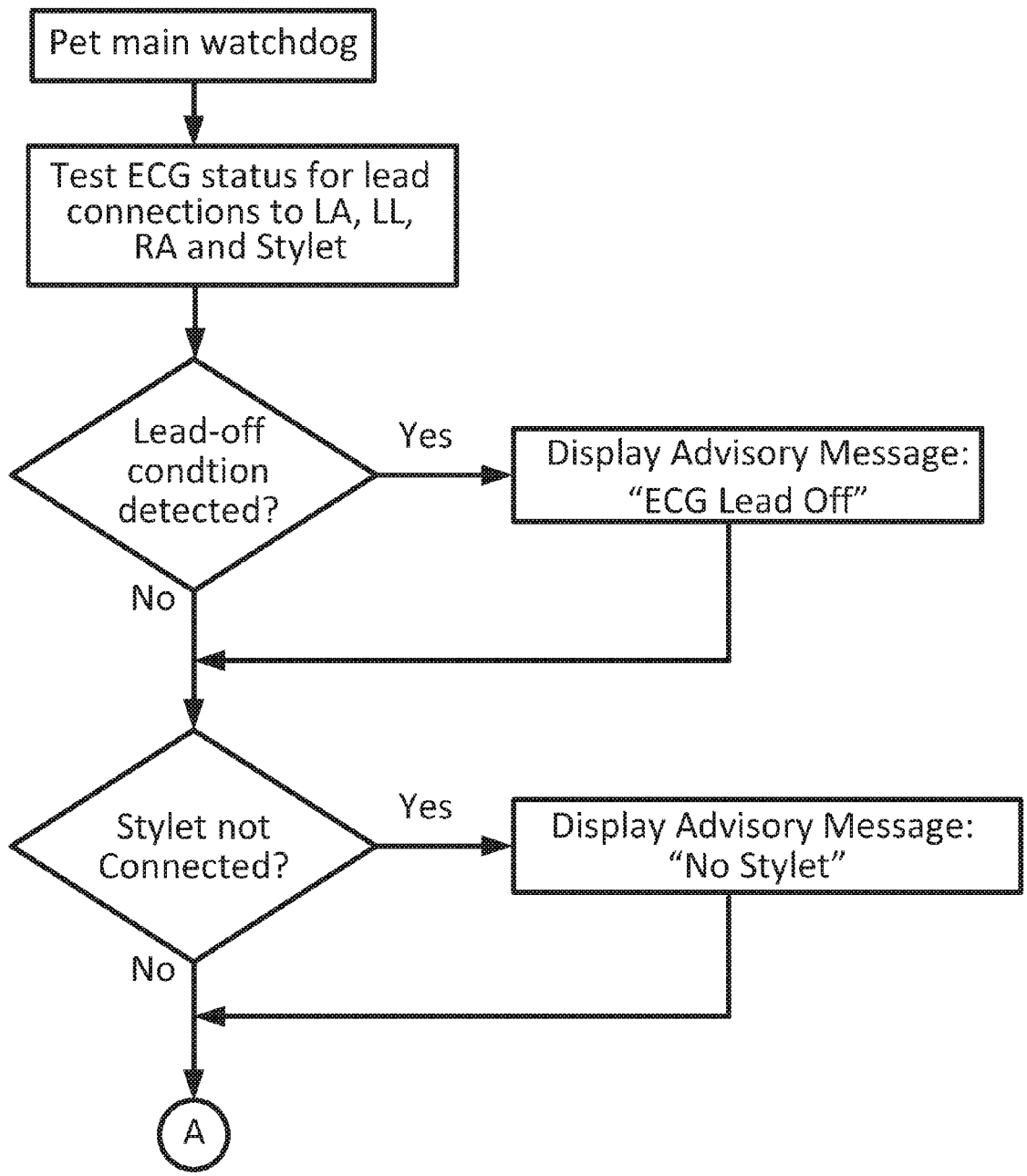
FIGS. 25a-25g are methodologies for controlling an acquisition of sensor coil position.
Figure 25B:
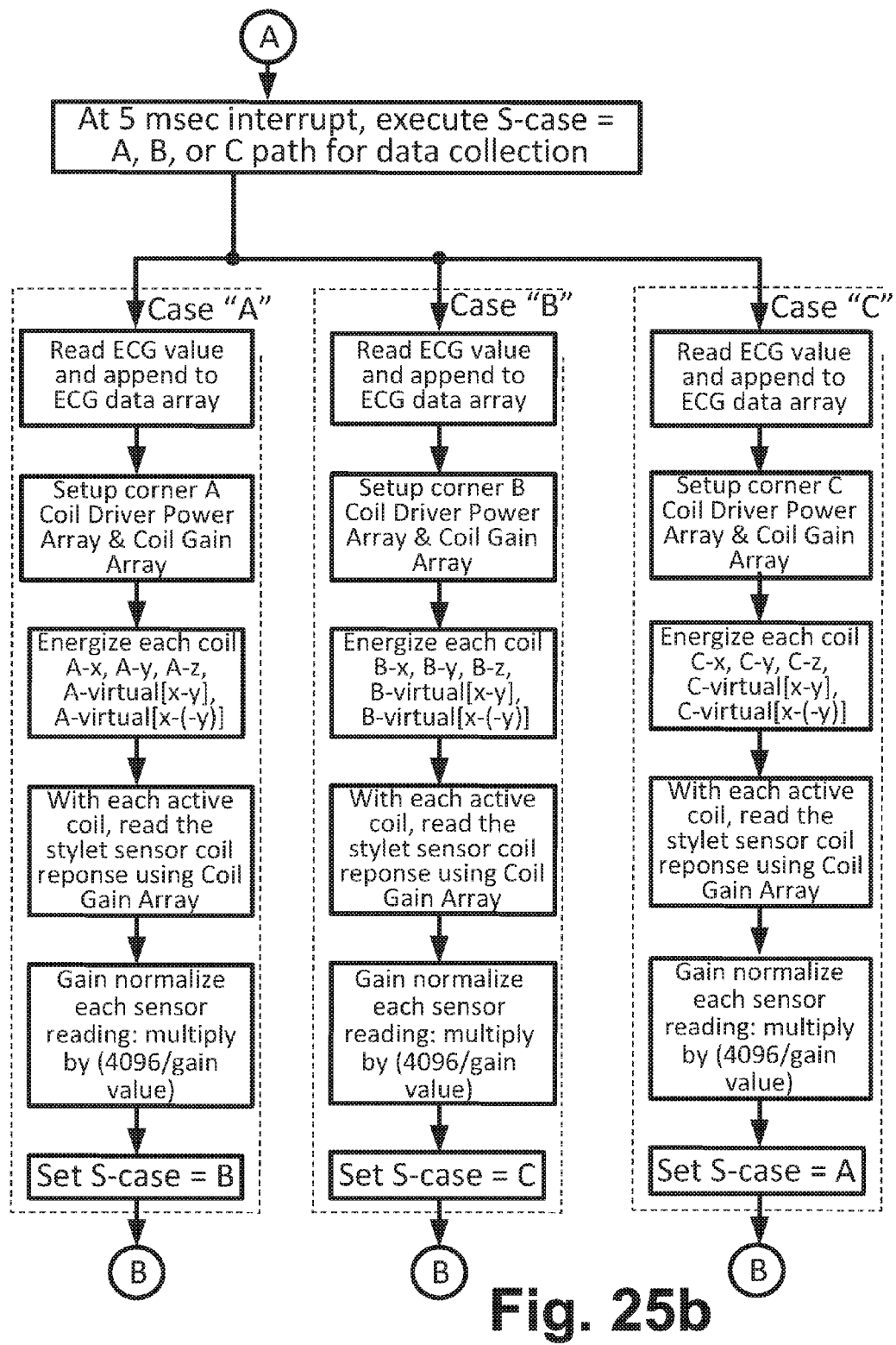
Figure 25C:
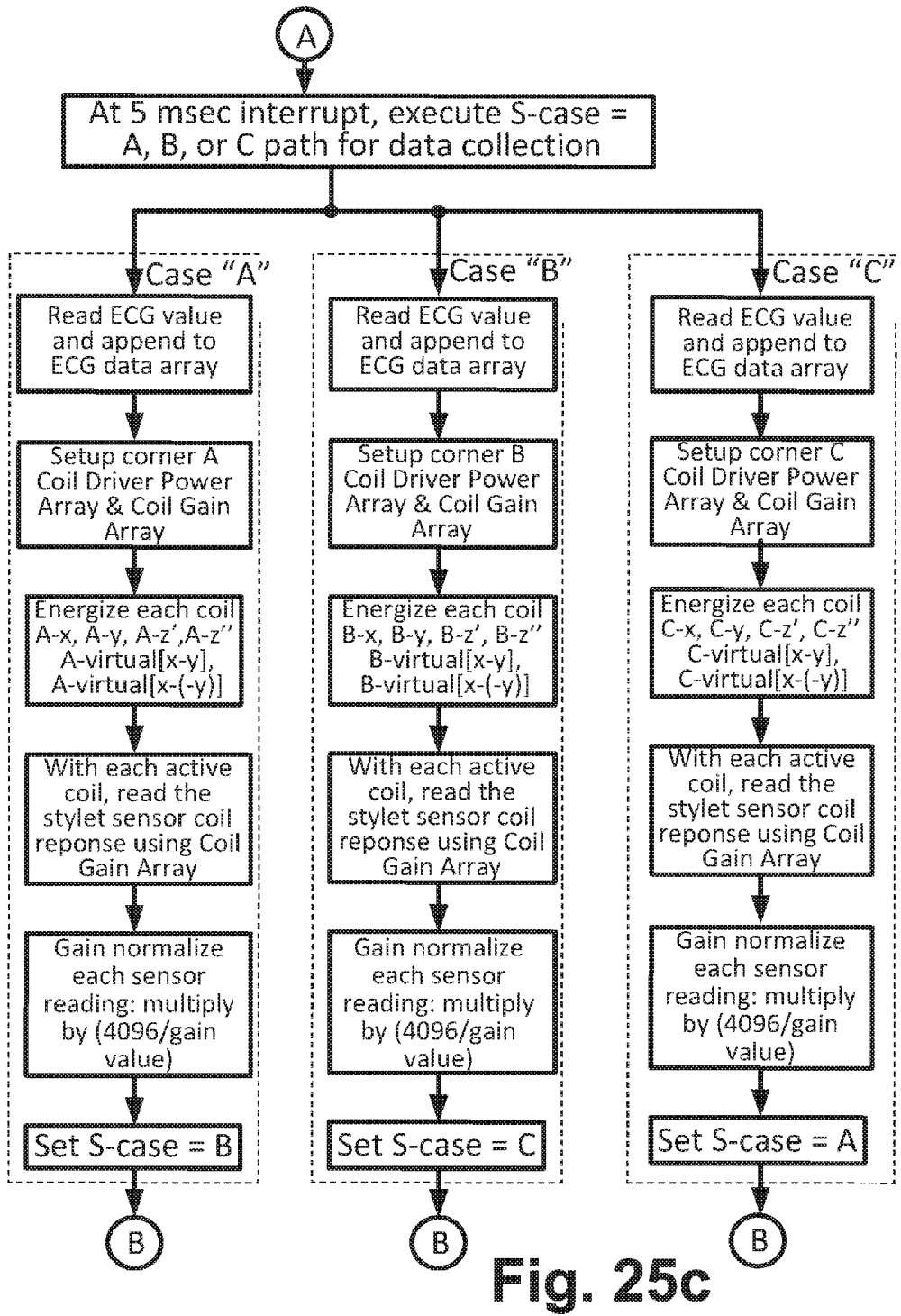
Figure 25D:
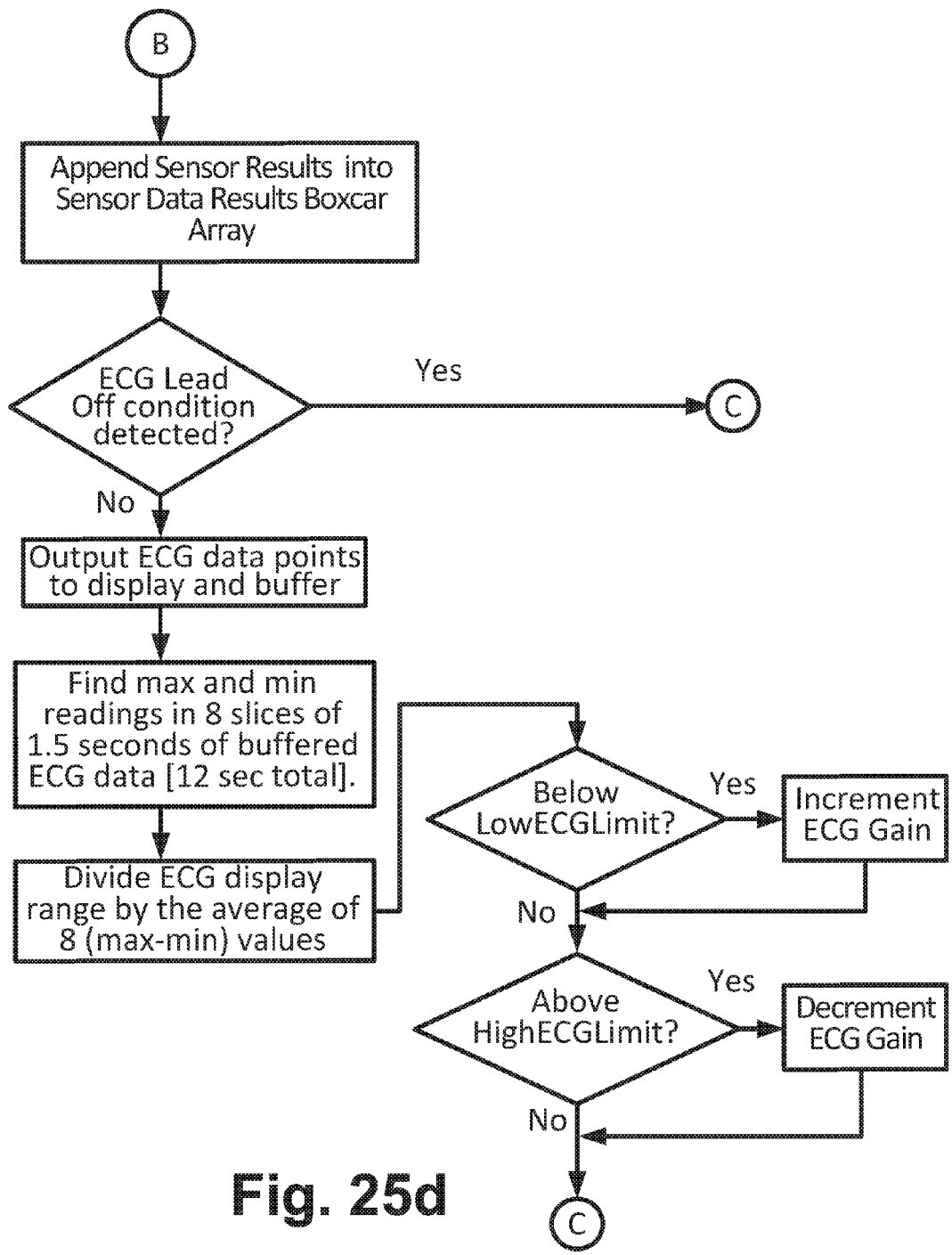
Figure 25E:
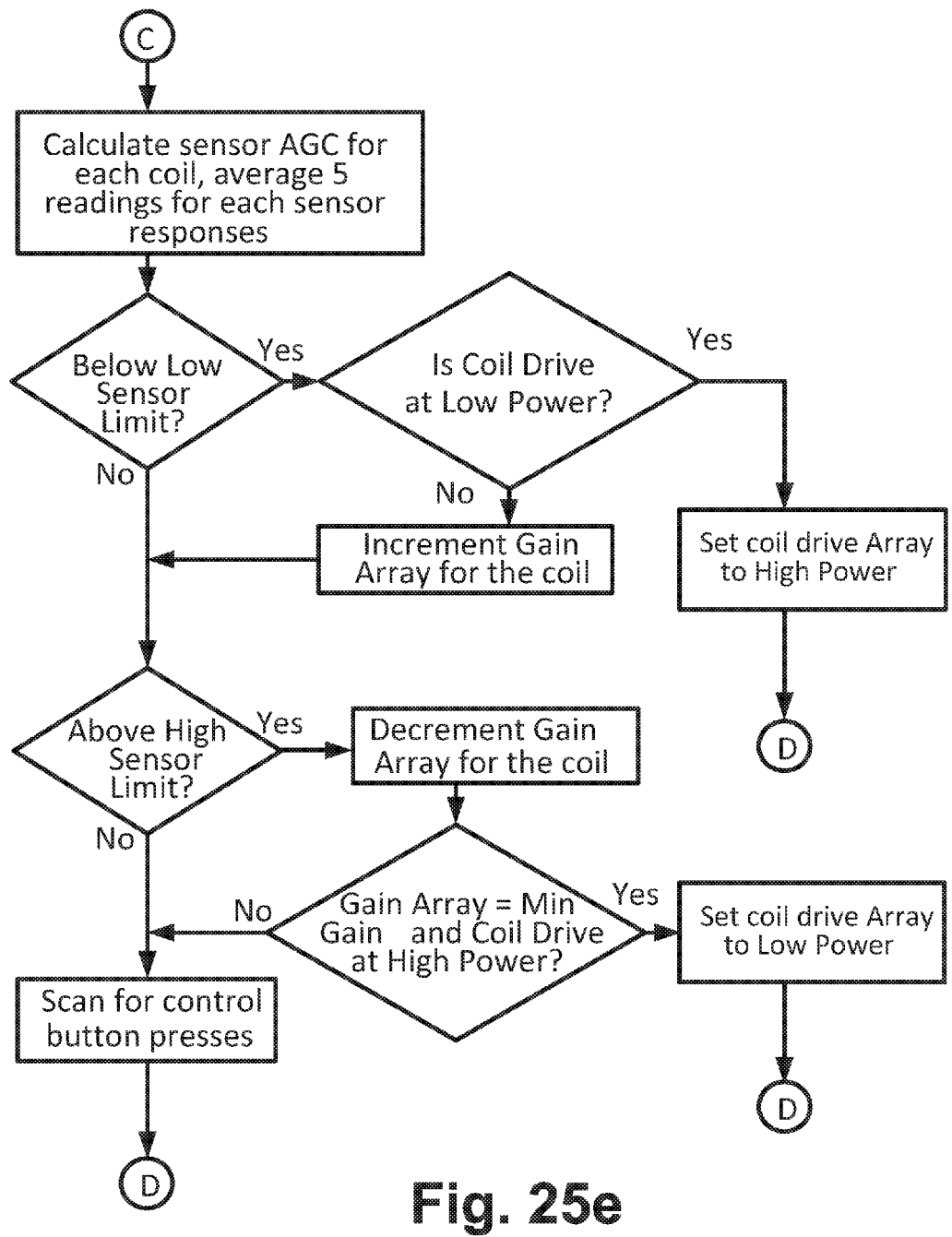
Figure 25F:
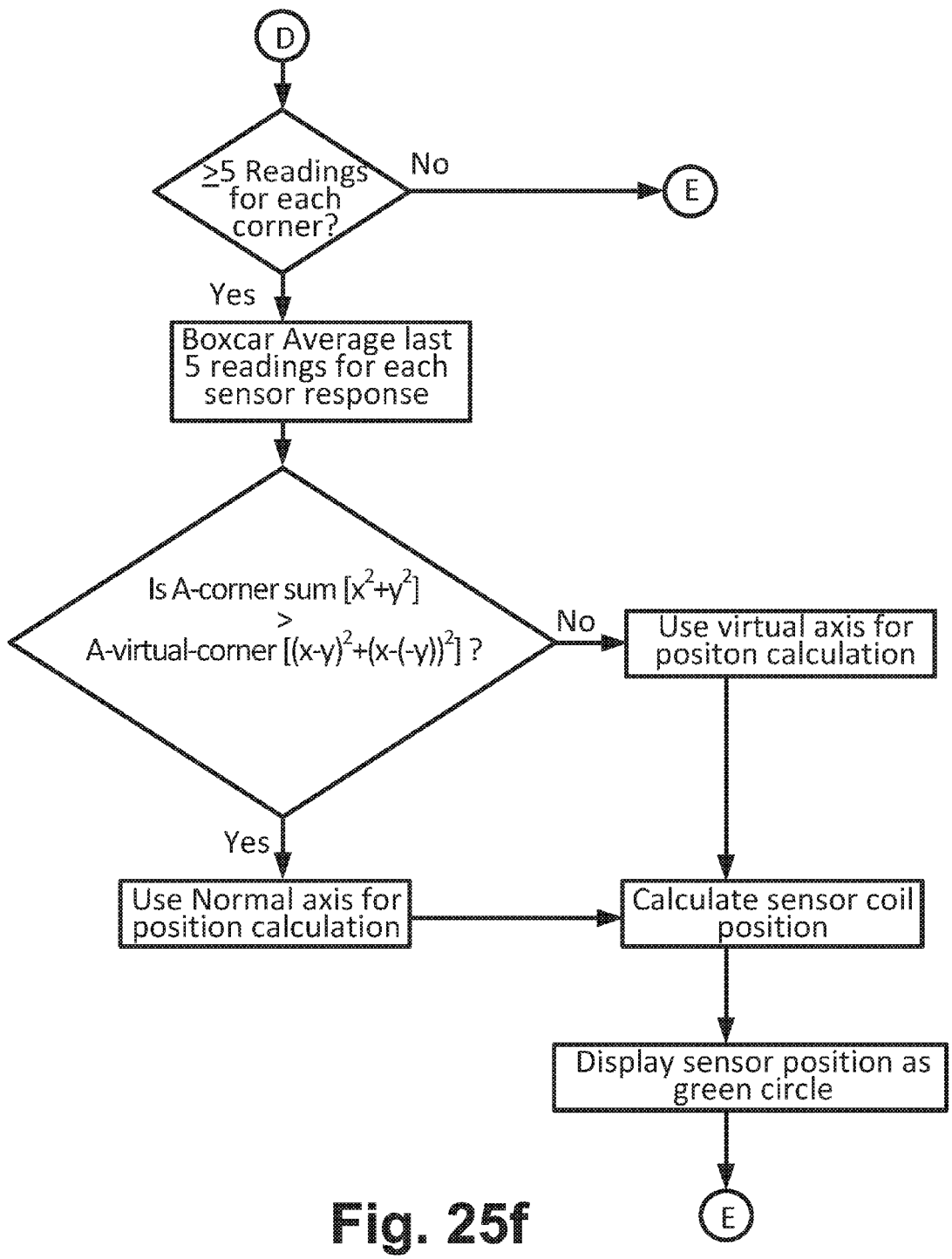
Figure 25G:
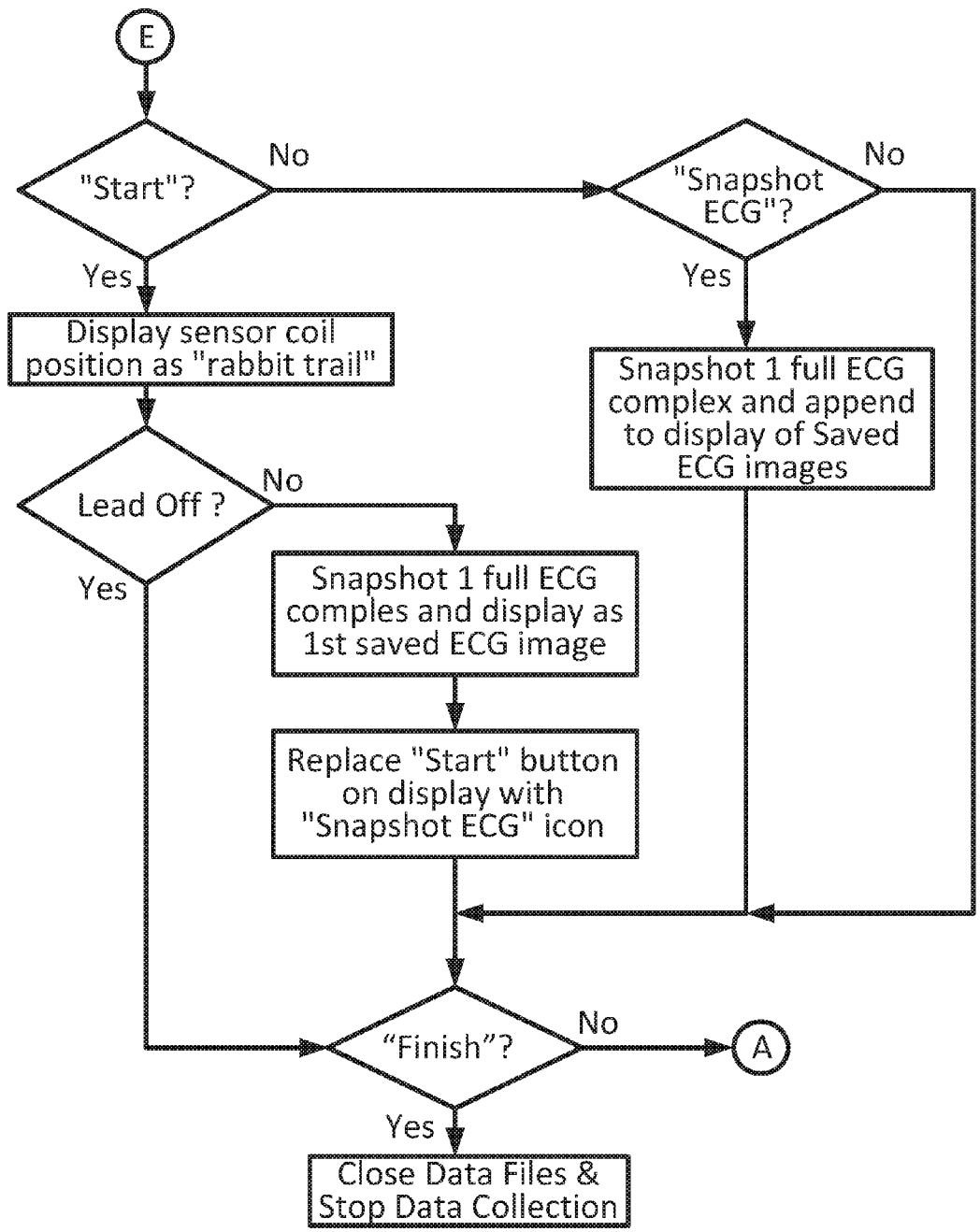

FIGS. 25*a-g* provide an overview by flow charts of methodology functionality options for a medical device position location system hereof. FIG. 25*a* provides an initial check sub-process. FIGS. 25*b* and 25*c* provide alternatives for operation, including energizing coils and reading of coil responses; FIG. 25*b* for a 9-coil array (x, y, z), and FIG. 25*c* for a 12-coil array (x, y, z', z"). FIG. 25d provides subsequent steps including ECG data acquisition and evaluation. FIG. 25e and FIG. 25f provide some alternative subsequent steps for a determining component to use sensor coil response signals to determine sensor coil position and/or location. FIG. 25g provides some optional display steps and a finish or loop back to the start.

Figure 26:
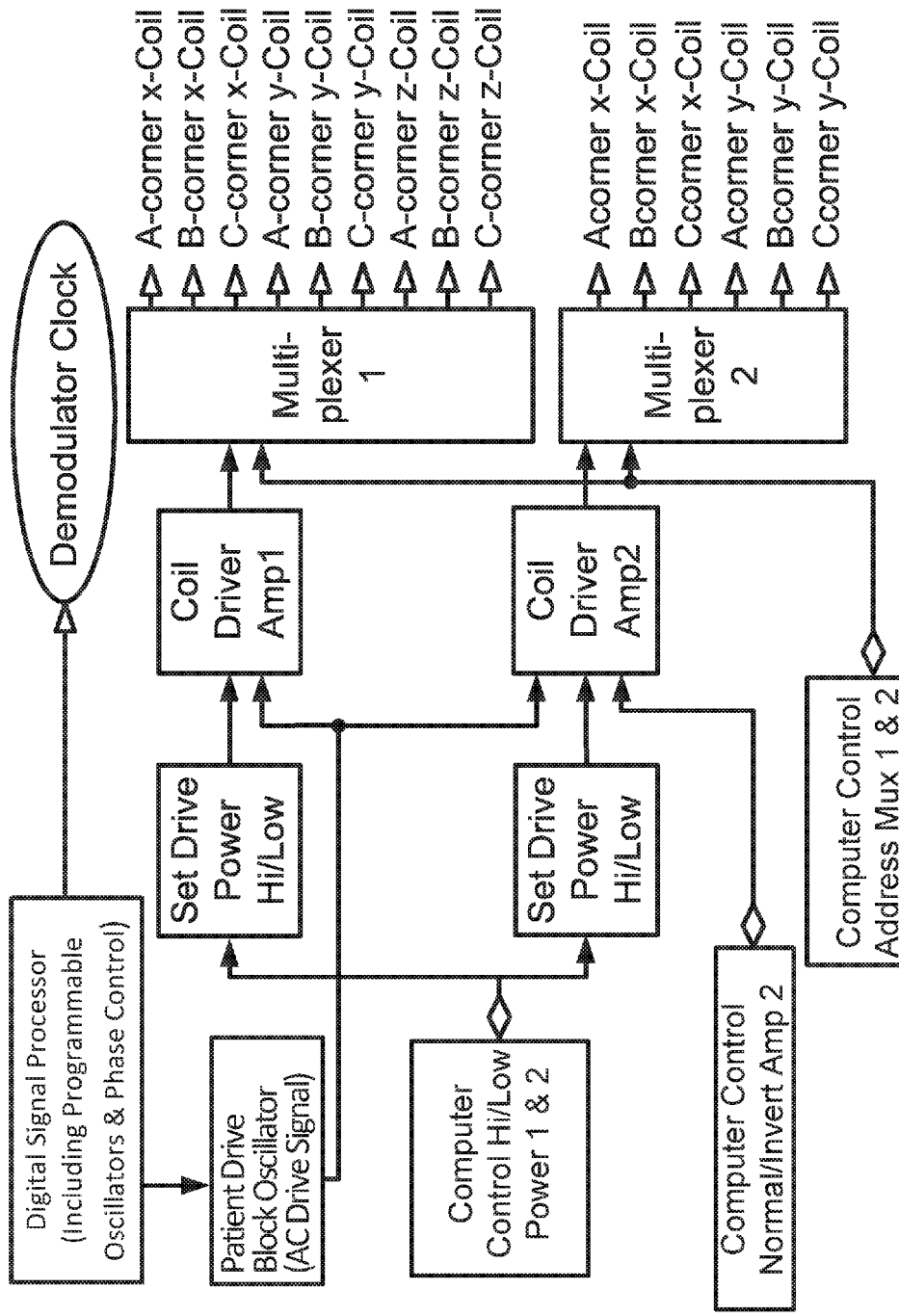
FIG. 26 is a schematic block diagram of a coil drive with virtual x-y capability.

FIG. 26 is a simplified real and virtual coil drive system located on a patient drive block 122, 150. A coil driver hereof may have only two coil drives and only high/low power selection instead of a power control DAC. In this drive system it is possible to generate x-y and x-(-y) virtual coil drive (see FIG. 10) and also y-z and y-(-z) drive (see FIG. 11). One additional feature of this drive is a low power setting which allows drive power reduction if the sensor coil is too close to the drive coil (see methodology flow chart FIG. 25e). It also is possible to have two additional virtual vectors in this drive system by driving x-high-power together with y-low-power or driving x-low-power with y-high-power. Here, driving x-low-power together with y-low-power yields the same virtual axis—forty-five degrees from x and y axes—as driving both at high power. Optionally, this system may be extended to use for and with the x-z and y-z virtual drives and/or virtual drive implementations of z' and z" coils.

Figure 27:
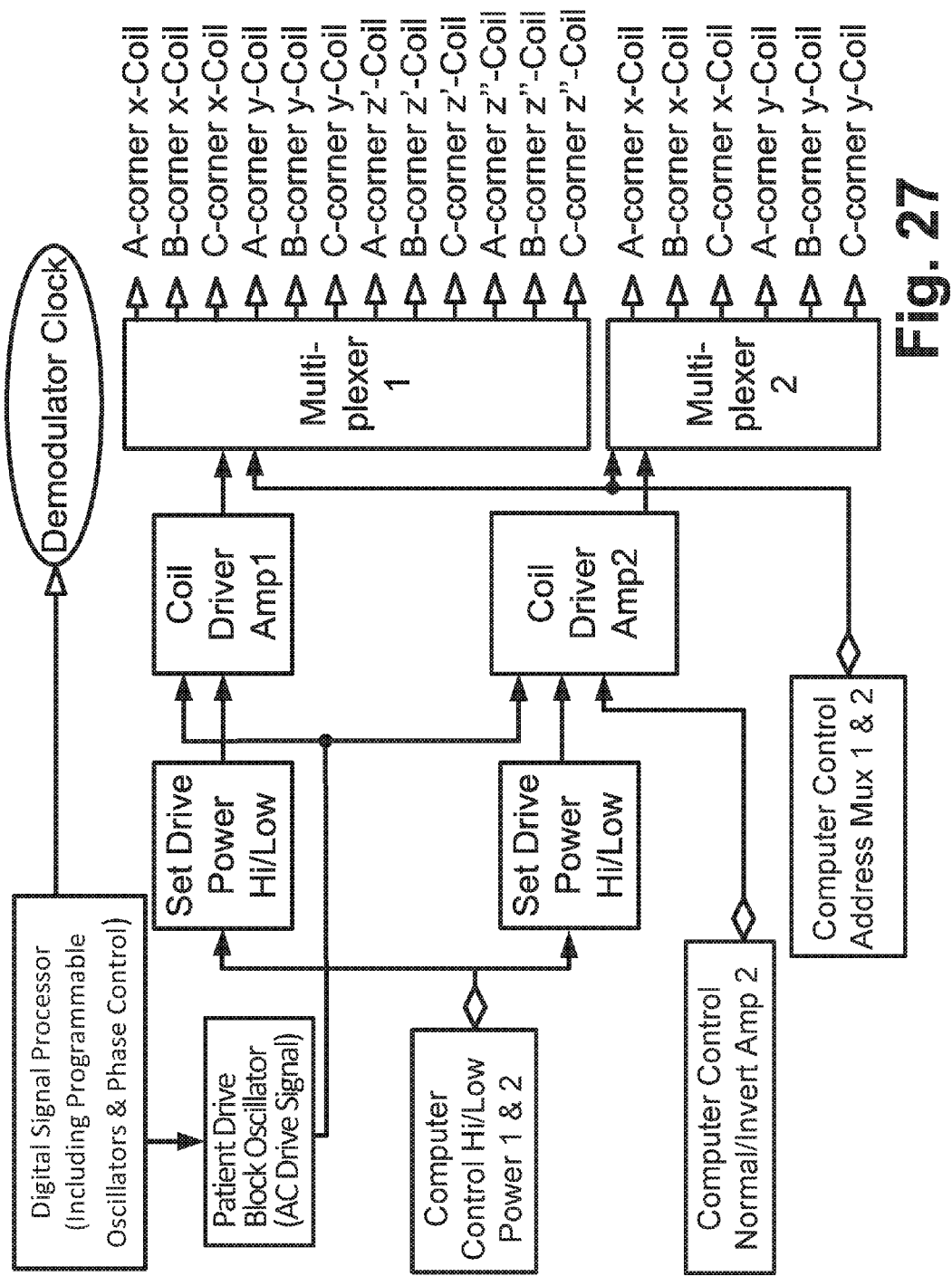
FIG. 27 is a schematic block diagram of a coil drive with virtual x-y capability.

FIG. 27 is a simplified real and virtual coil drive system located on a patient drive coil block 122 wherein the coil array includes a 12 drive coil array inclusive of the z'-coil and the z"-coil.

Figure 28:
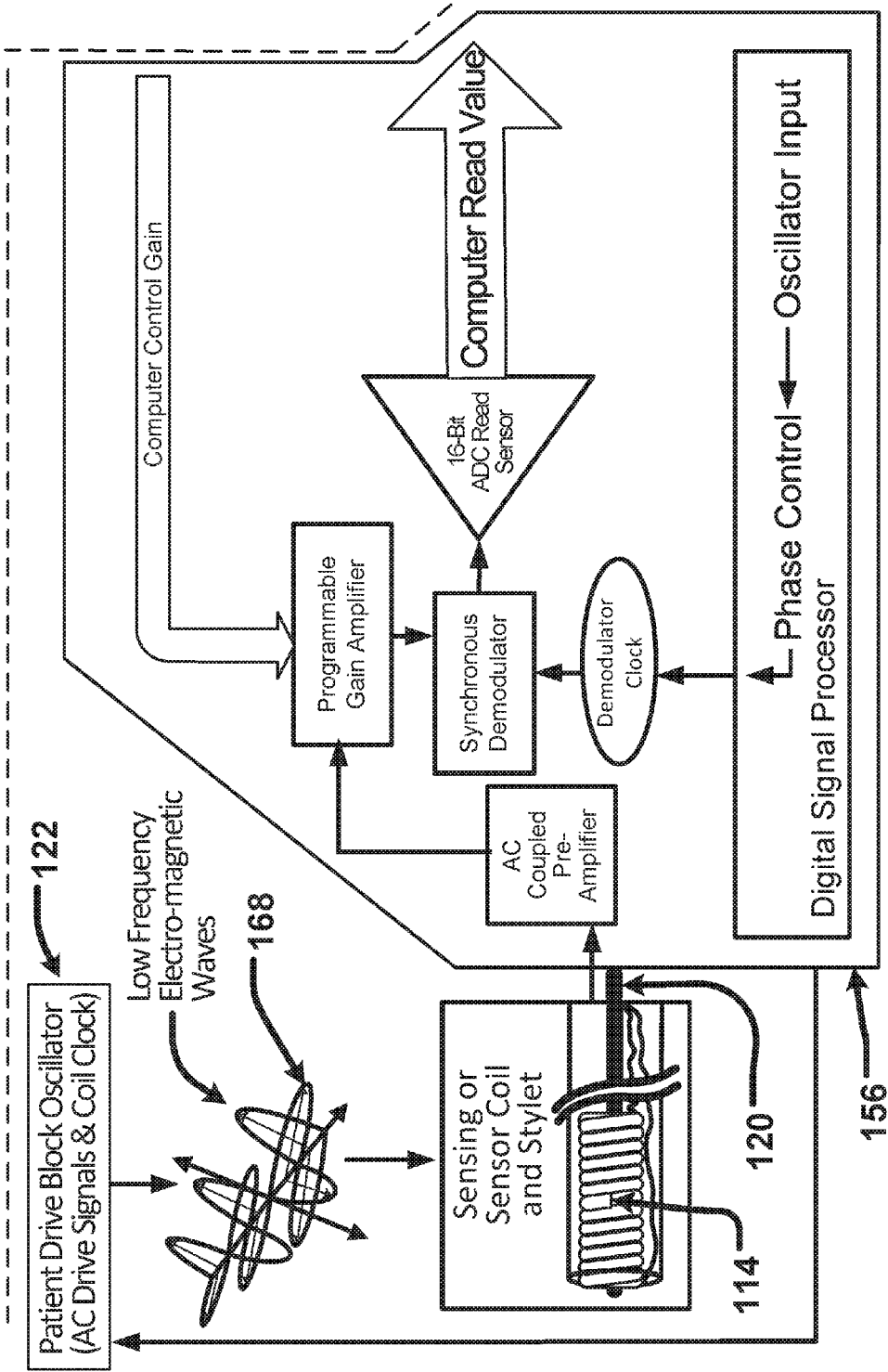
FIG. 28 is a schematic block diagram of sensor coil signal processing.

FIG. 28 is a schematic view of what may be a determining component in a broad sense, and in this implementation is a sensor coil processing system of the main interface board 156 as it uses the electromagnetic signal 168 received by the sensor coil 114. The sensor coil 114 on the guide wire or stylet may be connected through a cable 120, 146 or wirelessly to the main interface board 156. The first system component which may include a programmable digital signal processor (DSP) providing the drive signals to the coils on the patient drive block and/or controlling the oscillation of the drive coils (the electromagnetic emissions) and the coil clock. The first system component with or without a DSP controls and in some implementations selects a preferred low frequency electromagnetic wavelength at which the drive coil array 106 will be driven to oscillate. This sensor coil 114 receives the electromagnetic waves as input which is communicated to/received by the second system component. These are sensor coil response signals. These response signals may be pre-amplified and filtered then optionally passed through a patient isolation transformer to a gain amplifier which may be a software-controlled programmable gain amplifier. This amplified signal is then demodulated using the low frequency (e.g. 16 kHz) drive oscillator. In one non-limiting embodiment, the drive signals are provided as AC drive signals. Furthermore, the AC drive signals may preferably be provided at 16 kHz, as stated above. Providing drive signals at this selected frequency may provide additional operability and functionality and may provide practitioners a functional device that operates on a radio frequency that may avoid interfering with other signals that may commonly be associated or used in modern clinical environments. Concurrently, the DSP may be used to provide oscillator input signals and phase control signals to a demodulator clock. The demodulator clock signals may pass to a synchronous demodulator. The synchronous demodulator and associated software then reads the sensor coil value with a high resolution (e.g. 16 bit or higher resolution) analog to digital converter (ADC). This read value is for each drive coil activation and this value is proportional to the magnetic field measured by the sensor coil during that drive coil activation.

FIG. 29 is a schematic view of an optional more complex virtual drive system. This drive system allows the x-axis coil set 170, the y-axis coil set 172 and z-axis coil set 174 to all be driven simultaneously at independent power levels set by computer control through individual digital to analog converters (DAC). In this drive system, the virtual magnetic vector is the vector sum of x-axis drive plus y-axis drive plus z-axis drive. This virtual drive permits the virtual vector to point to any polar coordinate in space, and thus use polar coordinates as an option; however, it may often still be preferable to use a set of three orthogonal "virtual" axes to calculate the sensor coil 114 position. This alternative further demonstrates a possible integration of the digital signal with a complex drive system.

Figure 30A:
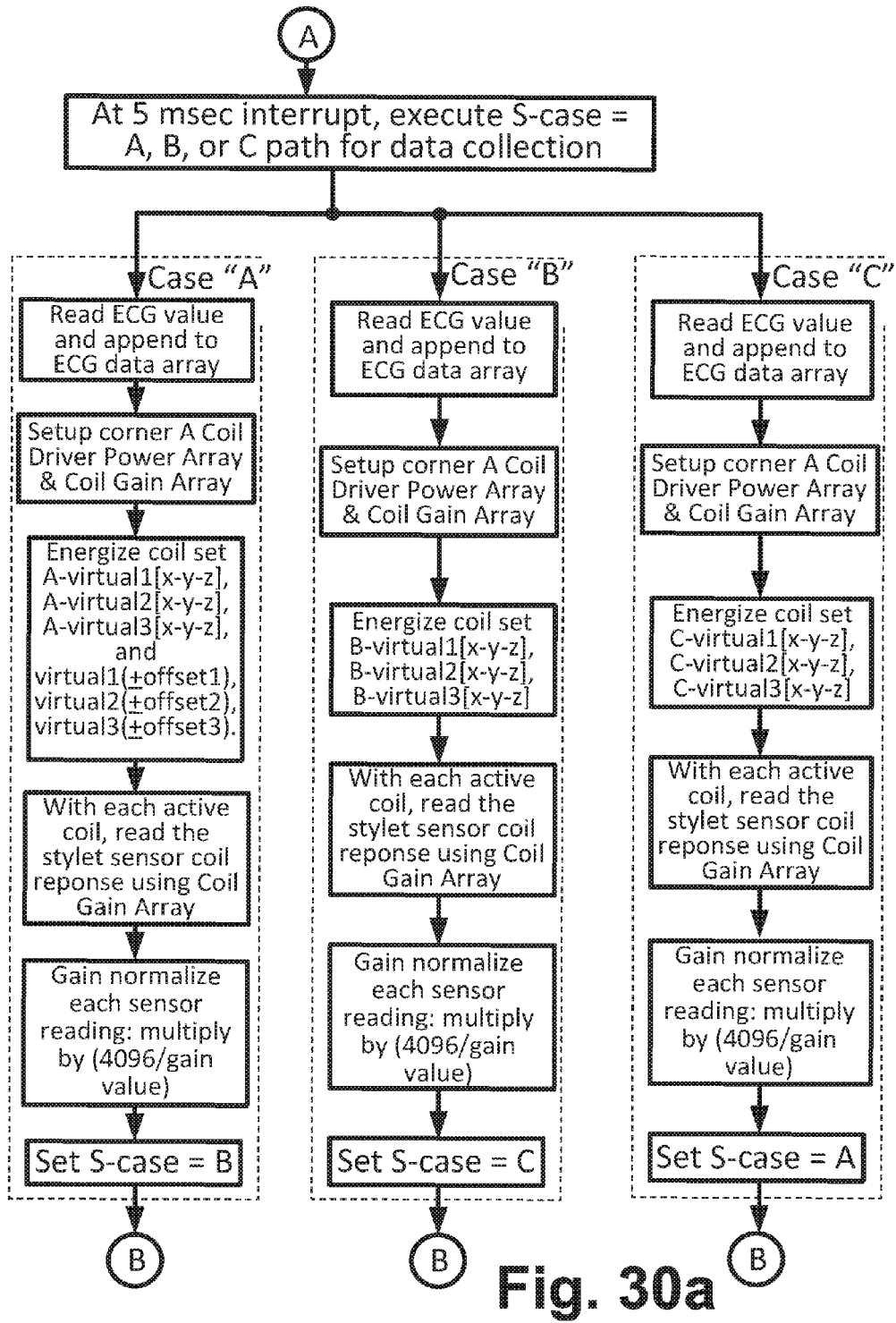
FIGS. 30a-30b are methodology alternatives for controlling one or both the acquisition and display of sensor coil position in virtual x-y-z system.
Figure 30B:
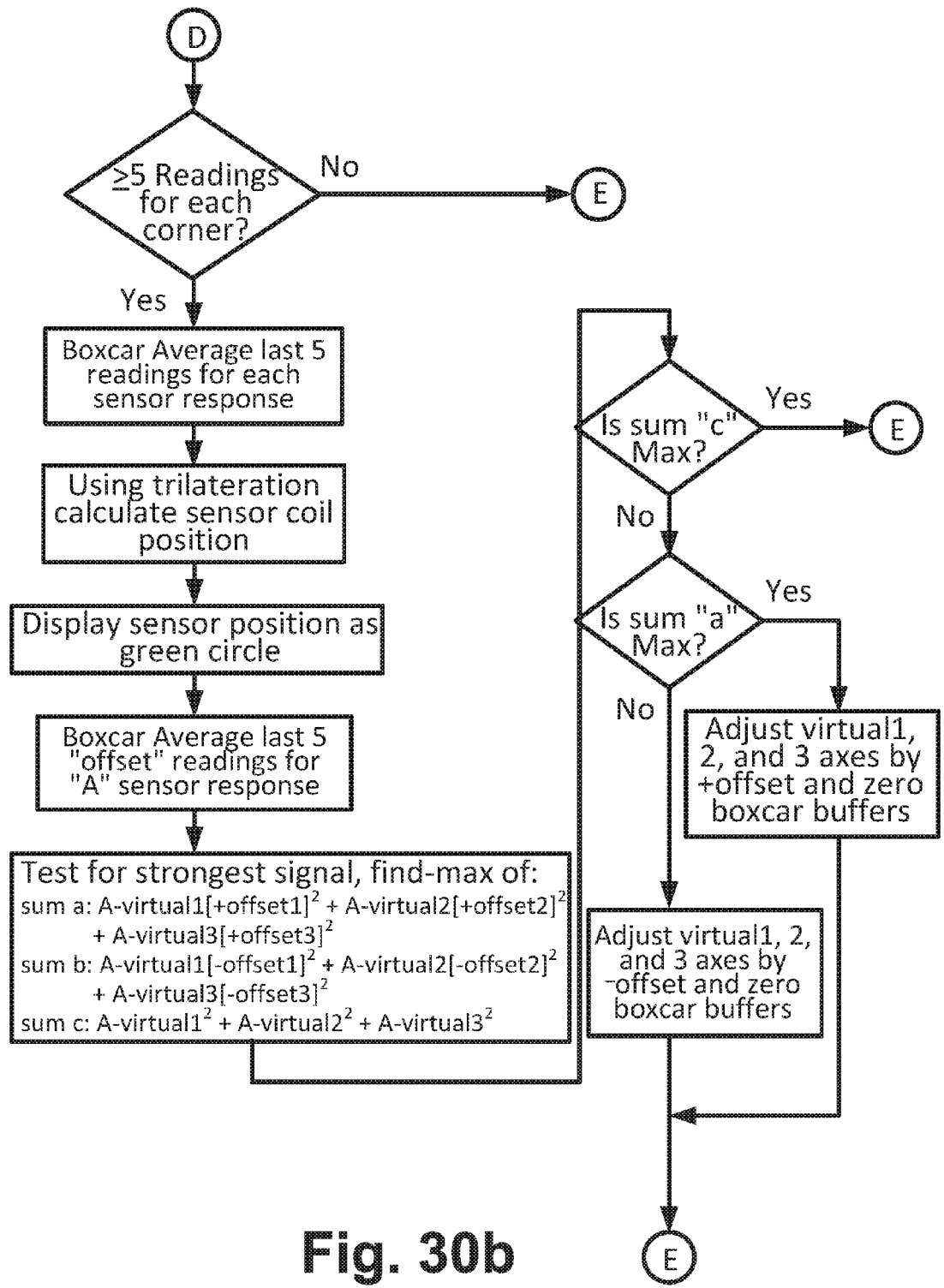

FIGS. 30a-b provide a methodology flow chart showing optional changes for drive and sensor coil response processing for a fully independent x-y-z virtual drive system (see FIG. 29). This methodology may add a positive offset test and a negative offset test to the virtual axes for the A-corner set of coils. If the sensor coil response is stronger for an offset axis (FIG. 30b) than the current virtual axes, the system shifts to use the offset axes.

Figure 31:
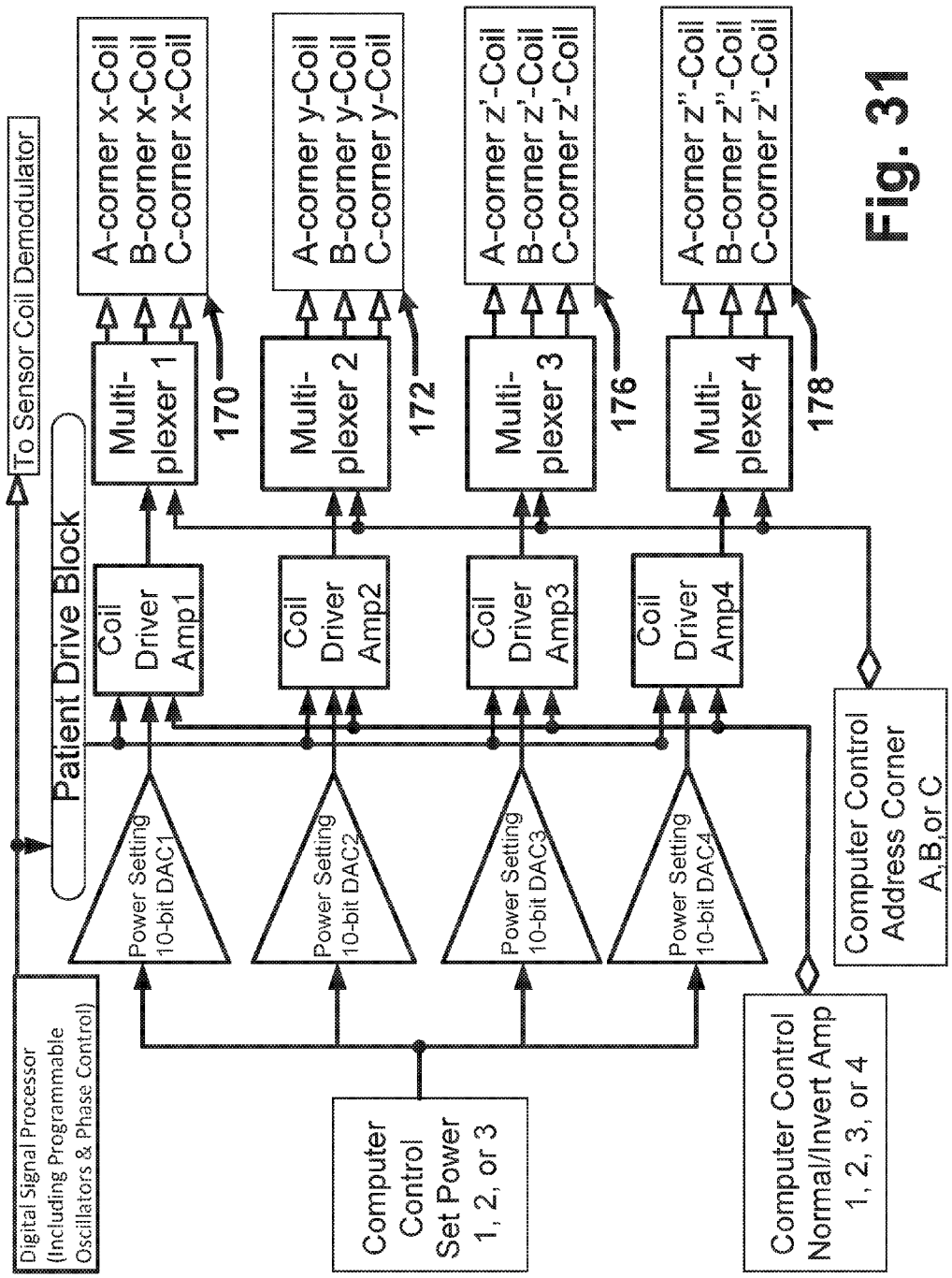
FIG. 31 is a schematic block diagram of a coil drive with full virtual x-y-z'-z" capability.

FIG. 31 is a detailed view of yet another non-limiting embodiment of a more complex virtual drive system. This drive system allows the x-axis coil set 170, the y-axis coil set 172, z'-axis coil set 176, and z"-axis coil set 178 to all be driven simultaneously at independent power levels set by a controller (which may include or involve a computer control) through individual digital to analog converters (DAC). In this drive system, the virtual magnetic vector is the vector sum of x-axis drive plus y-axis drive plus z-axis drive. In this instance, the z-axis drive may be obtained using measured values from the z'-axis drive and the z"-axis drive. This virtual drive permits the virtual vector to point to any polar coordinate in space, and thus use polar coordinates as an option; however, it may often still be preferable to use a set of three orthogonal "virtual" axes to calculate the sensor coil 114 position. This alternative further demonstrates an integration of the digital signal with a complex drive system.

Figure 32:
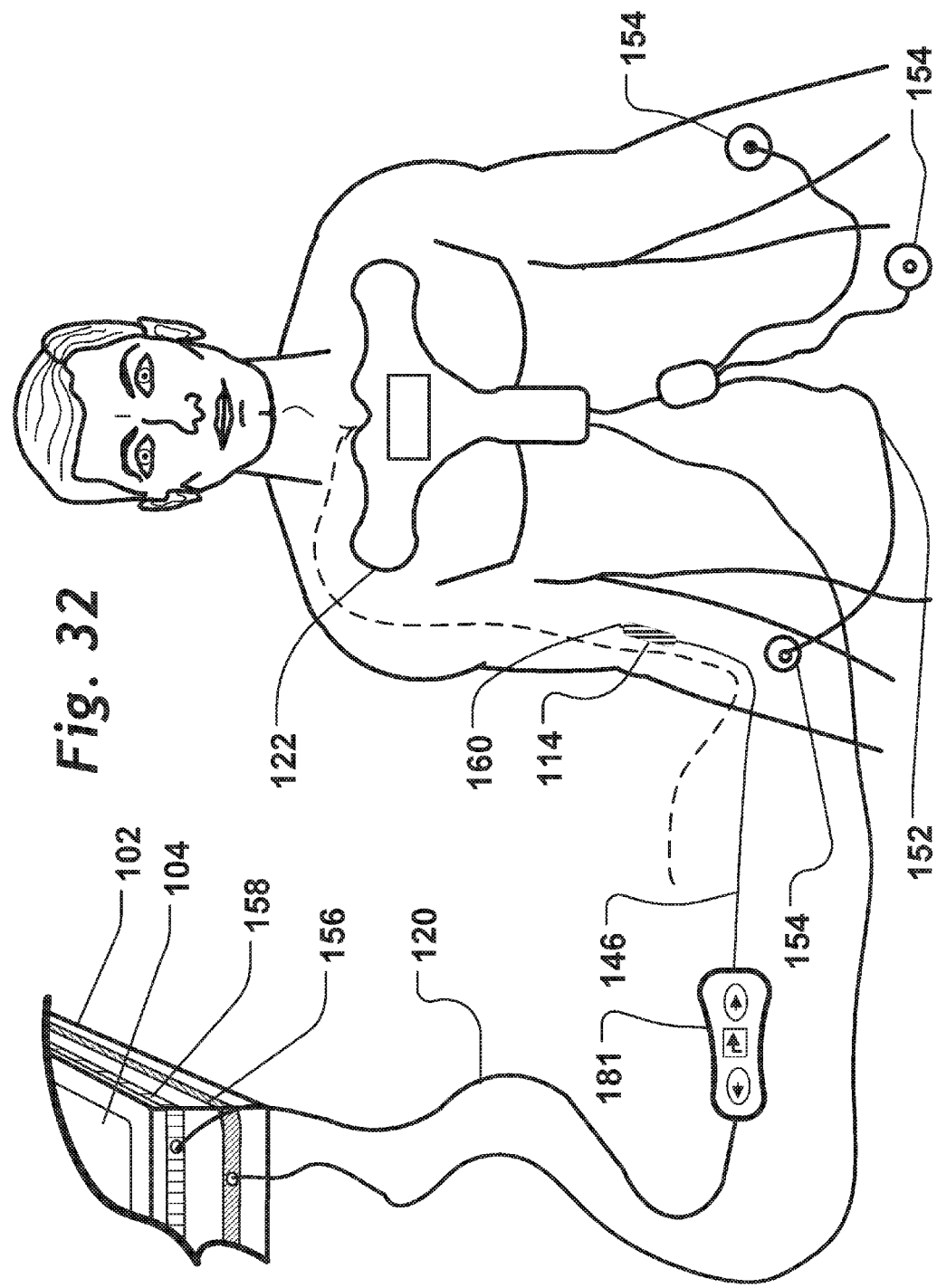
FIG. 32 is a schematic overview of yet another present development hereof in which the present development is placed or in operative relationship to a subject.

FIG. 32 is an overall schematic diagram of a medical device position location system in use relative to a subject or patient. This figure illustrates connections between a user control box 102 and a sensing guide wire or stylet 114 and a patient drive block 122. The control box 102 may include an integrated, separated, or remote user display and/or interface. In this embodiment a user remote 181 may be operably associated with and connected to the control box and the medical probe. Each of these components may include cables or connectors or wireless communications for one or more of a coil interface, a power supply, a serial interface, a control interface, a status interface, an ECG interface or lead, an oscillator interface, a processor interface, a computer interface, a data interface, a network interface (cable or wireless), an internet interface, a video interface, a touch-screen interface, an SBC control or power interface, a board interface, a sensor interface, an isolator interface, and/or the like as described herein or as known in the art. One or more of these cables or connectors may attach to the patient drive block 122 or any component thereof. This figure further demonstrates one possible insertion point 160 into the subject. Optionally, in this instance the device may be inserted in a peripheral vasculature of the subject, specifically the right arm of the patient. Optionally, the system may be configured for use at other insertion sites on the patient's body as may be determined by either medical staff and/or the desired application and use of the system. In alternative embodiments, the system could optionally be implemented for use among a number of different entry or insertion points (e.g. peripheral insertion (cephalic vein), midline insertion (basilic vein), central venous insertion (interjugular vein), chest insertion (subclavian vein or axillary vein) or groin (femoral vein)). Moreover, in yet another implementation, the system could be used for placement at insertion sites for nephrostomy or kidney dialysis. The patient drive block 122 may be adapted to different shapes, configurations, or arrangements that may align with anatomical features of the subject. In alternative non-limiting embodiments, the designated drive block notch may be adapted to be one or more of a notch, an extrusion, a marked portion, or an alignment hole. The patient drive block may be disposed or enclosed in a patient drive block housing made from a material suitable for clinical applications such as molded plastic or other materials known in the art. The housing may provide a protective shell, casing or housing for the electronics of the array of drive coils. These embodiments of different shaped shells, casings, or housings may assist in the medical personnel placing the patient drive block on the subject aligned with anatomical features of the subject.

Figure 33:
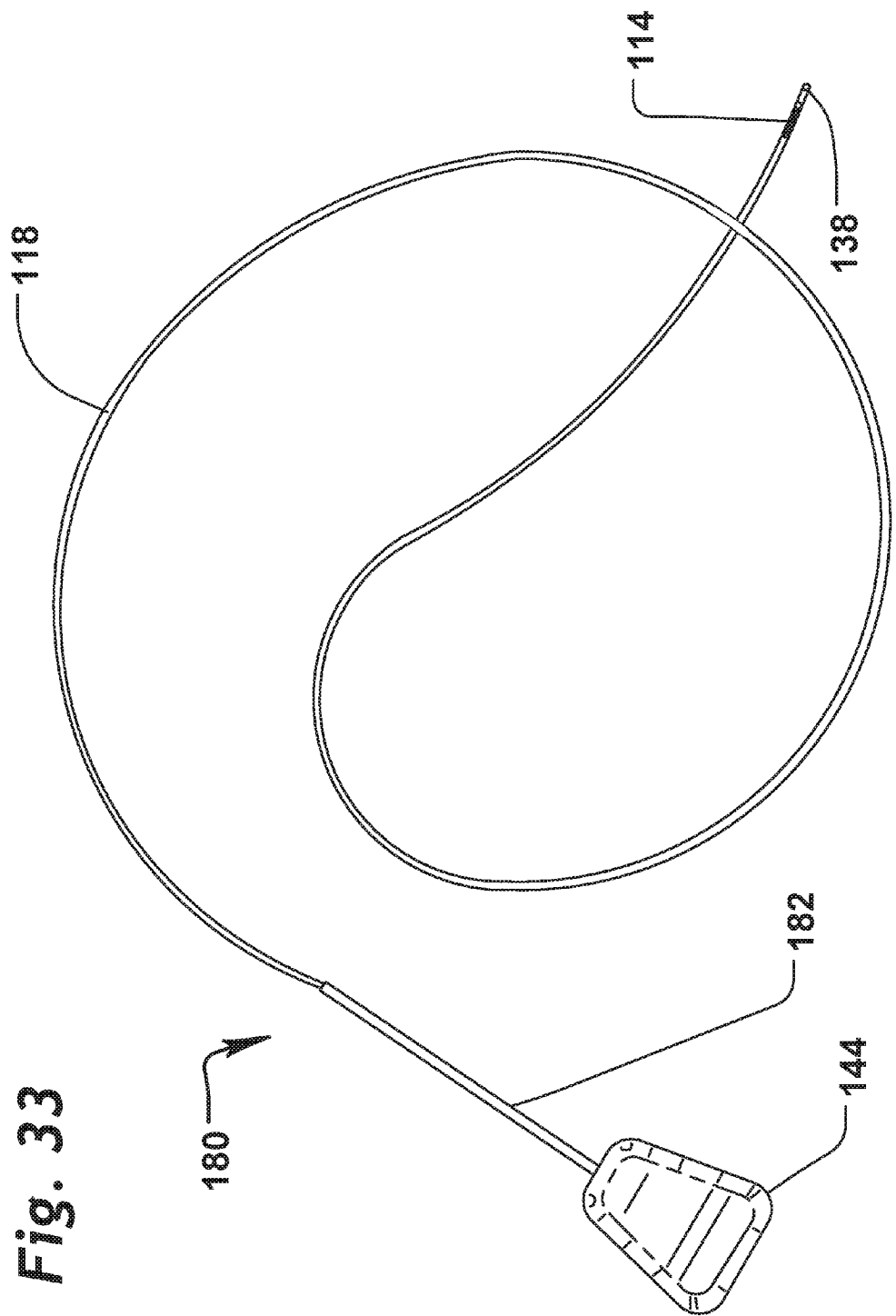
FIG. 33 is a perspective view of a medical probe of an exemplar of some present developments hereof.

FIG. 33 is a perspective view of the medical probe of an exemplar of some present developments hereof. The medical probe 180 may include an elongate flexible bio-compatible core wire having a proximal end electrically and physically connected to jack or electrical connection 144. The core wire 138 and associated sensor coil leads (not separately depicted in FIG. 33, see FIG. 7, 8 inter alia) may be further supported, protected, or structurally enhanced by a short sheathing, jacket, or tubing 182, in some instances this may be made of high-density polyethylene (HDPE) material known in the art to provide lubricious support for medical probes. The distal end of the medical probe 180 includes an uncovered portion 138 adapted to provide an ECG signal as further disclosed herein, and a sensor coil 114 (FIG. 7 inter alia).

FIG. 34 is an overall schematic diagram of a medical device position location system 100 in use relative to a subject or patient 188. This figure illustrates connections between a user control box 102 and a bio-compatible wire 118 and a patient drive block 122. The control box 102 may include an integrated, separated, or remote user display and/or interface. In this embodiment a user remote 181 may be operably associated with and connected to the control box and the medical probe. A practitioner or user 186 may use the remote 181 to navigate an optional graphical user interface that may be located in the user control box 102. Each of these components may include cables or connectors or wireless communications for one or more of a coil interface, a power supply, a serial interface, a control interface, a status interface, an ECG interface or lead, an oscillator interface, a processor interface, a computer interface, a data interface, a network interface (cable or wireless), an internet interface, a video interface, a touch-screen interface, an SBC control or power interface, a board interface, a sensor interface, an isolator interface, and/or the like as described herein or as known in the art. One or more of these cables or connectors may attach to the patient drive block 122 or any component thereof. The patient drive block 122, including the drive coil sets 106, may be adapted to different shapes, configurations, or arrangements that may align with anatomical features of the subject. In this non-limiting embodiment, the patient drive block 122 is electrically connected to receive ECG signals from surface ECG leads and/or pads 154 placed on the patient in order to obtain an ECG of the subject 188. In this development, the practitioner 186 may use the system to monitor the ECG of the subject using either the ECG pads located on the surface or the ECG sensor located on the distal end of the medical probe or bio-compatible core wire 118. Either ECG signal, surface or intravascular may be displayed simultaneously with the received, measured, and modified sensor coil signals. In this development, the system may provide two forms of information to locate a medical probe in a patient. The simultaneous receiving and measuring of ECG signals and sensor coil response signals may provide data for confirmation of the location of a suitable accuracy and precision such that other medical procedures may be performed more rapidly.

FIG. 35*a-b* provide a cross-sectional view of the distal end of a medical probe and developments hereof. In the embodiment as depicted in FIG. 35*a*, the core wire 118 is encircled by a sheathing or tubing 140, in some instances polyimide tubing or other materials known in the art. The tip of the core wire may be left uncovered but is polished such that it may be disposed in a subject as an indwelling catheter. The medical probe is disposed within a catheter 192 wherein the core wire is provided with enough lubricity such that the core wire 118 and associated sensor coil 114 may be extended and retracted. In an alternative embodiment of FIG. 35*b* the core wire 118 may be coated with a layer of an insulator or sealant 140; however, in this embodiment the core wire may be fixed in place in an alternative arrangement of the flexible tubing and the medical probe. In this embodiment of FIG. 35*b*, the flexible tubing is adapted to provide one or more channels or lumens 193 to provide fluid, drugs, or the like without removing the core wire 118 and sensor coil 114 from the physical association with the distal end of the flexible tubing. A small amount of medical grade adhesive 194 may be used to affix or fasten the elongate flexible tube 192 to the medical probe. This alternative embodiment may provide the practitioner an alternative way to adjust the length of the medical probe. In many clinical settings, the clinician must shorten the elongate flexible end prior to insertion into the patient. This alternative FIG. 35*b* may provide a for medical probe or stylet that is not positionable or removable due to the medical probe being affixed, fastened, locked, or held in place by other suitable means. In this non-limiting embodiment, the medical probe or stylet may be cut to length at the proximal end. Furthermore, this present development of FIG. 35*b* may provide the practitioner with certainty that the stylet or guidewire will not become detached or dissociated with the physical association with the catheter.

Figure 36A:
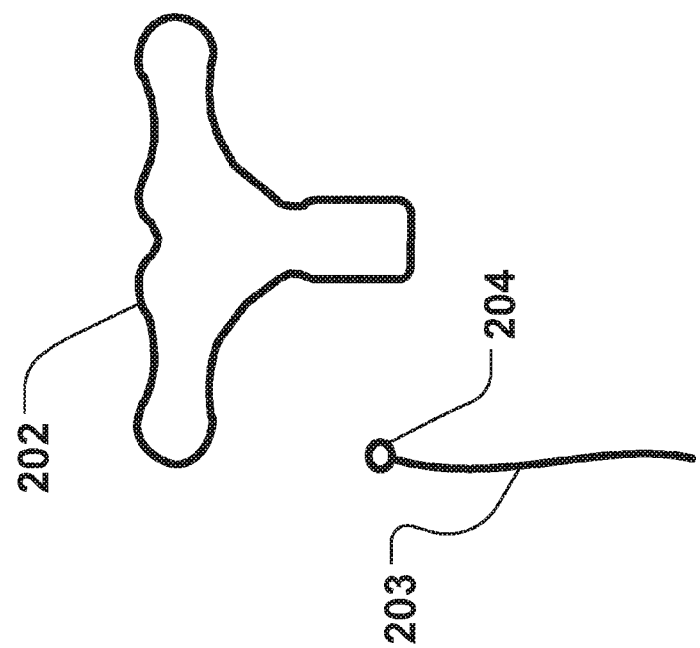
FIGS. 36a-36b are various views of a display of an exemplar of some present developments hereof.
Figure 36B:
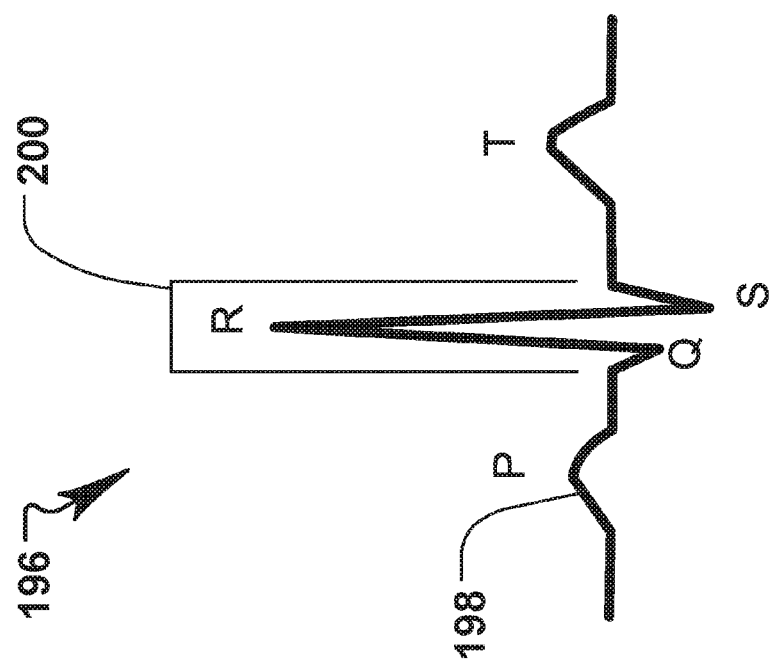

FIGS. 36*a-b* provide various views included in the display of an exemplar of some present developments hereof. FIG. 36*a* provides an illustration of one possible ECG wave complex 196. This illustration includes a P-wave 198 and a QRS complex 200. FIG. 36*b* provides an illustration of an on-screen display of the distal end of the catheter 204 and further provides a reference trail 203. The reference trail 203, may also be referred to as a position track, a tracking, a track, a path, a reference path, or a recorded track.

Figure 37:
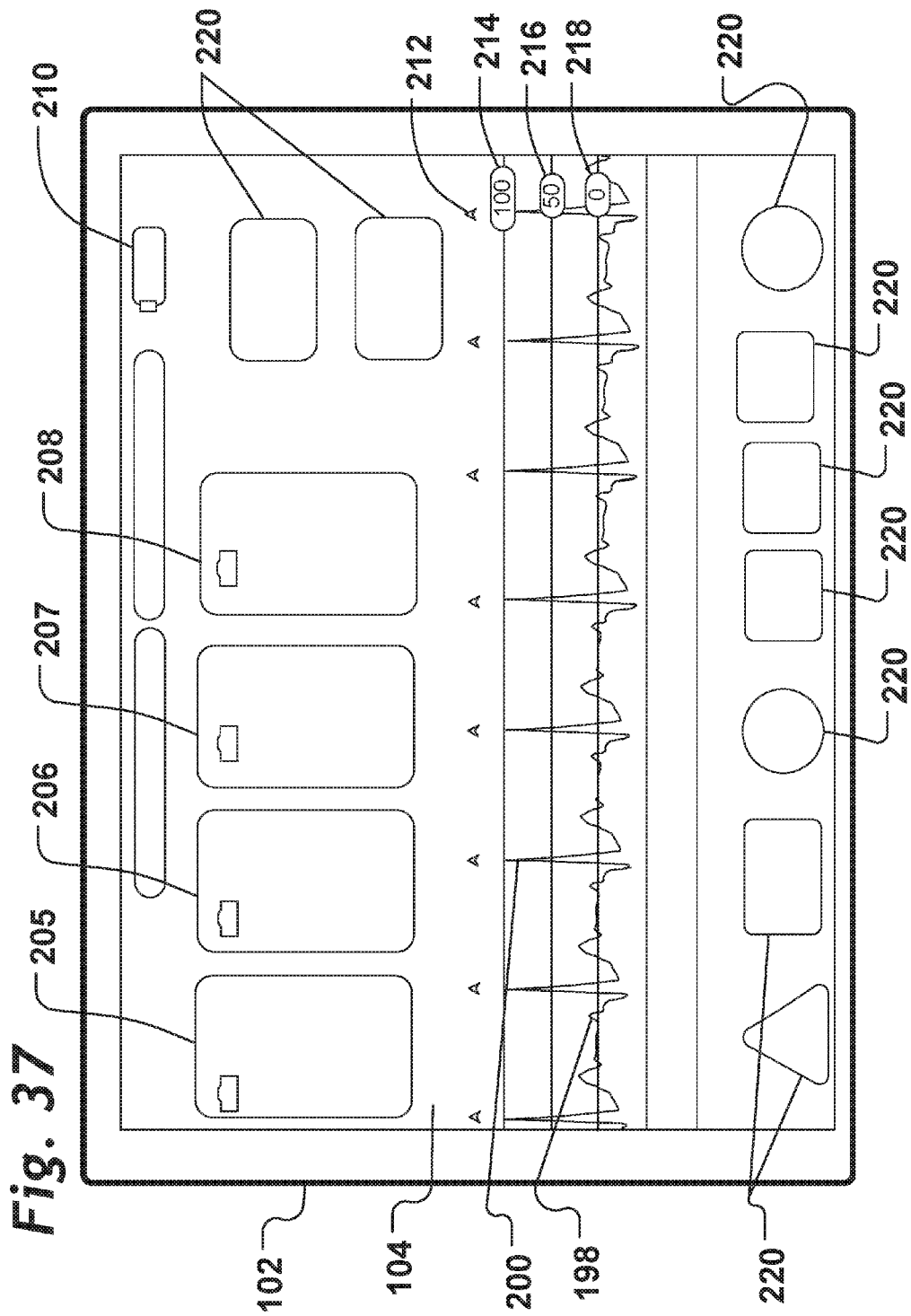
FIG. 37 is a view of a display of an exemplar of a present development hereof.

FIG. 37 is a view of a display of an exemplar of a present development hereof. This non-limiting display screen may be displayed on the touch-screen display 104 of the user control box 102. The display includes an ECG plotted over a period of time including some and or all of following features within the interface, including but not limited to: a P-wave 198, QRS complex 200, a series of screen or data capture progressions 205, 206, 207, and 208, a battery power level indicator 210, a maximum wave indicator 212, a 100% line indicator 214, a 50% line indicator 216, and a zero, 0, or baseline indicator 218. The indicator lines 214, 216, and 218 may be representative of the signal/mV (y-axis of graph) measure over time (time/s) or may be optionally indicated by another correlation of values related to the physiology of each individual. Specific algorithms may be further adapted for use in the system based on known or observed health conditions. The icons of screen captures 205, 206, 207, and/or 208 may allow the practitioner to view, review, or allow for use of the graphical user interface to capture the ECG wave form in association with placing the medical probe, stylet, catheter or guidewire in the subject. The icons, buttons, on-screen switches, and/or other inputs 220 of the graphical user interface may be enabled for the practitioner to use and document the information received, measured, and determined by the components of the medical device system.

Figure 38B:
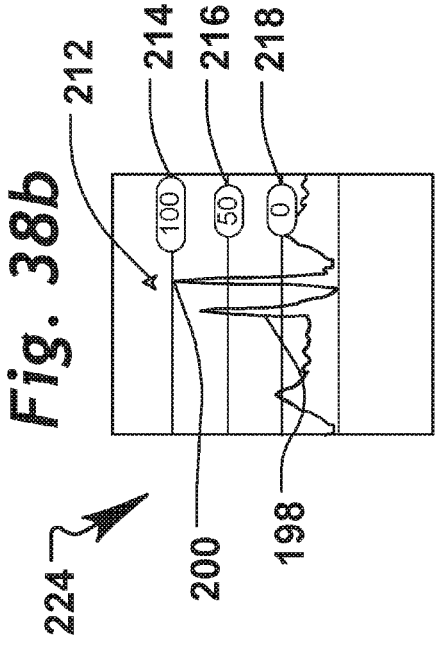
Figure 38D:
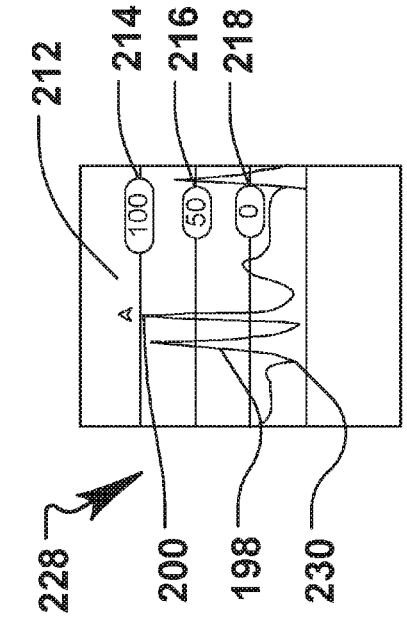
Figure 38A:
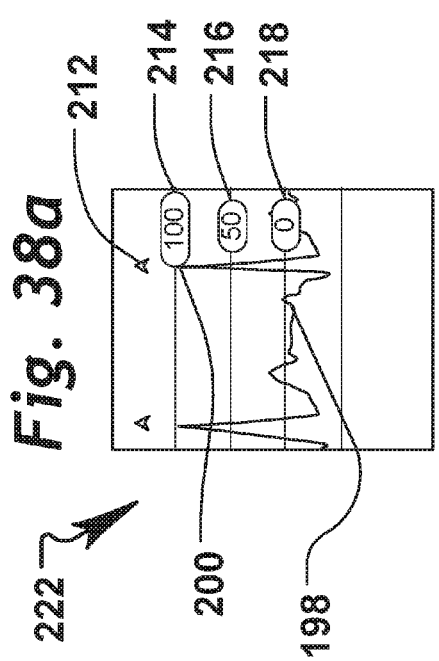
Figure 38C:
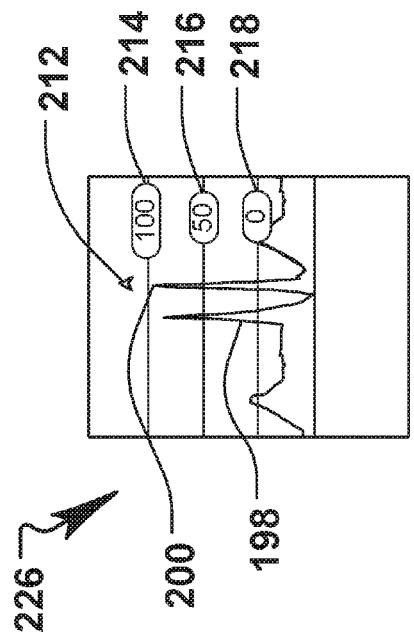

FIGS. 38a-f provide diagram, graph, and/or snapshot views of possible ECG waveforms that may be measured through the use of the ECG enabled medical probe, stylet, catheter, or guide wire. FIGS. 38a-f each provides a diagram of a measured ECG waveform which may include the P-wave 198, the QRS complex 200, a maximum wave indicator 212, a 100% line indicator 214, a 50% line indicator 216, and a zero, 0, or baseline indicator 218. FIG. 38a may be representative of a surface waveform snapshot 222 wherein the waveform displayed is a surface ECG showing normal sinus rhythm. FIG. 38b may be representative of a 75% P-wave snapshot 224, wherein the ECG measurement is received, measured, and determined using the core wire (not separately labeled in FIGS. 38a-f) to provide one lead of the ECG system. FIG. 38c may be representative of a 90% P-wave snapshot 226, wherein the ECG measurement is received, measured, and determined using the core wire to provide one lead of the ECG system. FIG. 38d may be representative of a 90% P-wave snapshot 228 and negative deflection of or prior to the P-wave 230, wherein the ECG measurement is received, measured, and determined using the core wire to provide one lead of the ECG system. When used in association with the electromagnetic locating device as further described herein, the ECG system may be used to locate, position, and adjust the invasive medical probe, stylet, catheter, or guidewire described herein. The snapshot or image or FIG. 38d may provide information that the medical probe has been inserted or advanced past the desired location of the vena cava. In this instance, the practitioner may slightly retract the probe from the subject approximately one to three centimeters to again obtain the ECG measurement as described in FIG. 38c and the 90% P-wave snapshot 226 associated therewith. FIG. 38e may depict a 90% P-wave snapshot 226, wherein the ECG measurement is received, measured, and determined using the core wire to provide one lead of the ECG system, wherein in medical probe has been retracted slightly from the position associated with snapshot 228. FIG. 38f portrays another a possible scenario of the instance where the medical probe may be inserted or advanced to far within the subject causing a bi-phasic P-wave signal 236 to be received, measured, and determined using the ECG component disposed on probe, stylet, catheter, or guidewire.

Figure 39:
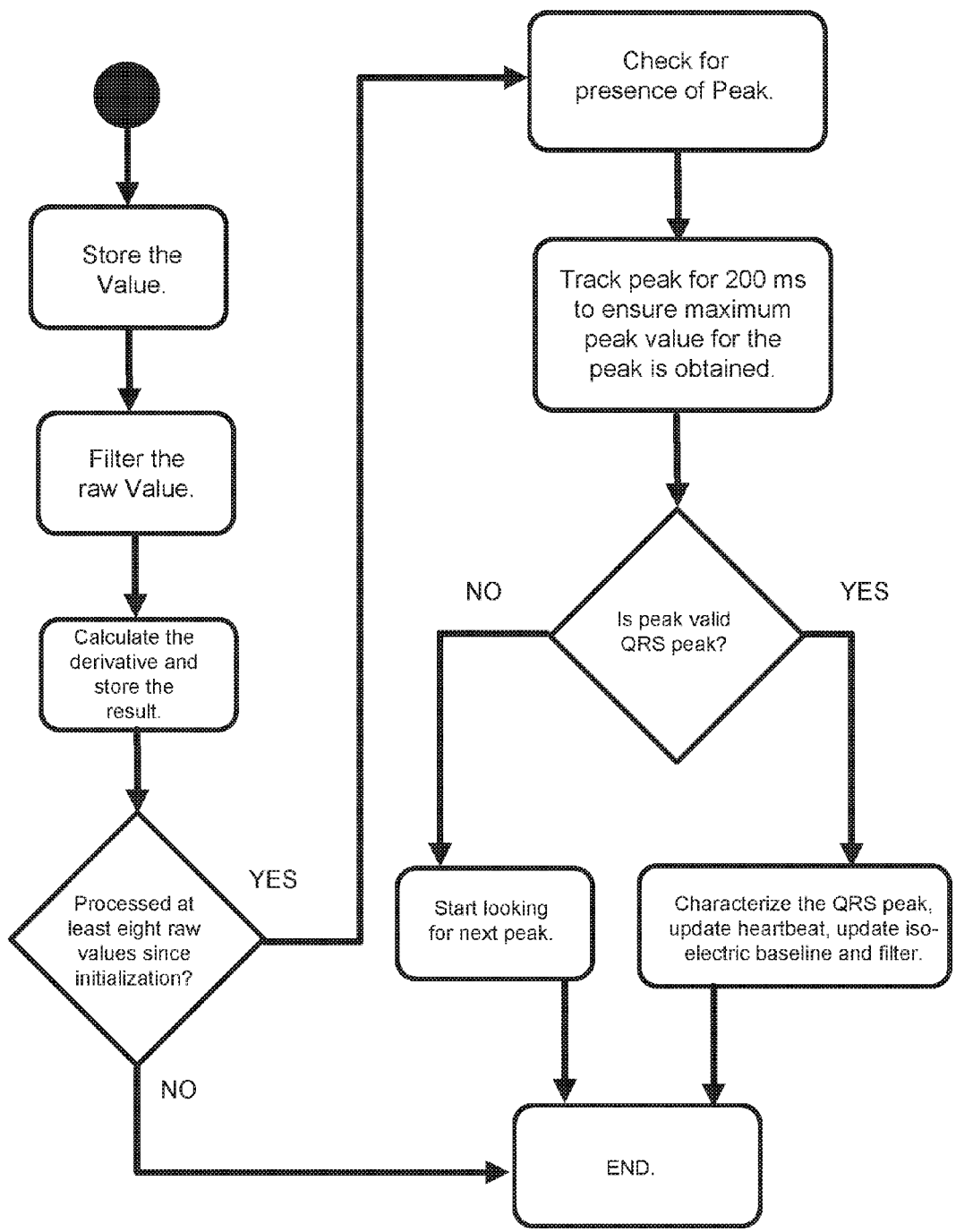
FIG. 39 is a methodology alternative for controlling one or both the acquisition and display of ECG data from the subject.

FIG. 39 is a methodology alternative for controlling one or both the acquisition and display of ECG data from the subject. This non-limiting methodology may provide a method from which the ECG data may be used to further provide accurate and timely data with the other apparatus and methods as described herein.

FIGS. 40a-c are various views of the display of an exemplar of some present developments hereof. FIG. 40a-c provide for a basic user interface display screens to assist a user or practitioner in one portion of the procedure of placing an invasive medical device within a patient. These non-limiting embodiments enable the user to make a surface measurement, cut the medical probe, stylet, catheter, or guidewire to length, determine the length that may be exposed and lastly be provided with an implanted depth measurement. In some embodiments, all of these figures may be displayed on screen for the user providing the user with easy access to display of each of the said measurements or lengths recited above. In each of the representative FIGS. 40a-c, the user control box 102 may house a display 104 which may provide navigation arrows 240, an enter or proceed button 242, FIG. 40a, may be representative of the layout 234 of the display features relevant to assisting in the measurement, calculation, and application of the implanted depth. FIG. 40a specifically provides on-screen directions for the user to perform a surface measurement 238. FIG. 40b provides for the user to select a cut length 244. FIG. 40c displays the exposed length 246 and the user may provide an input corresponding to the desired length of the device not to be inserted into the subject. The result of these inputs determines the implanted depth 248. These and other variations, embodiments, and developments may provide useful implementations of the present systems, apparatuses and/or methods.

Figure 41:
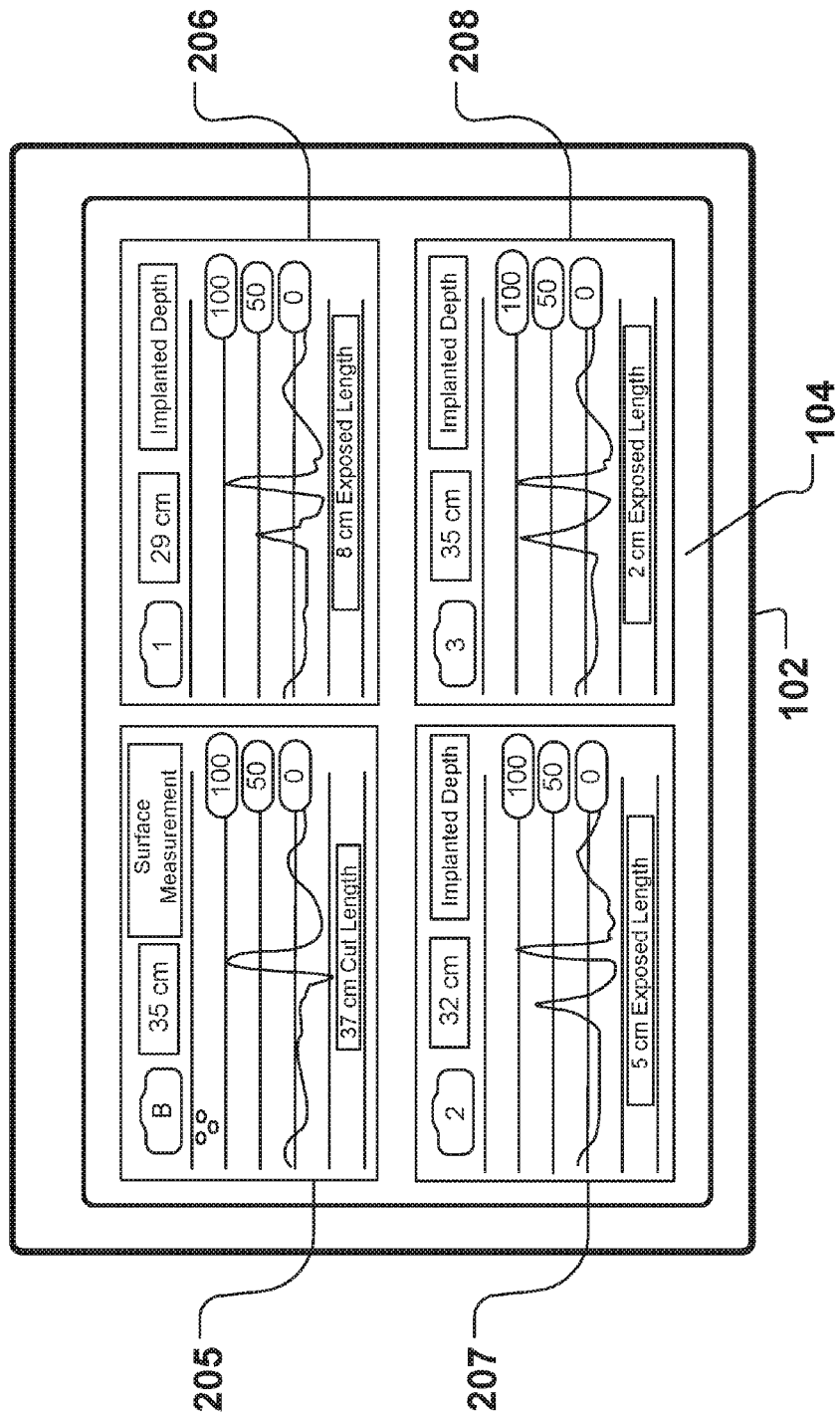
FIG. 41 is a view of a display of an exemplar of some present developments hereof.

FIG. 41 is a view of the display of an exemplar of a present development hereof wherein all diagram, graphs, or snapshots of the received, measured, determined, and recorded ECG associated data displays 248 are displayed in one display screen. These diagrams, graphs, or snapshots may optionally be printed, stored, or recorded for ensuring quality and may be used to compare to each other. The icons, displays, screen captures, or snapshots 205, 206, 207, and/or 208 may allow the practitioner to view, review, or allow for use of the graphical user interface to capture the ECG wave form in association with placing the medical probe, stylet, catheter or guidewire in the subject.

Figure 42A:
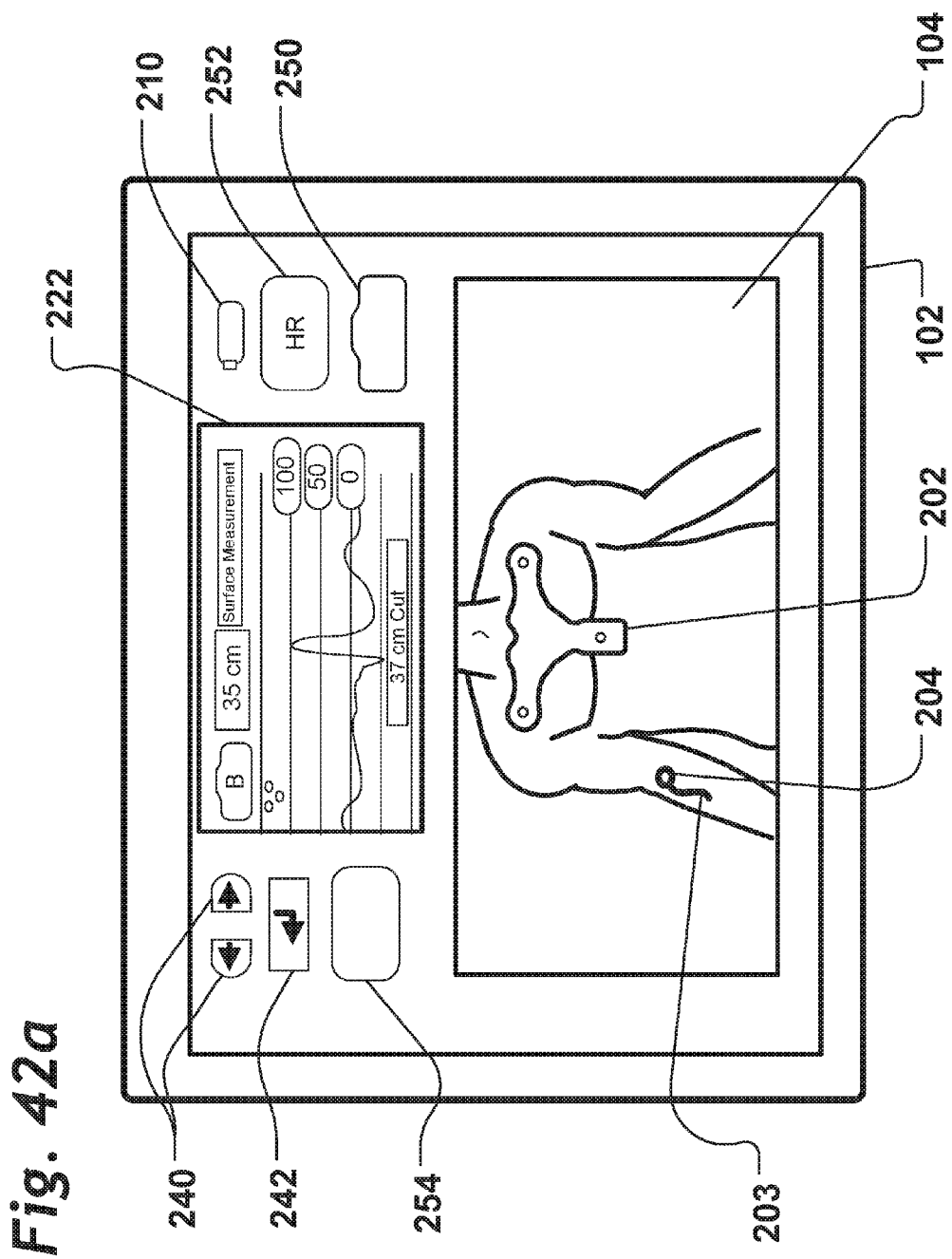
Figure 42B:
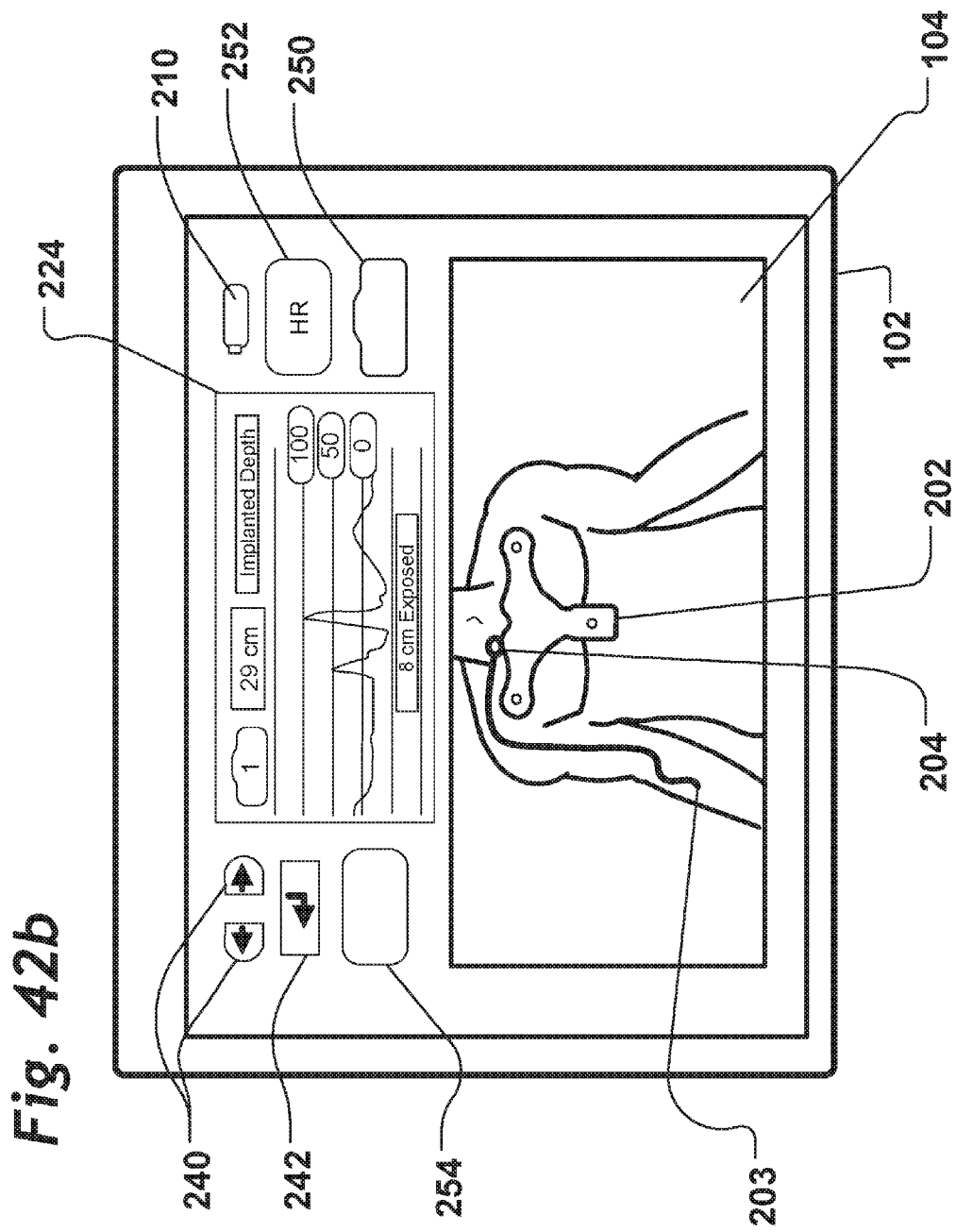
Figure 42D:
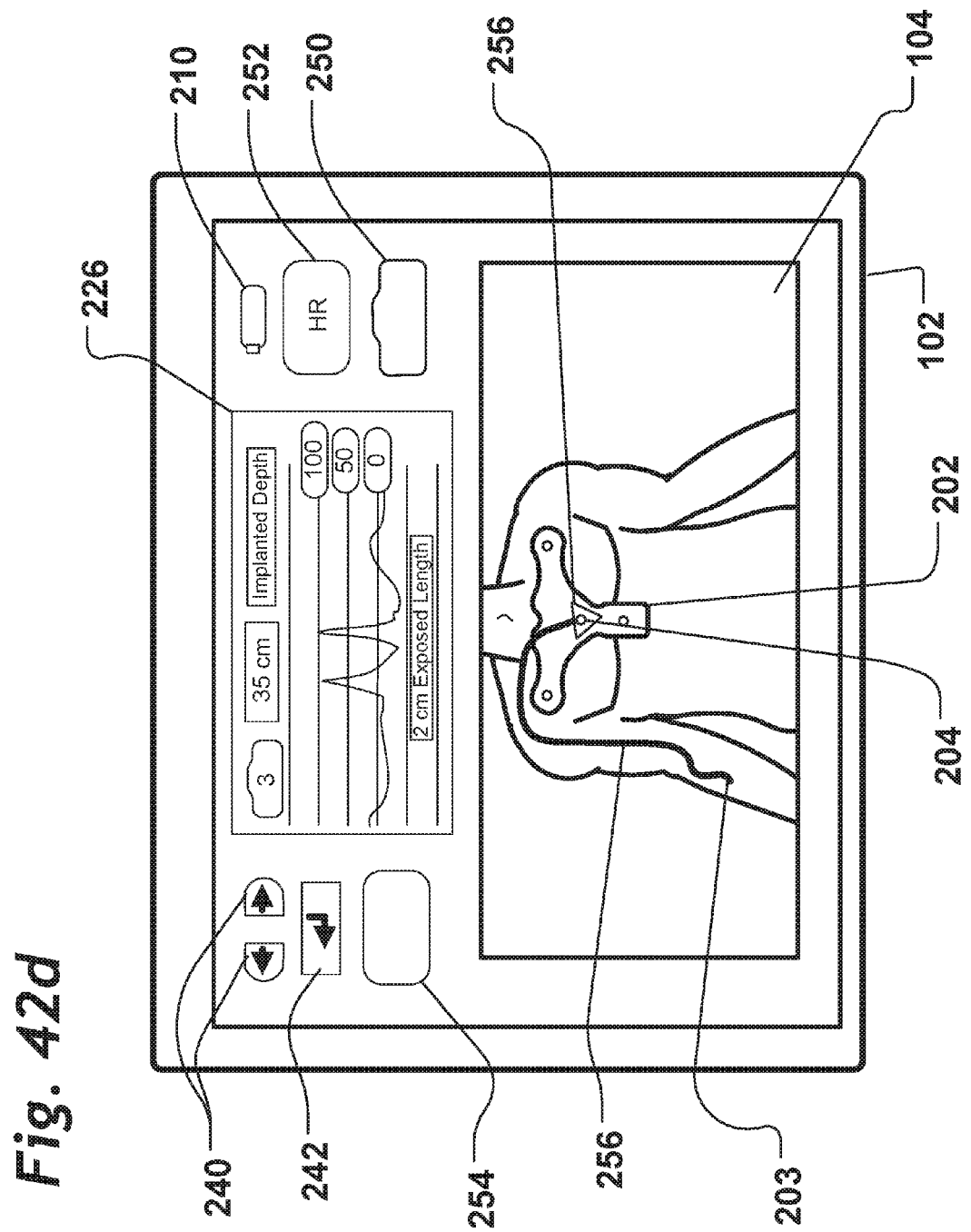

FIGS. 42a-d are various views of the display of an exemplar of some present developments hereof. Each of FIGS. 42a-d may provide for the simultaneous display of data collected from both the ECG signals of the system components and the position of the sensor coil through apparatus, methods, and/or systems hereof. The user control box 102 may contain a display 104 further including one or more icons, graphs, representations, and an interface for further operation of the developments and embodiments disclosed herein. Each of the FIGS. 42a-d include a non-limiting embodiment of the display of: the patient drive block 202; the reference trail 203; the distal end of the medical probe, stylet, catheter, or guidewire 204; navigation buttons 240; an enter, confirm, or proceed button or icon 242; a battery meter 210; a heart rate monitor 252; a screen capture icon 250; and a menu toggle 254. FIG. 42a may provide a representation of the baseline or initial reading 222 (see FIG. 38a) and simultaneously displaying the location as determined from receiving, measuring and determining the location of the sensor coil. FIG. 42b may provide a depiction after the device has been inserted and advanced toward the target region, further depicting a 75% P-wave snapshot 224 (see FIG. 38b) and simultaneously displaying the location as determined from receiving, measuring and determining the location of the sensor coil. FIG. 42c may provide a representation depicting a 90% P-wave snapshot 226 (see FIG. 38c) and simultaneously displaying the location as determined from receiving, measuring and determining the location of the sensor coil. FIG. 42d may provide a representation of a final placement of the probe, stylet, catheter, or guidewire simultaneously displaying the ECG waveform and displaying the location as determined from receiving, measuring and determining the location of the sensor coil. Further 42d provides an orientation 256 which in some embodiments may be based on the direction of movement of the probe, stylet, catheter, or guidewire an may optionally be measured, provided, and determined using signals received from one or more the core wire providing ECG signals and/or the sensor coil disposition data.

A feature of the present developments may include providing an accurate system and/or method to generate a two or three-dimensional indication of one or more of location, position, orientation, and/or travel of a medical device such as a guide wire, catheter, or stylet placed within a patient. A system hereof may include a sensor coil which is disposed in or on the tip of a guide wire or stylet cable, this sensor coil being communicatively operative and cooperative with one or more components for driving coils, receiving responses and/or determining position; these components being in or defining in some implementations an external control and/or display box which may also be communicatively connected with an array of three-axis, four-axis, or a multiple array of axes drive coils. The sensor coil hereof may be fixated in physical association with the core wire 138 wherein the sensor coil and core wire collectively comprise a sensor probe. The core wire may be electrically isolated from the sensor coil such that the core wire may provide a response signal in response to electrical stimuli of the subject. The electrical response signal generated by the conductive core wire may be indicative of the location relative to known signals produced within a subject as the probe is advanced toward in organ. In one non-limiting embodiment, the core wire may be used to receive signals for use in an ECG. Collectively, the core wire signals and the sensor coil may be referred to as a sensor probe, a medical probe, or elongate flexible probe. Accordingly, this system may in some implementations, simultaneously display the ECG of the subject, the location and/or travel of the device. The conductive core wire may be used to receive and transmit electrical signals enabling successive measurements. The successive measurements may enable the observation of common ECG waveforms, including the P-wave and the QRS-complex. The successive measurements through the conductive core wire in and response signals from the sensor coil may provide for increased accuracy and precision of placement. The accuracy of the location of the medical probe may be increased based on the measured ECG and based on patterns or features unique to each individual subject's physiology. Furthermore, the detection of the location may be more accurate because of the placement of the drive block with anatomical features of the subject providing the practitioner with a display of the location of the sensor coil in relation to a known placement of the drive block on the subject's chest. In some non-limiting embodiments, the sensor coil may be responsive to electromagnetic fields up to thirty-six inches from the centroid of the array of drive coils. The centroid is defined as the point where the three medians of the triangular shaped drive block would intersect. A median of the triangular shaped drive block is a line segment from one vertex, or corner of the triangular shaped drive block to the midpoint on the opposite side of the triangle.

The array of drive coils may be placed, in some implementations, in a triangular block on the patient's chest. This is also sometimes referred to as a drive block, an emitter block, or patient drive block. In some embodiments, the location and travel may be displayed in two locations; both on the display of the control box and/or on a display or indicator contained in the patient drive block component. The block may alternatively include or contain the coil-drive controller that facilitates driving single coils, pairs of coils, triplets of coils, quadruplets of coils, or sets of five or more coils together. In one implementation of a triplet of coils, in which a pair of coils is driven, the paired driving allows x-y, x-z, or y-z coils in a corner, i.e., in any particular set 106 of coils, to be energized at the same frequency and same power creating a virtual drive axis at a 45-degree angle between the axis pairs. The coil-drive may also have an additional control to invert the drive waveform (shift the phase 180 degrees). This inversion of one coil in the pair may create a virtual drive axis at −45 degrees, thus creating an orthogonal pair of virtual axes within a plane. For example, the virtual x-y and x-(−y) are in the same plane as the x and y axes but rotated 45 degrees within the plane. This paired drive scheme may assist in improving the measurement accuracy of the system, especially when the sensor coil inside the catheter tip is substantially or exactly perpendicular to a normal coil drive axis. The system controller may sequentially drive/energize each coil, then each pair of coils while measuring the sensor coil response. When the sensor coil is nearly perpendicular to a drive axis there is significantly diminished response; thus, the virtual axis measurement will provide more accurate data for the position algorithm. Algorithms within the controller may be used to select the best data sets—regular x-y-z axis or virtual x-y-z axis, or a combination thereof—to calculate the sensor/medical device (e.g., catheter tip) location, position and/or orientation. A display may be used to show the catheter tip location as a position track of x-y location plotted over time plus an indicator for the z-axis, depth of the catheter. In other embodiments, a display may be used to show the catheter tip location as a position of x-y location plotted over time plus an indicator for lateral view or "depth" view as a position of y-z location plotted over time. Depth can also be indicated by a variety of methods, as for example by thickening the position line segment in the plot as z decreases and thinning the position line segment as z increases. Moreover, the display may be operably programmed to automatically scale or zoom as the sensor coil approaches a designated target placement location chosen on the display by a default computer setting or a user inputted x-y-z location. In other alternatives, the external control box or the drive block may provide an audible response or command concerning the location, position, or orientation of the sensor coil.

A feature of this system includes an electrocardiogram (ECG) measurement and display with the location system. Here two, or more reference electrodes may be plugged into or otherwise connected to the display unit or patient block with the additional electrode connected to the stylet or guide wire or catheter. An ECG may then be displayed for the user, so that P-wave changes, or other waveform changes may be shown to indicate proximity of the stylet or guide wire or catheter to the heart. In one embodiment, a medical probe, as described above may be embodied in a stylet, catheter, or guidewire assembly wherein an elongate cylindrical wire is adapted for placement in the vasculature of a subject wherein the core provides an electrical pathway for the ECG signal of a node of the patient's heart. In some instances, the elongate cylindrical wire may act as the electrical pathway for an ECG and further enable the assembly to be configured in such fashion that the sense coil is wrapped around and disposed to the ECG wire. In some instances the optimal placement of the guidewire, stylet, and/or catheter is just above the right atrium of heart. This placement may be confirmed by measuring both the ECG P-wave and through the measurement and determination of location of one or more sensor coils. The ECG P-wave, QRS complex, and the electrophysiology of the heart differs between individuals; this information when coupled with a sensing coil can provide real-time information for placement, adjustment of placement, or repositioning.

The medical probe may include a core wire and sensing coil (also referred to as a sensing member) for detecting the location of the distal end position in the subject. The medical probe comprises a proximal and a distal end. For sake of clarity, the proximal end is the end closest to the user or connected to the control box and the distal end is the end which is inserted or disposed in the subject. The one or more sensing members and/or coils may be disposed substantially toward the distal end of the probe and provide response signals for detecting the location of the probe's distal end position as it travels through the subject. The sensing member and/or sensor coil may be comprised of fine wires composed of copper or another suitable material wrapped around a magnetically semi-permeable conductive core wire. The core wire may be a material selected from the group consisting of metglas, iron, nanoperm, mu-metal, cobalt-iron, permalloy, ferrous stainless steel, and ferrite. The shape of the core wire may be selected from the group consisting of a circle, an ellipse, a square, a pentagon, a hexagon, an octagon, or another shape. The fine wires for the sensor coil may be wrapped around the core wire in one or more overlying layers. The sensing member may be operatively communicative to measure the magnetic field from an array of drive coils placed relative to the subject's body. In one embodiment, the medical probe may have a total outside diameter of less than about 0.014 inches. This total outside diameter is inclusive of the conductive core wire, the fine wires adapted for use as a sensor coil, and any insulation or bio-compatible sealings, sheathings, jackets, films, or additional materials known in the art to provide the necessitated bio-compatibility.

An elongate flexible tubing or catheter may be used in conjunction with medical probe wherein the medical probe inclusive of the electrical pathway responsive to electrical stimuli (ECG) and sensor coil are disposed within the flexible tubing. The catheter may have one or more lumens or channels for housing one or more medical probes. The lumen on the catheter may be sized appropriately to aid the medical probe to the desired location identified by the practitioner. The size and shape of the lumen may aid the practitioner in both retracting the medical probe to inside the lumen and then extending the medical probe to a fixed position. The medical probe or probes may be retracted completely or may be removed from the catheter completely after the catheter has been placed by the practitioner.

In a non-limiting alternative embodiment, the medical probe may have more than one sensor coil disposed in physical association with different portions of the conductive core wire. The second sensor coil may provide additional information related to the position of the medical probe within the subject. Additionally, in a non-limiting embodiment the sensor coils may be placed a known distance apart along the length of the elongate flexible core wire. In this way, the sensor coils may necessarily provide different response signals for the determination of the disposition of the core wire within the subject.

The z-axis (depth) may have particular importance in or for determining the implanted depth and therefore be important for proper placement of the medical device, as for example a catheter. Issues have existed in determining accurate location of the z-axis. Particularly, calculations of the z-axis have been difficult because null sensor coil response values appear in sensing the magnetic field when the sensor coil is approaching a perpendicular orientation to the z-axis drive coils. One alternative implementation of a system includes a quadruplet of coils in each corner of the patient drive block (i.e., a quadruplet in each set 106 of coils, each set also defining or being in a "corner" of the triangle, or trilateration disposition established by the patient drive block) wherein two axes are orthogonally arranged in the z-dimension, referred to as z'-axis and z"-axis. In this system a pair of coils are driven, the paired driving allows x-y, x-z', x'-z", y-z', y-z", and z'-z" coils in a corner (or respective set 24) to be energized at the same frequency and same power creating a virtual drive axis at an angle between the axis pairs.

It is possible to extend this system further using programmable current control to the coil-driver circuit. Here, a virtual axis could be created at any angle between a drive coil pair in a corner (or respective set 106) by energizing two electromagnetic coils at the same frequency but with different current drive (power levels to yield a vector-sum virtual axis at any angle between 0 and 90 degrees and inverting one coil in this drive scheme to yield a vector-sum virtual axis at any angle between 0 and −90 degrees). However, an orthogonal set of axes would typically still be selected to accurately locate the sensor coil. A further extension to this system could include energizing all three electromagnetic coils, x-y-z, together in a corner using the programmable current controls and inversion controls. The result here would be a vector sum from x-drive, y-drive, and z-drive coils that creates a virtual drive at any vector within three-dimensional space. Alternatively, the system could include energizing all four coils, x-y-z'-z", together in a corner using the programmable current controls and inversion controls. In alternatives that include four coils in a corner (or set 106), the result would be a vector sum from the x-drive, y-drive, z'-drive, and z" drive coils that creates a virtual drive at any vector within three-dimensional space from these coils.

An aspect of the present developments is an electromagnetic medical device locating system for locating a medical device or the end or the tip thereof in a subject, including one or more of three or more triplet drive coil sets, each drive coil set including at least three orthogonally arranged discrete drive coils, each of the discrete drive coils being electromagnetic (EM) coils. The system further includes at least one moveable sensor coil, and one or more system components that one or both provide drive signals energizing said discrete drive coils and measure resulting sensor coil response signals. The provision of drive signals includes one or both of (i) sequentially driving one or pairs of said discrete drive coils within a triplet drive coil set, and (ii) selectively providing phase inversion of the drive signal to any one or pairs of said discrete drive coils within a triplet drive coil set. The system further includes a determining component for calculating sensor coil disposition in the subject relative to said triplet drive coil sets from one or more measured resulting sensor coil response signals.

Another aspect of the present developments may be inclusion of a digital signal processor operably configured to modify said AC drive frequency to one or both maximize and optimize the output from the discrete drive coils. Additionally, the system may include a demodulator for selectively measuring said sensor coil response signal. The demodulator further processes the sensor coil signal and controls a demodulator clock that operates at the same frequency as the coil AC drive signal with a phase offset. The digital signal processor controls the demodulator clock to one or both maximize and optimize the drive coils thus one or both maximizing and optimizing the sensor coil response signal. Further, the digital signal processor may be connected to non-volatile memory capable of storing: data necessary for controlling the coil clock frequency data for input to the array of drive coils and data for controlling the frequency and phase data for the demodulator clock.

Another aspect may include: (a) three or more virtual or actual x-y-z axis electromagnetic (EM) triplet drive coils, each including at least three virtual or actual EM drive coils arranged in perpendicular axis to each other along an x-y-z axis, the virtual or actual EM triplet drive coils placed in a two- or three-dimensional geometric array; (b) at least one medical device sensor coil in physical association with at least one medical device tip and connected to at least one demodulator circuit; (c) at least one AC drive controller that (i) drives sequentially one or more of the virtual or actual EM drive coils; and (ii) provides a phase shifted signal to the demodulator; (d) at least one demodulator circuit including at least one demodulator for measuring the sensor coil output signal using frequency correlation with at least one AC coil driver signal from the AC drive controller to provide a synchronously demodulated sensor coil signal; (e) at least one automatic gain control circuit that maximizes the demodulated sensor coil signal; (f) a computing component for normalizing the resultant demodulated sensor coil signal data by dividing or multiplying the determined programmable gain value from the measurement of the demodulated sensor coil signals; (g) a computing component for selecting and calculating the optimized demodulated sensor coil signal data set generated from demodulated sensor coil signals, which optimized coil signal data set is calculated based on the sum of measured squared terms that have relatively higher or highest values; (h) a calculator for calculating the distance of the moveable sensor coil and medical device tip from three or more virtual or actual EM triplet drive coil locations using the optimized demodulated sensor coil data set calculated using intersection of the spheres to provide the location of the sensor coil and corresponding medical device tip in space relative to the location of two or more of the virtual or actual EM triple drive coils provided in the two- or three-dimensional geometric array corresponding to the location of the medical device tip in the subject; and in some implementations, (i) a display. The result is the actual location of the medical device tip in the subject indicating height, width, and depth of the medical device tip in the subject calculated relative to the position of the drive coil geometric array.

It is possible to extend this system to include one or more of (i) the virtual or actual EM drive coils or the virtual or actual EM triplet drive coils are arranged outside at least one of a two dimensional plane defined by at least three of the virtual or actual EM triplet drive coils; and/or (ii) at least four of the virtual or actual EM triplet drive coils form a tetrahedron as part of the three-dimensional geometric array.

It is possible to enhance such a system to include one or more of wherein (i) the display shows the relative location of the sensor coil or the medical device tip as a tracking of the sensor coil or medical device tip location over time; (ii) the display displays the sensor tip angle graphically for the user of the system, wherein the medical device tip angle is the angle of maximum response of the sensor coil as measured from sweeping the virtual drive axis through x-y plane (e.g. 0 to 360 degrees) then using this x-y maximum response angle as a vector added to the sweep through the virtual z axis; and/or (iii) the display displays the sensor tip angle graphically for the user of the system, wherein the medical device tip angle is the angle perpendicular to the angle of minimum response of the sensor coil as measured from sweeping the virtual drive axis through x-y plane (e.g. 0 to 360 degrees) then using this x-y minimum response angle as a vector added to sweep through the virtual z axis.

It is possible to extend such a system to further include wherein the intensity or power of current running through one or more adjacent EM drive coils in at least one of the EM triplet drive coils is programmable or adjustable using a control box including a programmable computer.

An aspect of the present developments is to provide a system wherein one or more of the EM drive coils are provided as the virtual EM drive coils, and wherein: (a) one or more controllers that select pairs or triplets of drive current values of the EM drive coils at regular time intervals to provide one or more paired magnetic drive coil vector values at angles from 0 to 90 degrees and phase inversion of at least one of the corresponding EM drive coils in at least one pair of the paired or tripled magnetic drive coil vectors to further provide one or more magnetic drive coil vector values at angles from −90 to 0 degrees; (b) one or more controllers that: (i) determine the angle values of maximum and minimum sensor coil responses within a plane using paired coil programmable current drive sweeping a range from 0 to 90 degrees; and (ii) that then determine the angle values of maximum and minimum sensor coil responses within a plane using paired coil programmable current drive sweeping using inverted phases of at least one coil and sweeping a range from −90 to 0 degrees; and/or (c) a calculator that: (i) computes at least one set of optimal virtual drive x and y axes for at least two of the EM triplet drive coils as values corresponding to plus and minus 45 degrees from the maximum and minimum sensor coil responses; and (ii) computes an optimal virtual drive z axis orthogonal to the plane of the optimal virtual drive x and y axes to provide at least one optimal virtual EM triplet drive axes and at least one of the virtual EM triplet drive coils. This aspect can be further extended to systems that utilize a quadruplet of drive coils.

Such a system may be extended wherein the system includes a programmable coil drive current for each of x, y, and z drive coils driven; and wherein (a) the triplets of drive current values selected at regular time intervals are provided as (i) paired magnetic drive coil vector values at angles from 0 to 90 degrees in an x-y plane together with 0 to 90 degrees from the x-y plane to the corresponding z-axis; and (ii) as phase inversion of one or two paired magnetic drive coil vector values at angles from −90 to 0 degrees in an x-y plane together with from −90 to 0 degrees from the x-y plane to the corresponding z-axis; (b) the angle values of maximum sensor coil responses within a plane for both 0 to 90 and −90 to 0 degrees are fixed and used for at least two x and y virtual axes in a virtual plane and the values of maximum sensor coil response are determined for the corresponding virtual z axis to provide at least one maximum virtual x-y-z vector for at least one of the corresponding virtual EM triplet drive coils; (c) the angle values of minimum sensor coil responses within a plane for both 0 to 90 and −90 to 0 degrees are fixed and used for at least two x and y virtual axes in a virtual plane and the values of maximum sensor coil response are determined for the corresponding virtual z axis to provide at least one minimum virtual x-y-z vector for at least one of the corresponding virtual EM triplet drive coils; (d) the at least one optimal virtual EM triplet drive vector and at least one of the virtual EM triplet drive coils are generated using intermediate virtual drive x and y axes as plus and minus 45 degrees from the minimum virtual x-y-z vector and intermediate virtual drive z axis as orthogonal to the intermediate virtual drive x and y axis; the optimal virtual x, y, and z axis are then generated by pivoting the intermediate x, y, and z axes by moving the intermediate z axis 45 degrees about the maximum virtual x-y-z vector. This aspect can be further extended to systems that utilize a quadruplet of drive coils.

Such a system may be enhanced wherein the display further displays P-wave or other cardiac waveform changes over time in combination with the location of the medical device tip in relationship to the subject's heart.

Such a system may be extended by further including (i) an x-axis tilt meter and y-axis tilt meter which uses gravity to measure the x-axis and y-axis tilt from true vertical; and (2) a computer to calculate and display the location of the medical device tip as height, width, and depth of the sensor coil corrected for the tilt the geometric array. Such a system may be enhanced wherein the geometric array and sensor coil connected to the display via a wireless interface.

Such system may be extended by further including an electrocardiogram (ECG) operably associated with the geometric array with a display to show the subject's ECG signal over time; or by further including an electroencephalogram (EEG) operably associated with the geometric array with a display to show the subject's EEG signal over time. The system could be further extended wherein the two or more of the ECG leads are operably connected to the system via a wireless connection.

Such a system may be extended by further providing indications and/or a display of the ECG waveform and particular aspects of the ECG waveform. The P-Wave and the QRS complex may be used to provide additional information and may allow for a more accurate placement when used in further association with the present developments herein. Exemplary, non-limiting display data and comparison information such as the height of the P-wave in comparison to the QRS complex can be indicative of the medical probe approaching the desired location in the subject. The system and display may provide an indication when the P-wave height has reached approximately 75% of the height of the QRS complex, when the P-wave height has reached approximately 90% of the height of the QRS complex, and when the ECG wave form includes a deflection of the wave form prior to the P-wave wherein the height of the P-wave is approximately 90% of the QRS complex height.

An aspect of the present developments may include a method for locating a medical device in a subject, including: (a) providing a system as presented herein; (b) inserting and positioning the medical device tip associated with a functional and sterile medical device into the subject; and (c) recording or monitoring the output of the display to locate the medical device tip in the subject. Such a method may be extended wherein the method further includes the use of at least one selected an electrocardiogram (ECG), an electroencephalogram (EEG), an x-ray machine, an computer assisted tomography (CAT) machine, a positron emission tomography (PET) machine, an endoscope, or an ultrasound imaging device or composition.

An aspect of the present development may include a system operably connected to an ultrasound imaging device. The ultrasound imaging device is operably connected to the control box providing a display of the vasculature of the subject. The ultrasound imaging device may be further connected to guidewires, stylets, or catheters that include biocompatible radiopaque markings at distances, lengths, or measurements, that span the circumference or a portion thereof of the guidewire, stylet, or catheter (e.g. inserted component), from the proximal to distal end of the inserted component.

An aspect of the present developments may include methods, computer systems and software, provided as programming code or instructions on computer readable media or hardware or networks or computer systems, for generating virtual electromagnetic (EM) triplet drive coils for generating data corresponding to the location coordinates for a sensor coil. The method includes electronically providing triplets of drive current values generated from at least three EM drive coils of the EM triplet drive coils in detectable proximity to the EM sensor at regular time intervals to provide one or more paired magnetic drive coil vector values generated at angles from 0 to 90 degrees without and from −90 to 0 degrees with phase inversion; electronically providing angle values of maximum or minimum EM sensor coil responses generated from the EM triplet drive coils within the x-y plane using paired x-y coils' programmable current drive sweeping a range from 0 to 90 degrees without and from −90 to 0 degrees with phase inversion; electronically computing at least one set of optimal virtual drive x and y axes as values corresponding to plus and minus 45 degrees from the maximum or the minimum sensor coil response; and electronically computing an optimal virtual drive z axis orthogonal to the plane of the optimal virtual drive x and y axes to provide at least one optimal set of virtual EM triplet drive axes for at least one of the EM triplet drive coils.

Such a method may be extended wherein (a) the triplets of drive current values selected at regular time intervals are provided as (i) paired magnetic drive coil vector values at angles from 0 to 90 degrees in an x-y plane added together with coil vectors of the z-axis from 0 to 90 degrees from the x-y plane; and (ii) as phase inversion of one or more paired magnetic drive coil vector values at angles from −90 to 0 degrees in an x-y plane added together with coil vectors of the z-axis from −90 to 0 degrees from the x-y plane; (b) the angle value of maximum sensor coil response within the x-y plane for both 0 to 90 and −90 to 0 degrees is determined as the intermediate virtual maximum x-y axis and this intermediate virtual maximum x-y axis added to the z-axis swept from 0 to 90 and −90 to 0 degrees to determine at least one maximum virtual x-y-z vector for at least one of the corresponding EM triplet drive coils; (c) the angle value of minimum sensor coil response within the x-y plane for both 0 to 90 and −90 to 0 degrees is determined as the intermediate virtual minimum x-y axis, and this intermediate virtual minimum x-y axis is added to the z-axis swept from 0 to 90 and −90 to 0 degrees to determine at least one minimum virtual x-y-z vector for at least one of the corresponding EM triplet drive coils; and (d) the at least one optimal virtual EM triplet drive axes for at least one of the EM triplet drive coils are calculated using the plane defined by the maximum virtual x-y-z vector and minimum x-y-z vector wherein the optimal virtual drive x and y axes are plus and minus 45 degrees from the minimum virtual x-y-z vector and the optimal virtual drive z axis as orthogonal to the optimal virtual drive x and y axes.

In some developments, each coil set 106 could be mounted as feet protruding from the bottom of the block 122. The sensor coil 114 is built onto a small diameter biocompatible cable 118 which may be inserted into a medical device such as a catheter to be placed in the patient. The sensor signal is connected back to the control box 102 with a two-wire cable 120. FIG. 7 provides a detailed view of a sensor coil 114. Sensor coil performance may be improved by winding the coil about a ferromagnetic wire in the tip of the cable 138. The ferromagnetic material should be used for the length of the sensor coil 114 and may be followed by non-ferrous material. Two fine wires 142 from the sensor coil 114 are attached or associated (e.g., glued, wrapped, insulated, and or sheathed) and sealed 140 down the length of the ferrous core wire 138.

As presented, e.g., in FIG. 18, an aspect of this device may include continuous display at the position of the sensor coil 114 placed in the tip of a medical device as the medical device moves through the patient's tissue. The patient drive block 122 is placed over the patient's body where the medical device will be targeted (e.g., over the chest preferably aligned with the sternal notch if the medical device will be placed in the area of the heart).

As presented, e.g., in FIGS. 1, 16, 17, and 18, respectively, the sensor coil cable 120 and patient drive block cable 108 are connected to a user control box 102. The user control box 102 contains a computer 156 (FIG. 10) which sequentially drives each driver coil 126, 128, 124 (FIG. 2) on each axis in every corner 106a, 106b, 106c of the patient drive block 122, 150. The coil driver creates magnetic drive vectors as shown in FIG. 9, 10, or 11—where FIG. 9 represents normal drive and FIGS. 10 and 11 represent virtual drive. The single board computer 166 (FIG. 21) measures the demodulated output signal from the sensor coil 114 for each sequentially driven coil set 106 (FIG. 1). The single board computer 156 (FIGS. 16 and 21) continuously adjusts the gain of each output signal using a programmable gain stage in the demodulator electronics and scales all the sensor data to be gain normalized (see FIG. 25b, 25c, inter alia). Here, gain normalized means that if a measured response is value "a" collected at a programmable gain of "4.00" times, then the normalized resultant value is "a" divided by 4.00. A non-limiting example of an alternative gain normalizing method is to multiply each value "a" by 4096/gain, e.g. "a"×4096/4.00. The programmable gains that may be used as a non-limiting example are 1.00, 2.00, 4.00, 8.00, 16.00 and 32.00 plus there may be a final gain stage that is selectable for 1.00 or 1.41 (equivalent to $1/\sqrt{2}$). Examples of a resultant set of programmable gains are 1.00, 1.41, 2.00, 2.82, 4.00, 5.64, 8.00, 11.28, 16.00, 22.56 and 32.00.

From the normalized response data, the single board computer 156 (FIG. 21) compares the sum of the squares of the sensor's normal response to the sum of the squares of the sensor's virtual response. Whichever sum is greater or has the stronger response may be used by the computer 156 to calculate the sensor coil 114 location using trilateration which is the calculation of the intersection of three spheres where each sphere is defined as the radial distance of the sensor coil 114 from each x-y-z driver coil set 106a, 106b, 106c (FIG. 1).

From each corner, the radial distance can be defined as a constant divided by the $6^{th}$ root of the sum of the squares of the x, y, and z measured normalized response. Here the constant, k, is a calibration constant reflecting the strength of each drive coil 124, 126, 128 (FIG. 2) and the sensitivity of the sensor coil 114 (FIG. 1). In one possible aspect, a calibration constant could be generated during manufacturing for each of the drive coils and then stored as calibration constants for each coil in non-volatile memory of the patient drive block. By trilateration, the radial distance equation for each corner is:

$$r = k/\sqrt[6]{(x^2+y^2+z^2)}$$

The sensor coil location is then calculated from three equations for the three corners of plate 122:

$$r_1^2 = k^{2/3}\sqrt{((x_1^2+y_1^2+z_1^2))}$$

$$r_2^2 = k^{2/3}\sqrt{((x_2-d)^2+y_2^2+z_2^2)}$$

$$r_3^2 = k^{2/3}\sqrt{(x_3^2+(y_3-d)^2+z_3^2)}$$

Here d is the distance of each coil from the other and k is the calibration constant which scales the result into meaningful units of distance, e.g. centimeters or inches. In this non-limiting example, the coils on the patient drive plate or block 122 (FIGS. 1, 16, 17 inter alia) are arranged in a right triangle, with two sides of equal length, d, as reflected in the $2^{nd}$ and $3^{rd}$ equations above, just on different axis, x or y. The solution to these equations yielding the sensor coil location is:

$$x_S = (r_1^2 - r_2^2 + d^2)/2d$$

$$y_S = (r_1^2 - r_3^2 + d^2)/2d$$

$$z_S = +/-\sqrt[2]{(r_1^2 - x_S^2 - y_S^2)}$$

Here the solution for z (vertical axis) is assumed to be negative as the sensor coil 114 cannot be above the plane of the patient drive block 122 (FIGS. 1, 16, 17, 18, 19 inter alia) unless it is outside the patient.

While the above reflects one non-limiting approach to locating the sensor coil 114 (FIG. 1), it is not the only solution for coil location. Specifically when the sensor coil 114 is nearly perpendicular to a driver coil axis the sensor coil response approaches zero; therefore a "virtual axis" drive system, in some instances, provides for the optimal sensor coil response. In this approach the coil driver circuit is designed to selectively drive, within a triplet set, pairs of coils, e.g. 124 and 126 (FIG. 2), together at the same frequency and amplitude with an additional driver control to selectively invert the phase of one coil in the pair. This paired coil drive of x-y coils creates the 1st virtual axis at forty-five degrees from the original x and y axes. The paired coil drive is then operated with x-(-y) which drives the x-coil together with inverted-phase y-coil and this creates the $2^{nd}$ virtual axis at minus forty-five degrees from the original x and y axes. The result is two orthogonal virtual magnetic vectors as shown by the dashed lines in FIG. 9 for x-y paired coil drive or in FIG. 10 for y-z paired coil drive. For paired drive, the single board computer 156 (FIG. 16) sequentially drives the x-y pair, x-(-y) pair, and z axis for each x-y-z coil set 106a, 106b, 106c (FIGS. 1 and 7). Here, "(-y)" means inverted phase on y axis drive. The measured sensor coil response for paired-coil drive must be scaled down by $\sqrt{2}$ or 1.4142 because of vector summing of the two coils driven together. Alternatively, the coil-driver power could be scaled down by $1/\sqrt{2}$ or 0.7071 in hardware when driving pairs so that the vector sum of two coils equals the magnetic vector of a single coil drive. The single board computer 156 measures the sensor coil response for each corner in normal drive and paired drive, and then selects the strongest signal from each corner comparing the sum of $x^2$, $y^2$, and $z^2$ normal coil drive response to the sum of $(x-y)^2$, $(x-(-y))^2$, and $z^2$ paired coil drive response. The strongest signal from each corner is used to calculate the location of the sensor coil 114 using the trilateration method described in the above equations. This example illustrates paired x-y coil drive; and by logical extension this may also apply to x-z, or y-z paired drive. An objective in some implementations of these developments may include improving the accuracy of horizontal (x-y) location; therefore the paired x-y drive can be preferred over x-z or y-z.

In an alternative embodiment and/or method, the single board computer 156 (FIG. 21) uses the normalized response data to compare the sum of the squares of the sensor's normal response to the sum of the squares of the sensor's virtual response. Whichever sum is greater or has the stronger response may be used by the computer 156 to calculate the sensor coil 114 location using trilateration which is the calculation of the intersection of three spheres where each sphere is defined as the radial distance of the sensor coil 114 from each x-y-z driver coil set 106a, 106b, 106c (FIG. 1).

In this alternative embodiment, from each corner, the radial distance may be defined as a constant divided by the 6$^{th}$ root of the sum of the squares of the x, y, and z measured normalized response. Here the constant, k, is a calibration constant reflecting the strength of each drive coil 124, 126, 128 (FIG. 2) and the sensitivity of the sensor coil 114 (FIG. 1). In one possible approach, a calibration constant could be generated during manufacturing for each of the drive coils and then stored as calibration constants for each coil in non-volatile memory of the patient drive block. By trilateration, the radial distance equation for each corner is:

$$r=k/^6\sqrt{((x^2+y^2+z^2))}$$

In this approach for calculation of the EM tip location, by trilateration, the sense coil location [x, y, z] distance equation for each corner is:

$$xs=(r_1^2-r_2^2+d^2)/(2d)$$

$$ys=[(r_1^2-r_3^2+i_2+j^2)/(2j)]-[(i/j)\cdot xs]$$

$$zs=+/-\sqrt{[r_1^2-xs^2-ys^2]}$$

In this alternative, the coordinates of the sphere used for trilateration may be as follows: sphere 1=[0,0], sphere 2=[0,d], and sphere 3=[i,j]. One should note that there are two solutions to the zs answer, in this instance, the "+" and the "−" solution. The computer component is operably programmed to select the solution for the negative answer as the assumption is made that the sensor coil 114 cannot be above the plane of the patient drive block unless it is outside the patient. In this alternative, by trilateration, the radial distance equation for each corner is:

$$r_1^2=k/^6\sqrt{((mx_i^2+my_1^2mz_1^2))}$$

$$r_2^2=k/^6\sqrt{((mx_2^2+my_2^2+mz_2^2))}$$

$$r_3^2=k/^6\sqrt{((mx_3^2+my_3^2+mz_3^2))}$$

In this alternative, $mx_i$, $my_i$, and $mz_i$ are measured sense coil responses from corner 1 124; $mx_2$, $my_2$, and $mz_2$ are measured sense coil responses form corner 2 126; and $mx_3$, $my_3$, and $mz_3$ are measured sense coil responses from corner 3 128. Furthermore, a non-limiting approach may be implemented when the sensed or measured z-signal is approaching a null or alternatively when the measuring or determining component determines that a null signal was received. Here, the z-signal is estimated using the following:

$$mz^2((mx^2+my^2)\times(1/\sqrt{2}));$$

or, $$mz^2=((mx^2+my^2)\times(0.7071))$$

In this alternative, the location of the sense coil is calculated using the vector sums of x and y to estimate the z vector; thus, preventing the return of a null signal. In this alternative, due to the drive coil fields and due to location and spacing of the drive coils, the nulls of one corner do not overlap the nulls of another corner.

The sensor coil location is then calculated from three equations for the three corners of plate 122, in this instance substituting the above estimated z-signal in the place of the z vector, to:

$$r_1^2=k/^6\sqrt{((mx_1^2+my_1^2+((mx_1^2+my_1^2)\times(1/\sqrt{2}))}$$

$$r_2^2=k/^6\sqrt{((mx_2^2+my_2^2+((mx_2^2+my_2^2)\times(1/\sqrt{2}))}$$

$$r_3^2=k/^6\sqrt{((mx_3^2+my_3^2+((mx_3^2+my_3^2)\times(1/\sqrt{2}))}$$

The solution to these equations yielding the sensor coil location is:

$$x_S=(r_1^2-r_2^2+d^2)/2d$$

$$y_S=(r_1^2-r_3^2+d^2)/2d$$

$$z_S=+/-^2\sqrt{(r_1^2-x_S^2-y_S^2)}$$

Here the solution for z (vertical axis) is assumed to be negative as the sensor coil 114 cannot be above the plane of the patient drive block 122, 150 (FIGS. 1, 16, 17, 18 inter alia) unless it is outside the patient.

While the above reflects one non-limiting approach to locating the sensor coil 114 (FIG. 1), it is not the only solution for coil location. Specifically when the sensor coil 114 is nearly perpendicular to a driver coil axis the sensor coil response approaches zero; therefore a "virtual axis" drive system provides for an additional sensor coil response. In this approach the coil driver circuit is designed to selectively drive, within a triplet set, pairs of coils, e.g. 126 and 124 (FIG. 2), together at the same frequency and amplitude with an additional driver control to selectively invert the phase of one coil in the pair. This paired coil drive of x-y coils creates the 1st virtual axis at forty-five degrees from the original x and y axes. The paired coil drive is then operated with x-(−y) which drives the x-coil together with inverted-phase y-coil and this creates the second virtual axis at minus forty-five degrees from the original x and y axes. The result is two orthogonal virtual magnetic vectors as shown by the dashed lines in FIG. 9 for x-y paired coil drive or in FIG. 10 for y-z paired coil drive. For paired drive, the single board computer 156 (FIG. 21) sequentially drives the x-y pair, x-(−y) pair, and z axis for each x-y-z coil set 106a, 106b, 106c (FIGS. 1 and 15). Here, "(−y)" means inverted phase on y axis drive. The measured sensor coil response for paired-coil drive must be scaled down by 1.4142 because of vector summing of the two coils driven together. Alternatively, the coil-driver power could be scaled down by 0.7071 in hardware when driving pairs so that the vector sum of two coils equals the magnetic vector of a single coil drive. The single board computer 156 measures the sensor coil response for each corner in normal drive and paired drive, and then selects the strongest signal from each corner comparing the sum of $x^2$, $y^2$, and $z^2$ normal coil drive response to the sum of $(x-y)^2$, $(x-(-y))^2$, and $z^2$ paired coil drive response. The strongest signal from each corner is used to calculate the location of the sensor coil 114 using the trilateration method described in the above equations, using the improved method. This example illustrates paired x-y coil drive; and by logical extension this may also apply to x-z, or y-z paired drive, or in alternative structures orthogonal pairs of drive coils.

In a non-limiting approach, the z-axis coil is replaced by a pair of orthogonal coils, z' and z" (FIGS. 4, 5, 6, 12, 13, and 14 inter alia). These z' and z" coils are arranged in pseudo-orthogonal or dual orthogonal placement. In this approach, the z-coil responses or measured z-coil values are calculated as the vector sum of the sense coils response to z' and z". By trilateration, the radial distance equation for each corner is:

$$r = k/\sqrt[6]{((z'^2 + z''^2 + a^2))}$$

where "a" is calculated using the x-y sense coil measurement information, then here, the location of the sense coil [z', z", a] would be:

$$r_1^2 = k/\sqrt[6]{((mz'_1{}^2 + mz''_1{}^2 + ma_1{}^2))}$$

$$r_2^2 = k/\sqrt[6]{((mz'_2{}^2 + mz''_2{}^2 + ma_2{}^2))}$$

$$r_3^2 = k/\sqrt[6]{((mz'_3{}^2 + mz''_3{}^2 + ma_3{}^2))}$$

In this alternative, $mz'_1$, $mz''_1$, and $ma_1$ are measured sense coil responses from corner 1 124; $mz'_2$, $mz''_2$, and $ma_2$ are measured sense coil responses form corner 2 126; and $mz'_3$, $mz''_3$, and $ma_3$ are measured sense coil responses from corner 3 128. In this alternative, $ma_1^2$, $ma_2^2$, and $ma_3^2$ are measured vectors using the x drive coil and y drive coil to obtain the vector sum for each corner. In this alternative method for calculation of the EM tip location the, by trilateration, the sense coil location [z', z", and a] distance equation for each corner is:

$$z' = (r_1^2 - r_2^2 + u^2)/(2u)$$

$$z'' = [(r_1^2 - r_3^2 + v^2 + w^2)/(2 \times w)] - [(v/w) \times a]$$

$$a = +/- \sqrt{[r_1^2 - z'^2 - z''^2]}$$

In this alternative, the coordinates of the sphere used for trilateration may be as follows: sphere 1=[0,0], sphere 2=[0,u], and sphere 3=[v,w]. This or alternative sets or combinations of the above non-limiting approaches may be utilized within the system.

An improvement of the paired-coil drive may be to add programmable (DAC) power control to the coil drivers on the drive coil drive electronics board 110 (FIGS. 22, 23, 28, and 31). Here, the single board computer 156 (FIG. 16, 21) has the capability to select pairs of drive current power settings which steer the virtual axis of the paired coils from 0 to 90 degrees. Inversion of one of the coil drivers in the pair provides the capability for virtual axis from −90 to 0 degrees. In this design, the single board computer 156 selects pairs of power settings output to the x-y paired coil driver to sweep the virtual drive axis from 0 to 90 degrees while recording the sensor coil response and this process is repeated with the y-coil driver phase inverted to sweep from −90 to 0 degrees. The angle of the virtual axis when the sensor coil response data is maximum indicates the sensor coil 114 (FIG. 1) is parallel to the virtual axis and the angle of the virtual axis when the sensor coil response data is minimum indicates the sensor coil 114 is perpendicular to the virtual axis. Here the maximum angle and minimum angle are orthogonal (perpendicular). The single board computer 156 (FIG. 16, 21) calculates the optimum virtual x axis at forty-five degrees from the measured angle for maximum (or minimum) response and calculates the optimum virtual y axis as an angle orthogonal to the virtual x axis. As all x-y-z coil sets 106a, 106b, 106c, (or x-y-z'-z") are mechanically aligned the solution for best virtual axes in one corner applies to all corners in the patient drive block 122, 150 (FIGS. 1, 16, 17 and 18). The single board computer 156 (FIG. 16, 21) measures the sensor coil response for all corners using these optimum virtual x axis, optimum virtual y axis plus normal z axis. The sum of (virtual x)$^2$, (virtual y)$^2$, and z$^2$ sensor coil responses for each corner is used to calculate the position of the sensor coil 114 (FIG. 1) using the trilateration method described in the above equations. This example illustrates paired x-y coil drive; and by logical extension this also applies to x-z, or y-z paired drive; however, the preference in this development is to improve accuracy of horizontal location and thus use paired x-y drive. Furthermore, in arrangements that utilize a quadruplet embodiment of drive coils, the single board computer 156 (FIG. 16) may calculate the sensor coil location for all corners using an optimized choice of the measured x, virtual x, measured y, virtual y, virtual x-y, measured z', virtual z', measured z", virtual z", and virtual z'-z".

An alternative, non-limiting, method for finding the optimum virtual x and virtual y axis in the programmable pair-coil drive above is to use successive approximation instead of sweeping 0 to 90 degrees. In this approach, the single board computer 156 (FIG. 16) has the capability to select pairs of drive current power settings which steer the virtual axis from −90 to +90 degrees. The single board computer first tests the sensor coil response to the paired coils at virtual axes +45 and −45 degrees and selects the virtual axis with the stronger response. Using the stronger axis, the computer then tests the sensor coil response to paired coils at +22.5 and −22.5 degrees from the current virtual axis and selects the virtual axis with the stronger response. This process continues for +/−11.25 degrees, +/−5.625 degrees, until the limits of drive power resolution are reached. The resulting virtual axis is the axis of maximum response. The single board computer 156 calculates the optimum virtual x axis at forty-five degrees from the measured angle for maximum response and calculates the optimum virtual y axis as an angle orthogonal to the virtual x axis. This approach may in some embodiments be extended to the z' and z" drive coils.

A selection of the best set of virtual axes in a triplet-coil drive scheme may be accomplished with programmable power control to the coil drivers for each axis, and with the driver control to selectively invert the phase of any coil in the triplet x-y-z coil sets 106a, 106b, 106c (see FIG. 16). Here, the single board computer 156 (FIG. 16) has the capability to select pairs of drive current power settings which steer the x-y virtual axis of the paired coils from 0 to 90 degrees. Inversion of one of the coil drivers in the pair provides the capability for x-(−y) virtual axis from −90 to 0 degrees. With the addition of the third coil drive and inversion the single board computer 156 may sweep the virtual axis 0 to 90 and −90 to 0 degrees in z range. The microcomputer (in alternative embodiments multiple microcomputers) may select the pairs of current settings output to the x-y paired coil driver to sweep the virtual drive axis from 0 to 90 degrees while recording the sensor coil response and this process is repeated with the y coil driver phase inverted to sweep from −90 to 0 degrees. The angle of the x-y virtual axis when the sensor coil response data is maximum indicates the sensor coil 114 (FIG. 1, 16) is parallel for the x-y plane. The single board computer 156 then sets this x-y axis and sweeps the z axis drive from −90 to 0 and 0 to 90 degrees while recording the sensor coil response. The polar angle of the x-y-z virtual axis when the sensor coil response data is at maximum indicates the sensor coil 114 is parallel to this virtual x-y-z axis. The single board computer 156 then repeats this process to find the minimum sensor coil response sweeping x, y, and z axes. The polar angle of the x-y-z virtual axis when the sensor coil response data is minimum indicates the sensor coil 114 is perpendicular to this virtual x-y-z axis. These two vectors, virtual minimum and virtual maximum, define a plane intersecting the sensor coil 114. For optimum response, the single board computer 156 calculates a virtual x axis 45 degrees between the maximum and minimum vectors, then calculates the virtual y axis as 90 degrees from the virtual x in the plane defined previously. Here, virtual z axis is defined as orthogonal to the plane of virtual minimum and virtual maximum vectors. The single board computer 156 then tilts the virtual z axis and the plane of virtual x axis and virtual y axis 45 degrees toward the virtual minimum vector, and the result is the optimal virtual axis set which maximizes the sensor coil response. As all x-y-z coil sets 106a, 106b, 106c are mechanically aligned the solution for best virtual axes in one corner applies to all corners in the driver array. The single board computer 156 measures the sensor coil response for all corners using these optimum virtual x, y, and z axes. The sum of (virtual x)$^2$, (virtual y)$^2$, and (virtual z)$^2$ sensor coil responses for each corner may be used to calculate the sensor coil 114 location and orientation using the trilateration method described in the above equations. One method to maintain the optimum x-y-z axis over time is to continuously test the sensor coil response to small deviations (offset angle) from the optimum axis (see FIG. 29b). Here, the single board computer 156 compares the sum of (virtual x)$^2$, (virtual y)$^2$, and (virtual z)$^2$ sensor coil responses for the current virtual axis to the sum for virtual axis plus offset angle and the sum for virtual axis minus offset angle. The computer 156 then selects the axis with the largest summed response—this becomes the new optimum x-y-z axis and the process continues to iterate testing small deviations over time. This approach may in some embodiments be further extended for use in quadruplet drive coil sets.

The single board computer 156 may then graphically display the sensor coil position on the display 104 of the control box 102. The position is continuously updated adding onto the previous graphical data to create a track or path of the sensor coil 114 over time. Furthermore, as the track or path of the sensor coil 114 is displayed, the display also shows the orientation of the sensor coil in at least the x-y coordinate plane. The user interface of the single board computer 156 allows the user to clear the recorded track or to save the recorded track to non-volatile memory. Touch-screens have been described; however keyboard or other data input, or user interface options may be used.

The construction details above for the control box 102 (FIGS. 1, 21) may provide for a tethered device with the display/control separate from the patient block 122, 150 (FIGS. 1, and 21). However, an alternative construction would be to build a device or system in which the patient block 122, 150 is battery-powered and connected wirelessly to the control box 102. In another variation, the control box 102 could be integrated into or as part of the patient block and placed on the patient chest or other locations to track medical device position. Wireless and/or wired connections are thus optionally available for the connections of the drive coil sets to the control or system components for the driving thereof; as well as for the connections of the sensor coil to the control or system components for measuring or receiving the response signals of the sensor coil.

An alternative construction would be to use four or more drive coils 106 oriented as a square, rectangle, pentagon, circle, oval, geometric, or any other suitable shape, in or as the patient drive block 122, 150 (FIGS. 1, 18, 19 and 20). In this non-limiting approach, the location, disposition, and orientation may be determined using multilateration.

An alternative construction would be to use a capacitor 131 (FIG. 6) in operable association with each of the discrete drive coils 106 or each axis of each discrete drive coil 124, 126, and 128. This alternative embodiment may create an LC circuit that has unique benefits for optimizing the energizing of the drive coils, the re-energizing of the drive coils, the sequential energizing of the drive coils, the synchronous energizing of the drive coils, and the de-energizing the drive coils.

An embodiment of the current development incorporates (FIGS. 1, 16, 17, and/or 18) electrocardiograph (ECG) monitoring into the medical device location system to facilitate placement of the medical device with sensor coil 114 in close proximity to the heart. Here the patient drive block 150 may be modified with one or more ECG pads 154 and ECG lead wires 152 which attach to the patient's chest and the third ECG lead is provided by a conductive wire 146 added in or otherwise made part of the core of the guide wire or stylet sensor coil 114.

An ECG amplifier may be added to the main interface board 158 (FIG. 22), and the single board computer 156 may then present the ECG on the display 104 as the medical device such as a catheter is advanced within the patient's or subject's body. The user may observe changes in the P-wave or other wave elements of the ECG as the medical device/catheter reaches the heart. Ideally, the single board computer 156 could use a waveform analysis to assist the user in recognizing changes occurring to the P-wave or other waveforms.

A component to this design may include connecting the signals from the sensor coil 114 and ECG 146 to the user control box 102. This is complicated in practice by covering the entire patient and patient block 150 with sterile drapes for insertion of the patient's medical device/catheter. In this design, a miniature stereo phone plug or similar could be used to pierce a plastic bag and connect to cable 120, 146 a pigtail from the user control box 102.

Methods, devices and systems may thus be provided for one or both of two- or three-dimensional location of the disposition of a sensor coil in a subject including: an array of electromagnetic drive coil sets, each set having two or three dimensionally oriented drive coils; a sensor coil being electromagnetically communicative with the array of electromagnetic drive coil sets; and, a system controller communicative with and adapted to energize one or more of the electromagnetic coils in the array of electromagnetic drive coil sets, the energizing of the one or more of the electromagnetic coils including one or more of energizing the coils singly, or in pairs of x-y and y-z or x-z coils or x-y and y-z' and/or y-z" or x-z' and/or x-z" and/or z'-z" coils while measuring the response of the sensor coil; whereby the system uses the measurements of the responses of the sensor coil to calculate the location and orientation of the sensor coil relative to said drive coil sets.

This may include two- and/or three-dimensional location of a catheter in tissue using an array of x-y or x-y-z or x-y-z'-z" oriented electromagnetic coils, where a sensor coil may be associated with one or more catheter tips, and where the system controller may energize one or more external coils, such as but not limited to, pairs of x-y and y-z or x-z coils or x-y and y-z' and/or y-z" or x-z' and/or x-z" and/or z'-z" coils while measuring the response of the sensor coil; the system may use these sensor coil measurements to calculate the position and orientation of the catheter tip, and in some implementations, the system controller may graphically display the catheter tip position, depth and/or orientation, e.g., but not limited to, over time.

From the foregoing, it is readily apparent that new and useful implementations of the present systems, apparatuses and/or methods have been herein described and illustrated which fulfill numerous desiderata in remarkably unexpected fashions. It is, of course, understood that such modifications, alterations and adaptations as may readily occur to the artisan confronted with this disclosure are intended within the spirit of this disclosure, which is limited only by the scope of the claims appended hereto.

What is claimed is:

1. A medical device locating system for determining a disposition of a sensor coil in a subject, the system comprising:
   an array of three or more quadruplet drive coil sets, each drive coil set including at least four discrete electromagnetic coils, the at least four discrete electromagnetic coils including a first electromagnetic coil, a second electromagnetic coil, a third electromagnetic coil, and a fourth electromagnetic coil, the first electromagnetic coil being orthogonal to the second electromagnetic coil, and at least one of the third electromagnetic coil and the fourth electromagnetic coil being non-orthogonal to the first and second electromagnetic coils;
   an elongate flexible probe comprising:
   a magnetically permeable, conductive core wire having a proximal end and a distal end, and
   at least one sensor coil disposed toward the distal end of the core wire, said sensor coil configured to provide one or more sensor coil response signals;
   a first system component configured to provide drive signals energizing the discrete electromagnetic coils by:
   sequentially driving one or more of said discrete electromagnetic coils within a drive coil set and selectively providing phase inversion of the drive signal to any one, two, three or more of the discrete electromagnetic coils within the drive coil set, or
   simultaneously energizing one, a pair, a triplet or a quadruplet of said discrete electromagnetic coils within a drive coil set;
   a second system component configured to measure resulting one or more sensor coil response signals; and
   a processor configured to determine the sensor coil disposition relative to the array of three or more quadruplet drive coil sets based on the measured resulting sensor coil response signals.

2. The system of claim 1, wherein the core wire provides an electrical pathway configured to measure an electrocardiogram (ECG) signal.

3. The system of claim 2, further comprising two additional surface ECG leads configured to be placed on the subject.

4. The system of claim 1, wherein the core wire has a shape selected from the group consisting of a circle, an ellipse, a square, a pentagon, a hexagon and an octagon.

5. The system of claim 1, wherein the core wire comprises a material selected from the group consisting of metglas, iron, nanoperm, mu-metal, cobalt-iron, permalloy, ferrous stainless steel and ferrite.

6. The system of claim 1, wherein the sensor coil provides a measurable response to an electromagnetic field when the sensor coil is positioned within 36 inches from the centroid of the array of three or more quadruplet drive coil sets.

7. The system of claim 1, further comprising a display configured to display the disposition of the sensor coil in the subject relative to the array of the quadruplet drive coil sets.

8. The system of claim 7, wherein the display simultaneously displays a P-wave and a QRS complex of the subject over time with the disposition of the sensor coil.

9. The system of claim 7, wherein said display displays the disposition of the sensor coil in the subject by indicating a height, width or depth of the sensor coil in said subject relative to the array of the quadruplet drive coil sets.

10. The system of claim 7, wherein said display displays the disposition of the sensor coil in the subject by indicating an angular orientation of the sensor coil in said subject relative to the array of the quadruplet drive coil sets.

11. The system of claim 1, wherein the second system component is configured to measure resulting one or more sensor coil response signals by selectively amplifying or filtering the one or more sensor coil response signals to produce one or more optimized sensor coil response signals.

12. The system of claim 11, wherein the processor is configured to determine the sensor coil disposition relative to the array of three or more quadruplet drive coil sets by: selecting optimum sensor coil response signals from the optimized sensor coil response signals; and calculating an intersection of spheres using said optimum sensor coil response signals.

13. The system of claim 1, further comprising an automatic gain control circuit within the second system component, the automatic gain control circuit receiving the one or more sensor coil response signals from the sensor coil and maximizing the sensor coil response signals before communicating the sensor coil response signals to the second system component.

14. The system of claim 1, wherein the quadruplet drive coil sets are provided as virtual pairs, virtual triplets or virtual quadruplets, and wherein:
   the first system component is configured to provide AC drive signals by sequentially sweeping virtual electromagnetic drive vectors from 0 to 90 degrees and −90 to 0 degrees for x, y, z' and z" axes of the quadruplet drive coil sets;
   the processor is further configured to:
   determine angle values of maximum and minimum sensor coil responses within a plane using paired coil programmable current drive sweeping a range from 0 to 90 degrees;
   determine the angle values of maximum and minimum sensor coil responses within a plane using paired coil programmable current drive sweeping using inverted phases of at least one coil and sweeping a range from −90 to 0 degrees;
   determine at least one set of optimal virtual drive x and y axes for at least two of the quadruplet drive coils as values corresponding to plus and minus 45 degrees from the maximum or minimum sensor coil responses; and
   determine an optimal virtual drive orthogonal to the plane of the optimal virtual drive axes to provide at least one optimal virtual drive axis.

15. The system of claim 1, further comprising an x-axis tilt meter and y-axis tilt meter which use gravity to measure the x-axis and y-axis tilt from true vertical.

16. The system of claim 1, wherein the a third electromagnetic coil is orthogonal to the fourth electromagnetic coil.

17. The system of claim 1, wherein the third and four electromagnetic coils are non-orthogonal to the first and second electromagnetic coils.

18. A method for determining a disposition of a sensor probe in a subject, the method comprising:

driving an array of three or more quadruplet drive coil sets, each drive coil set including at least four discrete electromagnetic coils driven by drive signals to generate respective electromagnetic wave fields, the at least four discrete electromagnetic coils including a first electromagnetic coil, a second electromagnetic coil, a third electromagnetic coil, and a fourth electromagnetic coil, the first electromagnetic coil being orthogonal to the second electromagnetic coil, and at least one of the third electromagnetic coil and the fourth electromagnetic coil being non-orthogonal to the first and second electromagnetic coils;

receiving one or more discrete sensor probe response signals from a moveable sensor probe, the sensor probe including a discrete magnetically permeable conductive core wire and a discrete sensor coil, the magnetically permeable conductive core wire configured to generate a first response signal in response to electrical stimuli of the subject and the sensor coil configured to generate one or more second response signals responsive to the respective electromagnetic wave fields;

measuring the first response signals from the magnetically permeable conductive core wire and the second response signals from the discrete sensor coil;

providing modified drive signals to one or more electromagnetic coils to maximize or optimize one or both:

the generated electromagnetic wave fields, and the one or more sensor coil response signals;

measuring first modified response signals from the magnetically permeable conductive core wire and second modified response signals from the discrete sensor coil; and determining sensor probe disposition in the subject relative to the array of three or more quadruplet drive coil sets based on the measured modified sensor coil response signals.

19. The method of claim 18, wherein measuring the first response signals from the magnetically permeable conductive core wire comprises receiving an electrical signal through the magnetically permeable conductive core wire providing one lead signal enabling the successive measurements for an electrocardiogram (ECG) of said subject.

20. The method of claim 18, wherein measuring the second response signals from the discrete sensor coil comprises normalizing the amplitude of the second response signals from the discrete sensor coil.

21. The method of claim 18, wherein measuring the second modified response signals from the discrete sensor coil comprises normalizing the amplitude of the second modified response signals from the discrete sensor coil.

22. The method of claim 18, further comprising measuring an electrocardiogram (ECG) signal with two additional surface ECG leads placed on the subject.

23. The method of claim 18, wherein the third electromagnetic coil is orthogonal to the fourth electromagnetic coil.

24. The method of claim 18, wherein the third and four electromagnetic coils are non-orthogonal to the first and second electromagnetic coils.

* * * * *